(12) United States Patent
Iverson et al.

(10) Patent No.: US 10,900,059 B2
(45) Date of Patent: Jan. 26, 2021

(54) METHODS FOR GENERATING ENGINEERED ENZYMES

(71) Applicant: Research Development Foundation, Carson City, NV (US)

(72) Inventors: Brent Iverson, Austin, TX (US); Peter Marek, Austin, TX (US); Joseph Taft, Austin, TX (US)

(73) Assignee: Research Development Foundation, Carson City, NV (US)

(*) Notice: Subject to any disclaimer, the term of this patent is extended or adjusted under 35 U.S.C. 154(b) by 447 days.

(21) Appl. No.: 15/518,789

(22) PCT Filed: Oct. 14, 2015

(86) PCT No.: PCT/US2015/055494
§ 371 (c)(1),
(2) Date: Apr. 13, 2017

(87) PCT Pub. No.: WO2016/061199
PCT Pub. Date: Apr. 21, 2016

(65) Prior Publication Data
US 2017/0233781 A1    Aug. 17, 2017

Related U.S. Application Data

(60) Provisional application No. 62/063,836, filed on Oct. 14, 2014.

(51) Int. Cl.
| | | |
|---|---|---|
| *C12P 21/00* | (2006.01) | |
| *G16B 30/00* | (2019.01) | |
| *C12Q 1/37* | (2006.01) | |
| *C12Q 1/48* | (2006.01) | |
| *C12Q 1/6816* | (2018.01) | |
| *C12Q 1/6869* | (2018.01) | |
| *G01N 33/50* | (2006.01) | |

(52) U.S. Cl.
CPC ............. *C12P 21/005* (2013.01); *C12Q 1/37* (2013.01); *C12Q 1/485* (2013.01); *C12Q 1/6816* (2013.01); *C12Q 1/6869* (2013.01); *C12Y 207/10001* (2013.01); *C12Y 304/2207* (2013.01); *G01N 33/5008* (2013.01); *G16B 30/00* (2019.02); *G01N 2333/91205* (2013.01); *G01N 2333/96466* (2013.01)

(58) Field of Classification Search
None
See application file for complete search history.

(56) References Cited

U.S. PATENT DOCUMENTS 8,945,855 B2 * 2/2015 Iverson .............. C12N 15/1037
435/194

FOREIGN PATENT DOCUMENTS

WO    WO 2014-004540    1/2014

OTHER PUBLICATIONS

Aridor and Hannan, "Traffic jam: a compendium of human diseases that affect intracellular transport processes," *Traffic*, 1:836-851, 2000.
Aridor and Hannan, "Traffic jams II: an update of diseases of intracellular transport," *Traffic*, 3:781-790, 2002.
Beinfeld, "Prohormone and proneuropeptide processing. Recent progress and future challenges," *Endocrine*, 8:1-5, 1998.
Boder, et al., "Yeast surface display for screening combinatorial polypeptide libraries," *Nature Biotechnology*, 15:553-557, 1997.
Boulware and Daugherty, "Protease specificity determination by using cellular libraries of peptide substrates (CLiPS)," *Proc. Nat. Acad. Sci., USA*, 103:7583-7588, 2006.
Bourbonnais et al., "Isolation and characterization of S. cerevisiae mutants defective in somatostatin expression: cloning and functional role of a yeast gene encoding an aspartyl protease in precursor processing at monobasic cleavage sites," *EMBO J.*, 12:285-294, 1993.
Cawley et al., "Specificity and kinetic studies on the cleavage of various prohormone mono- and paired-basic residue sites by yeast aspartic protease 3," *J. Biol. Chem.*, 271:4168-4176, 1996.
Chen, et al., "A general strategy for the evolution of bond-forming enzymes using yeast display," *Proc. Natl. Acad. Sci., USA*, 108(28):11399-11404, 2011.
Craik, et al., "Proteases as therapeutics," *Biochem. J.*, 435:1-16, 2011.
Diamond et al., "Methods for mapping protease specificity," *Curr. Opin. Chem. Biol.*, 11(1):46-51, 2007.
Dix et al., "Global Mapping of the Topography and Magnitude of Proteolytic Events in Biological Systems," *Cell*, 134:679-691, 2008.
Dougherty et al., "Biochemical and mutational analysis of a plant virus polyprotein cleavage site," *EMBO J.*, 7(5):1281-1287, 1988.
Gagnon-Arsenault et al., "Fungal yapsins and cell wall: a unique family of aspartic peptidases for a distinctive cellular function," *FEMS yeast research*, 6:966-978, 2006.
Gai et al., "Yeast surface display for protein engineering and characterization," *Curr. Opin. Struct. Biol.*, 17:467-473, 2007.
Gera et al., "Protein selection using yeast surface display," *Methods*, 60(1):15-26, 2013.
Girard et al., "Secretomes: The fungal strike force," *Proteomics*, 13:597-608, 2013.
Han et al., "Self-assembled amyloid-like oligomeric-cohesin Scaffoldin for augmented protein display on the *Saccharomyces cerevisiae* cell surface," *Appl. Environ. Microbiol.*, 78(9):3249, 2012.

(Continued)

*Primary Examiner* — Anand U Desai
(74) *Attorney, Agent, or Firm* — Parker Highlander PLLC

(57) ABSTRACT

Provided are improved methods for identifying the substrate recognition specificity or activity of a protease, convertase (sortase), or kinase. In some embodiments, methods are provided for identifying the endogenous protease or convertase cleaving patterns (e.g., "cleaveOme") inside the secretory pathway of a living cell. Select embodiments involve aspects of yeast endoplasmic reticulum sequestration screening and next generation sequencing. Methods of producing polypeptides in Kex2 knockout yeast are also provided.

32 Claims, 23 Drawing Sheets
Specification includes a Sequence Listing.

(56) References Cited

OTHER PUBLICATIONS

Hegde and Keenan, "Tail-anchored membrane protein insertion into the endoplasmic reticulum," *Nat Rev Mol Cell Biol.*, 12(12):787-98, 2011.
Huang et al., "Conserved WCPL and CX4C domains mediate several mating adhesin interactions in *Saccharomyces cerevisiae*," *Genetics*, 182(1):173-89, 2009.
International Preliminary Report on Patentability issued in corresponding PCT Application No. PCT/US2015/055494, dated Apr. 27, 2017.
International Search Report and Written Opinion issued in corresponding PCT Application No. PCT/US2015/055494, dated Apr. 14, 2016.
Kim et al., "Construction of an in vitro trans-sialylation system: surface display of Corynebacterium diphtheriae sialidase on *Saccharomyces cerevisiae*," *Appl Microbiol Biotechnol.*, 88(4):893-903, 2010.
Komano et al., "Purification and characterization of the yeast glycosylphosphatidylinositol-anchored, monobasic-specific aspartyl protease yapsin 2 (Mkc7p)," *J. Biol. Chem.*, 274:24431-24437, 1999.
Komano, H., Seeger, M., Gandy, S., Wang, G., Krafft, G., and Fuller, R., "Involvement of cell surface glycosyl-phosphatidylinositol-linked aspartyl proteases in alpha-secretase-type cleavage and ectodomain solubilization of human Alzheimer beta-amyloid precursor protein in yeast," *J. Biol. Chem.*, 273:31648-31651 1998 . . . .
Ledgerwood et al., "Yeast aspartic protease 3 (Yap3) prefers substrates with basic residues in the P2, P1 and P2' positions," *FEBS Lett.*, 383:67-71, 1996.
Lee et al., "Isomaltulose production via yeast surface display of sucrose isomerase from *Enterobacter* sp. FMB-1 on *Saccharomyces cerevisiae*," *Bioresource Technol.*, 102:9179-9184, 2011.
Li et al., "Commercial proteases: present and future," *FEBS Lett.*, 587, 1155-1163, 2013.
Lin et al., "A novel fragment of antigen binding (Fab) surface display platform using glycoengineered Pichia pastoris," *J. Immunol. Methods*, 375:159-165, 2012.
Matthews et al., "A survey of furin substrate specificity using substrate phage display," *Protein Sci.*, 3:1197-1205, 1994.
O'Donoghue et al., "Global Identification of Peptidase Specificity by Multiplex Substrate Profiling," *Nat. Methods*, 9:1095-1100, 2012.
O'Loughlin et al., "Diversification and Specialization of HIV Protease Function During In Vitro Evolution," *Mol. Biol. Evol.*, 23(4):764-772, 2006.
Olsen et al., "Identification and characterization of *Saccharomyces cerevisiae* yapsin 3, a new member of the yapsin family of aspartic proteases encoded by the YPS3 gene," *Biochem. J.*, 339(Pt 2): 407-411, 1999.
Paltridge et al., "The secretome in cancer progression," *Biochim. Biophys. Acta*, 1834(11)2233-2241, 2013.
Porro et al., "Recombinant protein production in yeasts," *Methods Mol. Biol.* 31:245-259, 2004.
Ramachandran et al., "Targeting proteinase-activated receptors: therapeutic potential and challenges," *Nat. Rev. Drug Discov.*, 11(1):69-86, 2012.
Rapoport, "Protein translocation across the eukaryotic endoplasmic reticulum and bacterial plasma membranes," *Nature*, 450(7170):663-9, 2007.
Rockwell and Fuller, "Interplay between S1 and S4 subsites in Kex2 protease: Kex2 exhibits dual specificity for the P4 side chain," *Biochemistry*, 37:3386-3391, 1998.
Rockwell et al., "Internally consistent libraries of fluorogenic substrates demonstrate that Kex2 protease specificity is generated by multiple mechanisms," *Biochemistry*, 36:1912-1917, 1997.
Roebroek et al., "Failure of ventral closure and axial rotation in embryos lacking the proprotein convertase Furin," *Development*, 125:4863-4876, 1998.
Rozan et al., "Plasticity of extended subsites facilitates divergent substrate recognition by Kex2 and furin," *J. Biol. Chem.*, 279:35656-35663, 2004.
Scholle et al., "Mapping protease substrates by using a biotinylated phage substrate library," *ChemBioChem.*, 7:834-838, 2006.
Seidah and Prat, "Precursor convertases in the secretory pathway, cytosol and extracellular milieu," *Essays Biochem.*, 38:79-94, 2002.
Sellamuthu et al., "Engineering of protease variants exhibiting altered substrate specificity," *Biochem. Biophys. Res. Commun.*, 371(1):122-126, 2008.
Sinha et al., "Causes of proteolytic degradation of secreted recombinant proteins produced in methylotrophic yeast Pichia pastoris: case study with recombinant ovine interferon-tau," *Biotechnol. Bioengineer.*, 89:102-112, 2005.
Small et al., "Predotar: A tool for rapidly screening proteomes for N-terminal targeting sequences," *Proteomics*, 4(6):1581-90, 2004.
Sudbery, P., "The expression of recombinant proteins in yeasts," *Curr. Opin. Biotechnol.*, 7:517-524, 1996.
Varadarajan, et al., "An Engineered Protease that Cleaves Specifically after Sulfated Tyrosine," *Angew. Chemie., Int. Ed.*, 47(41):7861-7863, 2008.
Varadarajan, et al., "Engineering of protease variants exhibiting high catalytic activity and exquisite substrate selectivity," *Proc. Natl. Acad. Sci.*, 102(19):6855-6860, 2005.
Varadarajan, et al., "Highly active and selective endopeptidases with programmed substrate specificities," *Nature Chemical Biology*, 4(5):290-294, 2008.
Varadarajan, et al., "Proteases that can distinguish among different post-translational forms of tyrosine engineering using multicolor flow cytometry," *J. Am. Chem. Soc.*, 131(50):18186-18190, 2009.
Yi et al., "Engineering of TEV protease variants by yeast ER sequestration screening (YESS) of combinatorial libraries," *Proc. Natl. Acad. Sci.*, 110(18):7229-7234, 2013.
Yi et al., "Yeast Endoplasmic Reticulum Sequestration Screening for the Engineering of Proteases from Libraries Expressed in Yeast," *Methods Mol. Biol.*, 1319:81-93, 2015.
Zhou et al., "Proteolytic processing in the secretory pathway," *J. Biol. Chem.*, 274:20745-20748, 1999.

\* cited by examiner

Position Y-2

| | A | C | E | D | G | F | I | H | K | M | L | N | Q | P | S | R | T | W | V | Y |
|---|---|---|---|---|---|---|---|---|---|---|---|---|---|---|---|---|---|---|---|---|
| Sort 0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Sort 1 | 1.0 | 1.1 | 1.2 | 1.3 | 1.1 | 0.8 | 1.0 | 0.9 | 0.7 | 1.0 | 1.0 | 1.2 | 1.0 | 1.4 | 0.7 | 0.7 | 0.8 | 0.7 | 1.1 | 1.6 |
| Sort 2 | 1.1 | 1.1 | 1.2 | 1.3 | 1.1 | 0.7 | 1.0 | 0.9 | 0.6 | 0.9 | 1.0 | 1.3 | 1.0 | 1.4 | 0.7 | 0.6 | 0.7 | 0.6 | 1.2 | 1.6 |
| Sort 3 | 1.0 | 1.1 | 1.3 | 1.6 | 1.2 | 0.6 | 1.0 | 0.8 | 0.5 | 0.9 | 1.0 | 1.5 | 1.0 | 1.8 | 0.6 | 0.5 | 0.7 | 0.5 | 1.1 | 2.0 |
| Sort 4 | 1.0 | 1.1 | 1.3 | 1.8 | 1.1 | 0.5 | 1.0 | 0.9 | 0.4 | 0.9 | 1.0 | 1.5 | 1.0 | 1.8 | 0.6 | 0.4 | 0.6 | 0.4 | 1.0 | 2.3 |
| Sort 5 | 1.0 | 1.1 | 1.2 | 1.9 | 1.2 | 0.5 | 1.0 | 0.8 | 0.4 | 0.9 | 1.1 | 1.6 | 1.0 | 2.0 | 0.5 | 0.3 | 0.5 | 0.4 | 0.9 | 2.4 |

Position Y-1

| | A | C | E | D | G | F | I | H | K | M | L | N | Q | P | S | R | T | W | V | Y |
|---|---|---|---|---|---|---|---|---|---|---|---|---|---|---|---|---|---|---|---|---|
| Sort 0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Sort 1 | 0.8 | 1.0 | 1.4 | 1.4 | 0.8 | 1.0 | 1.5 | 1.3 | 0.6 | 1.2 | 1.3 | 1.1 | 1.1 | 0.7 | 0.5 | 0.5 | 0.5 | 0.7 | 1.3 | 1.6 |
| Sort 2 | 0.8 | 1.0 | 1.5 | 1.4 | 0.8 | 1.0 | 1.6 | 1.3 | 0.5 | 1.2 | 1.4 | 1.1 | 1.1 | 0.7 | 0.4 | 0.5 | 0.5 | 0.6 | 1.4 | 1.7 |
| Sort 3 | 0.7 | 0.9 | 1.7 | 1.7 | 0.6 | 0.9 | 1.8 | 1.2 | 0.3 | 1.1 | 1.5 | 1.1 | 1.1 | 0.6 | 0.3 | 0.3 | 0.3 | 0.5 | 1.3 | 2.3 |
| Sort 4 | 0.7 | 0.9 | 1.7 | 2.0 | 0.5 | 0.9 | 1.7 | 1.2 | 0.3 | 1.1 | 1.6 | 1.2 | 1.0 | 0.6 | 0.3 | 0.2 | 0.3 | 0.4 | 1.2 | 2.9 |
| Sort 5 | 0.6 | 0.9 | 1.7 | 2.2 | 0.4 | 0.9 | 1.6 | 1.1 | 0.2 | 1.0 | 1.7 | 1.2 | 0.9 | 0.5 | 0.3 | 0.2 | 0.2 | 0.4 | 1.1 | 3.5 |

Position Y+1

| | A | C | E | D | G | F | I | H | K | M | L | N | Q | P | S | R | T | W | V | Y |
|---|---|---|---|---|---|---|---|---|---|---|---|---|---|---|---|---|---|---|---|---|
| Sort 0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Sort 1 | 1.1 | 1.1 | 1.0 | 1.1 | 1.0 | 1.4 | 0.8 | 1.2 | 0.7 | 1.1 | 0.9 | 0.9 | 1.1 | 0.5 | 1.0 | 0.9 | 0.8 | 1.3 | 0.9 | 1.4 |
| Sort 2 | 1.1 | 1.1 | 1.0 | 1.1 | 1.0 | 1.4 | 0.8 | 1.2 | 0.6 | 1.1 | 0.9 | 0.8 | 1.1 | 0.4 | 1.0 | 0.9 | 0.8 | 1.4 | 0.9 | 1.5 |
| Sort 3 | 1.0 | 1.1 | 0.9 | 1.1 | 0.9 | 1.9 | 0.8 | 1.3 | 0.5 | 1.1 | 0.8 | 0.9 | 1.0 | 0.4 | 0.9 | 0.8 | 0.7 | 1.7 | 0.8 | 1.9 |
| Sort 4 | 0.9 | 1.1 | 0.7 | 1.0 | 0.6 | 2.3 | 0.8 | 1.4 | 0.3 | 1.0 | 0.9 | 0.8 | 1.0 | 0.5 | 0.9 | 0.8 | 0.7 | 1.9 | 0.7 | 2.4 |
| Sort 5 | 0.8 | 1.1 | 0.7 | 0.9 | 0.5 | 2.9 | 0.8 | 1.4 | 0.3 | 1.0 | 0.8 | 0.7 | 0.9 | 0.5 | 0.9 | 0.7 | 0.6 | 2.2 | 0.7 | 2.8 |

Position Y+2

| | A | C | E | D | G | F | I | H | K | M | L | N | Q | P | S | R | T | W | V | Y |
|---|---|---|---|---|---|---|---|---|---|---|---|---|---|---|---|---|---|---|---|---|
| Sort 0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Sort 1 | 0.9 | 1.1 | 1.1 | 1.1 | 0.7 | 1.2 | 1.1 | 1.0 | 0.7 | 1.1 | 1.1 | 1.1 | 1.0 | 1.0 | 0.8 | 0.8 | 1.0 | 1.1 | 1.2 | 1.4 |
| Sort 2 | 1.0 | 1.2 | 1.1 | 1.1 | 0.7 | 1.2 | 1.2 | 1.0 | 0.6 | 1.1 | 1.1 | 1.1 | 1.0 | 1.0 | 0.8 | 0.8 | 1.0 | 1.1 | 1.2 | 1.4 |
| Sort 3 | 0.9 | 1.2 | 1.2 | 1.1 | 0.6 | 1.4 | 1.3 | 0.9 | 0.5 | 1.2 | 1.1 | 1.2 | 1.0 | 1.0 | 0.7 | 0.7 | 0.9 | 1.2 | 1.3 | 1.7 |
| Sort 4 | 0.9 | 1.3 | 1.1 | 1.2 | 0.5 | 1.4 | 1.4 | 0.9 | 0.4 | 1.3 | 1.2 | 1.2 | 1.0 | 1.0 | 0.7 | 0.6 | 0.8 | 1.2 | 1.4 | 1.9 |
| Sort 5 | 0.8 | 1.4 | 1.1 | 1.1 | 0.5 | 1.5 | 1.4 | 0.9 | 0.3 | 1.4 | 1.3 | 1.1 | 1.0 | 1.0 | 0.6 | 0.5 | 0.7 | 1.3 | 1.4 | 1.9 |

Position Y+3

| | A | C | E | D | G | F | I | H | K | M | L | N | Q | P | S | R | T | W | V | Y |
|---|---|---|---|---|---|---|---|---|---|---|---|---|---|---|---|---|---|---|---|---|
| Sort 0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Sort 1 | 0.8 | 1.1 | 0.4 | 0.6 | 0.9 | 1.4 | 1.2 | 1.1 | 0.6 | 1.0 | 1.2 | 0.9 | 0.7 | 1.5 | 0.6 | 0.8 | 0.6 | 1.5 | 1.1 | 1.7 |
| Sort 2 | 0.8 | 1.1 | 0.4 | 0.6 | 0.9 | 1.4 | 1.2 | 1.1 | 0.5 | 1.0 | 1.2 | 0.9 | 0.7 | 1.6 | 0.5 | 0.8 | 0.5 | 1.6 | 1.2 | 1.8 |
| Sort 3 | 0.7 | 1.1 | 0.3 | 0.5 | 0.9 | 1.6 | 1.2 | 1.0 | 0.4 | 0.9 | 1.1 | 0.9 | 0.6 | 2.0 | 0.4 | 0.7 | 0.4 | 2.1 | 1.1 | 2.3 |
| Sort 4 | 0.7 | 1.2 | 0.2 | 0.6 | 0.7 | 1.6 | 1.2 | 1.2 | 0.4 | 0.9 | 1.1 | 0.9 | 0.5 | 2.2 | 0.4 | 0.6 | 0.4 | 2.1 | 1.1 | 2.4 |
| Sort 5 | 0.6 | 1.1 | 0.2 | 0.5 | 0.7 | 1.7 | 1.2 | 1.2 | 0.3 | 0.8 | 1.0 | 0.9 | 0.5 | 2.5 | 0.4 | 0.6 | 0.4 | 2.7 | 0.9 | 2.5 |

FIG. 12B

Residue Cross-Talk and Model Building

Position Y-2

|  | A | C | E | D | G | F | I | H | K | M | L | N | Q | P | S | R | T | W | V | Y |
|---|---|---|---|---|---|---|---|---|---|---|---|---|---|---|---|---|---|---|---|---|
| Sort 0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Sort 1 | 1.0 | 1.1 | 1.2 | 1.3 | 1.1 | 0.8 | 1.0 | 0.9 | 0.7 | 1.0 | 1.0 | 1.2 | 1.0 | 1.4 | 0.7 | 0.7 | 0.8 | 0.7 | 1.1 | 1.6 |
| Sort 2 | 1.1 | 1.1 | 1.2 | 1.3 | 1.1 | 0.7 | 1.0 | 0.9 | 0.6 | 0.9 | 1.0 | 1.3 | 1.0 | 1.4 | 0.7 | 0.6 | 0.7 | 0.6 | 1.2 | 1.6 |
| Sort 3 | 1.0 | 1.1 | 1.3 | 1.6 | 1.2 | 0.6 | 1.0 | 0.8 | 0.5 | 0.9 | 1.0 | 1.5 | 1.0 | 1.8 | 0.6 | 0.5 | 0.7 | 0.5 | 1.1 | 2.0 |
| Sort 4 | 1.0 | 1.1 | 1.3 | 1.8 | 1.1 | 0.5 | 1.0 | 0.9 | 0.4 | 0.9 | 1.0 | 1.5 | 1.0 | 1.8 | 0.6 | 0.4 | 0.6 | 0.4 | 1.0 | 2.3 |
| Sort 5 | 1.0 | 1.1 | 1.2 | 1.9 | 1.2 | 0.5 | 1.0 | 0.8 | 0.4 | 0.9 | 1.1 | 1.6 | 1.0 | 2.0 | 0.5 | 0.3 | 0.5 | 0.4 | 0.9 | 2.4 |

Position Y-1

|  | A | C | E | D | G | F | I | H | K | M | L | N | Q | P | S | R | T | W | V | Y |
|---|---|---|---|---|---|---|---|---|---|---|---|---|---|---|---|---|---|---|---|---|
| Sort 0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Sort 1 | 0.8 | 1.0 | 1.4 | 1.4 | 0.8 | 1.0 | 1.5 | 1.3 | 0.6 | 1.2 | 1.3 | 1.1 | 1.1 | 0.7 | 0.5 | 0.5 | 0.5 | 0.7 | 1.3 | 1.6 |
| Sort 2 | 0.8 | 1.0 | 1.5 | 1.4 | 0.8 | 1.0 | 1.6 | 1.3 | 0.5 | 1.2 | 1.4 | 1.1 | 1.1 | 0.7 | 0.4 | 0.5 | 0.5 | 0.6 | 1.4 | 1.7 |
| Sort 3 | 0.7 | 0.9 | 1.7 | 1.7 | 0.6 | 0.9 | 1.8 | 1.2 | 0.3 | 1.1 | 1.5 | 1.1 | 1.1 | 0.6 | 0.3 | 0.3 | 0.3 | 0.5 | 1.3 | 2.3 |
| Sort 4 | 0.7 | 0.9 | 1.7 | 2.0 | 0.5 | 0.9 | 1.7 | 1.2 | 0.3 | 1.1 | 1.6 | 1.2 | 1.0 | 0.6 | 0.3 | 0.2 | 0.3 | 0.4 | 1.2 | 2.9 |
| Sort 5 | 0.6 | 0.9 | 1.7 | 2.2 | 0.4 | 0.9 | 1.6 | 1.1 | 0.2 | 1.0 | 1.7 | 1.2 | 0.9 | 0.5 | 0.3 | 0.2 | 0.2 | 0.4 | 1.1 | 3.5 |

Position Y+1

|  | A | C | E | D | G | F | I | H | K | M | L | N | Q | P | S | R | T | W | V | Y |
|---|---|---|---|---|---|---|---|---|---|---|---|---|---|---|---|---|---|---|---|---|
| Sort 0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Sort 1 | 1.1 | 1.1 | 1.0 | 1.1 | 1.0 | 1.4 | 0.8 | 1.2 | 0.7 | 1.1 | 0.9 | 0.9 | 1.1 | 0.5 | 1.0 | 0.9 | 0.8 | 1.3 | 0.9 | 1.4 |
| Sort 2 | 1.1 | 1.1 | 1.0 | 1.1 | 1.0 | 1.4 | 0.8 | 1.2 | 0.6 | 1.1 | 0.9 | 0.8 | 1.1 | 0.4 | 1.0 | 0.9 | 0.8 | 1.4 | 0.9 | 1.5 |
| Sort 3 | 1.0 | 1.1 | 0.9 | 1.1 | 0.9 | 1.9 | 0.8 | 1.3 | 0.5 | 1.1 | 0.8 | 0.9 | 1.0 | 0.4 | 0.9 | 0.8 | 0.7 | 1.7 | 0.8 | 1.9 |
| Sort 4 | 0.9 | 1.1 | 0.7 | 1.0 | 0.6 | 2.3 | 0.8 | 1.4 | 0.3 | 1.0 | 0.9 | 0.8 | 1.0 | 0.5 | 0.9 | 0.8 | 0.7 | 1.9 | 0.7 | 2.4 |
| Sort 5 | 0.8 | 1.1 | 0.7 | 0.9 | 0.5 | 2.9 | 0.8 | 1.4 | 0.3 | 1.0 | 0.8 | 0.7 | 0.9 | 0.5 | 0.9 | 0.7 | 0.6 | 2.2 | 0.7 | 2.8 |

Position Y+2

|  | A | C | E | D | G | F | I | H | K | M | L | N | Q | P | S | R | T | W | V | Y |
|---|---|---|---|---|---|---|---|---|---|---|---|---|---|---|---|---|---|---|---|---|
| Sort 0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Sort 1 | 0.9 | 1.1 | 1.1 | 1.1 | 0.7 | 1.2 | 1.1 | 1.0 | 0.7 | 1.1 | 1.1 | 1.1 | 1.0 | 1.0 | 0.8 | 0.8 | 1.0 | 1.1 | 1.2 | 1.4 |
| Sort 2 | 1.0 | 1.2 | 1.1 | 1.1 | 0.7 | 1.2 | 1.2 | 1.0 | 0.6 | 1.1 | 1.1 | 1.1 | 1.0 | 1.0 | 0.8 | 0.8 | 1.0 | 1.1 | 1.2 | 1.4 |
| Sort 3 | 0.9 | 1.2 | 1.2 | 1.1 | 0.6 | 1.4 | 1.3 | 0.9 | 0.5 | 1.2 | 1.1 | 1.2 | 1.0 | 1.0 | 0.7 | 0.7 | 0.9 | 1.2 | 1.3 | 1.7 |
| Sort 4 | 0.9 | 1.3 | 1.1 | 1.2 | 0.5 | 1.4 | 1.4 | 0.9 | 0.4 | 1.3 | 1.2 | 1.2 | 1.0 | 1.0 | 0.7 | 0.6 | 0.8 | 1.2 | 1.4 | 1.9 |
| Sort 5 | 0.8 | 1.4 | 1.1 | 1.1 | 0.5 | 1.5 | 1.4 | 0.9 | 0.3 | 1.4 | 1.3 | 1.1 | 1.0 | 1.0 | 0.6 | 0.5 | 0.7 | 1.3 | 1.4 | 1.9 |

Position Y+3

|  | A | C | E | D | G | F | I | H | K | M | L | N | Q | P | S | R | T | W | V | Y |
|---|---|---|---|---|---|---|---|---|---|---|---|---|---|---|---|---|---|---|---|---|
| Sort 0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Sort 1 | 0.8 | 1.1 | 0.4 | 0.6 | 0.9 | 1.4 | 1.2 | 1.1 | 0.6 | 1.0 | 1.2 | 0.9 | 0.7 | 1.5 | 0.6 | 0.8 | 0.6 | 1.5 | 1.1 | 1.7 |
| Sort 2 | 0.8 | 1.1 | 0.4 | 0.6 | 0.9 | 1.4 | 1.2 | 1.1 | 0.5 | 1.0 | 1.2 | 0.9 | 0.7 | 1.6 | 0.5 | 0.8 | 0.5 | 1.6 | 1.2 | 1.8 |
| Sort 3 | 0.7 | 1.1 | 0.3 | 0.5 | 0.9 | 1.6 | 1.2 | 1.0 | 0.4 | 0.9 | 1.1 | 0.9 | 0.6 | 2.0 | 0.4 | 0.7 | 0.4 | 2.1 | 1.1 | 2.3 |
| Sort 4 | 0.7 | 1.2 | 0.2 | 0.6 | 0.7 | 1.6 | 1.2 | 1.2 | 0.4 | 0.9 | 1.1 | 0.9 | 0.5 | 2.2 | 0.4 | 0.6 | 0.4 | 2.1 | 1.1 | 2.4 |
| Sort 5 | 0.6 | 1.1 | 0.2 | 0.5 | 0.7 | 1.7 | 1.2 | 1.2 | 0.3 | 0.8 | 1.0 | 0.9 | 0.5 | 2.5 | 0.4 | 0.6 | 0.4 | 2.7 | 0.9 | 2.5 |

*Residue Cross-Talk and Model Building*

Position Y-2

Sort 0, Sort 1, Sort 2, Sort 3, Sort 4, Sort 5: Fixed As Aspartate

Position Y-1

| | A | C | E | D | G | F | I | H | K | M | L | N | Q | P | S | R | T | W | V | Y |
|---|---|---|---|---|---|---|---|---|---|---|---|---|---|---|---|---|---|---|---|---|
| Sort 0 | 0.9 | 1.0 | 1.0 | 1.2 | 0.8 | 0.9 | 1.2 | 1.1 | 1.0 | 1.1 | 1.1 | 1.1 | 1.1 | 1.0 | 0.9 | 0.8 | 1.1 | 0.8 | 1.1 | 1.1 |
| Sort 1 | 1.0 | 1.0 | 0.7 | 0.9 | 0.9 | 1.1 | 1.1 | 0.9 | 0.9 | 1.1 | 1.1 | 1.1 | 0.9 | 1.3 | 1.2 | 0.8 | 1.0 | 0.8 | 1.0 | 1.0 |
| Sort 2 | 0.9 | 0.9 | 0.8 | 0.9 | 0.9 | 1.0 | 1.1 | 0.8 | 1.0 | 1.1 | 1.1 | 1.1 | 0.9 | 1.4 | 1.2 | 0.8 | 1.3 | 0.8 | 1.0 | 1.1 |
| Sort 3 | 0.9 | 0.9 | 0.6 | 0.7 | 0.9 | 1.1 | 1.1 | 0.8 | 1.0 | 1.1 | 1.2 | 1.1 | 0.8 | 1.4 | 1.3 | 0.8 | 1.1 | 0.7 | 1.0 | 1.0 |
| Sort 4 | 0.8 | 0.9 | 0.5 | 0.7 | 1.1 | 1.0 | 1.3 | 0.7 | 0.7 | 1.1 | 1.2 | 1.1 | 0.8 | 1.4 | 1.3 | 0.8 | 1.0 | 0.7 | 1.0 | 1.0 |
| Sort 5 | 0.8 | 0.9 | 0.5 | 0.6 | 1.2 | 0.9 | 1.3 | 0.7 | 0.9 | 1.1 | 1.3 | 1.0 | 0.8 | 1.5 | 1.2 | 0.8 | 1.1 | 0.7 | 1.0 | 1.1 |

Position Y+1

| | A | C | E | D | G | F | I | H | K | M | L | N | Q | P | S | R | T | W | V | Y |
|---|---|---|---|---|---|---|---|---|---|---|---|---|---|---|---|---|---|---|---|---|
| Sort 0 | 0.8 | 1.1 | 0.9 | 1.1 | 0.8 | 1.2 | 1.0 | 1.1 | 1.0 | 1.1 | 1.1 | 0.9 | 1.0 | 0.9 | 1.1 | 1.0 | 1.0 | 1.1 | 1.0 | 1.3 |
| Sort 1 | 0.9 | 1.1 | 0.8 | 0.9 | 0.8 | 1.1 | 1.2 | 1.0 | 1.0 | 1.1 | 1.2 | 1.1 | 1.0 | 0.9 | 1.1 | 0.9 | 1.1 | 0.9 | 1.1 | 1.0 |
| Sort 2 | 0.8 | 1.1 | 0.8 | 0.8 | 0.8 | 1.1 | 1.4 | 0.9 | 1.0 | 1.2 | 1.2 | 1.0 | 1.0 | 0.9 | 1.1 | 0.9 | 1.2 | 0.9 | 1.2 | 1.0 |
| Sort 3 | 0.8 | 1.1 | 0.8 | 0.8 | 0.8 | 1.1 | 1.1 | 0.9 | 1.2 | 1.1 | 1.2 | 1.8 | 1.0 | 0.7 | 1.2 | 0.9 | 1.3 | 0.9 | 1.1 | 1.0 |
| Sort 4 | 0.8 | 1.1 | 0.8 | 0.8 | 0.8 | 1.1 | 1.1 | 0.9 | 1.2 | 1.2 | 1.2 | 1.6 | 0.9 | 0.7 | 1.1 | 0.9 | 1.4 | 0.9 | 1.1 | 0.9 |
| Sort 5 | 0.8 | 1.1 | 0.9 | 0.7 | 0.8 | 1.1 | 1.1 | 0.9 | 1.2 | 1.3 | 1.2 | 1.5 | 0.9 | 0.7 | 1.2 | 0.9 | 1.5 | 0.8 | 1.1 | 0.9 |

Position Y+2

| | A | C | E | D | G | F | I | H | K | M | L | N | Q | P | S | R | T | W | V | Y |
|---|---|---|---|---|---|---|---|---|---|---|---|---|---|---|---|---|---|---|---|---|
| Sort 0 | 0.9 | 1.2 | 1.0 | 1.1 | 0.8 | 1.0 | 1.1 | 1.1 | 0.9 | 1.0 | 1.0 | 1.1 | 0.9 | 1.0 | 1.1 | 1.0 | 1.1 | 1.0 | 1.0 | 1.1 |
| Sort 1 | 0.9 | 1.1 | 0.8 | 1.0 | 0.8 | 1.2 | 1.1 | 1.0 | 1.1 | 1.1 | 1.1 | 1.0 | 0.9 | 1.0 | 1.0 | 0.9 | 1.0 | 0.9 | 1.0 | 1.1 |
| Sort 2 | 1.0 | 1.2 | 0.9 | 1.0 | 0.8 | 1.1 | 1.1 | 0.9 | 0.9 | 1.0 | 1.2 | 1.0 | 0.9 | 1.0 | 1.1 | 0.8 | 0.9 | 0.9 | 1.0 | 1.0 |
| Sort 3 | 0.9 | 1.1 | 0.7 | 0.9 | 0.8 | 1.2 | 1.2 | 1.0 | 1.1 | 1.1 | 1.1 | 0.9 | 0.9 | 0.9 | 1.0 | 0.9 | 0.9 | 0.9 | 1.1 | 1.1 |
| Sort 4 | 0.9 | 1.1 | 0.7 | 0.8 | 0.7 | 1.2 | 1.2 | 1.0 | 1.1 | 1.2 | 1.2 | 0.9 | 0.9 | 0.9 | 1.0 | 0.8 | 0.9 | 1.0 | 1.1 | 1.1 |
| Sort 5 | 0.9 | 1.1 | 0.6 | 0.8 | 0.7 | 1.3 | 1.3 | 1.0 | 1.3 | 1.0 | 1.2 | 0.9 | 0.9 | 0.9 | 0.9 | 0.9 | 0.9 | 0.9 | 1.1 | 1.1 |

Position Y+3

| | A | C | E | D | G | F | I | H | K | M | L | N | Q | P | S | R | T | W | V | Y |
|---|---|---|---|---|---|---|---|---|---|---|---|---|---|---|---|---|---|---|---|---|
| Sort 0 | 0.8 | 1.0 | 0.8 | 1.0 | 0.8 | 1.0 | 1.2 | 1.1 | 0.8 | 1.1 | 1.1 | 1.0 | 1.0 | 1.1 | 1.0 | 0.9 | 1.1 | 1.1 | 1.0 | 1.1 |
| Sort 1 | 1.0 | 1.1 | 0.8 | 1.0 | 0.8 | 1.1 | 1.2 | 1.1 | 0.9 | 1.2 | 1.1 | 1.0 | 1.0 | 0.9 | 1.0 | 0.9 | 1.0 | 0.9 | 1.0 | 0.9 |
| Sort 2 | 1.0 | 1.0 | 0.7 | 1.1 | 0.5 | 1.1 | 1.2 | 1.0 | 0.9 | 1.1 | 1.2 | 1.0 | 1.0 | 1.0 | 1.0 | 1.0 | 0.9 | 0.9 | 1.0 | 1.0 |
| Sort 3 | 0.9 | 1.0 | 0.7 | 1.0 | 0.8 | 1.1 | 1.2 | 1.0 | 1.0 | 1.1 | 1.2 | 0.9 | 0.9 | 1.0 | 1.0 | 1.1 | 0.9 | 1.0 | 1.0 | 0.9 |
| Sort 4 | 1.0 | 1.0 | 0.9 | 1.0 | 0.8 | 1.1 | 1.1 | 1.0 | 0.8 | 1.1 | 1.2 | 0.9 | 1.1 | 0.9 | 1.1 | 1.1 | 0.9 | 1.0 | 1.0 | 0.9 |
| Sort 5 | 1.1 | 1.0 | 0.7 | 0.9 | 0.8 | 1.2 | 1.2 | 0.9 | 0.7 | 1.0 | 1.2 | 0.7 | 1.0 | 0.9 | 1.1 | 1.1 | 0.9 | 1.0 | 1.0 | 1.0 |

METHODS FOR GENERATING ENGINEERED ENZYMES

This application is a national phase application under 35 U.S.C. § 371 of International Application No. PCT/US2015/055494, filed Oct. 14, 2015, which claims the benefit of U.S. Provisional Patent Application No. 62/063,836, filed Oct. 14, 2014, the entirety of each of which is incorporated herein by reference.

BACKGROUND OF THE INVENTION

1. Field of the Invention

The present invention relates generally to the field of molecular biology and medicine. More particularly, it concerns methods for generating modified proteases and kinases that display altered and/or improved activity.

2. Description of Related Art

A wide range of disorders involve aberrant protease function, and therapeutic proteases have the potential to treat a variety of diseases. Nonetheless, several technical factors have limited the use of therapeutic proteases. One particular challenge for the development therapeutic protease is that one determine that the therapeutic protease results in a particular catalytic activity, with little or no catalytic activity that would be undesirable. Defining substrate specificity with greater precision will be increasingly necessary as engineered proteases are developed for more sophisticated applications including therapies (Li et al. 2013).

Genetic and biochemical studies have led to the identification and characterization of endogenous convertases such as Kex2 (also known as kexin, peptidase 3.4.21.61) existing in the yeast secretory pathway (Seidah et al. 2002). The Kex2 convertase catalyzes cleavage after two basic residues, especially Lys-Arg, so dibasic sites are generally considered to be classical processing sites in precursors of secreted proteins (Rozan et al. 2004; Rockwell et al. 1997; Rockwell et al. 1998). To the knowledge of the inventors, there has been no comprehensive analysis of the endogenous convertase cleaving patterns (cleaveOme) inside the secretory pathway of a living cell.

Various chemical and biological based approaches, including microarray, phage display and bacterial display, have been developed to characterize protease substrate specificity (Diamond 2007; Scholle et al. 2006; Matthews et al. 1994). CLiPS uses bacterial display of genetically encoded substrate libraries followed by FACS sorting to identify cleaved peptides (Boulware et al. 2006). More recent methods involve mass spectral analysis of either peptide libraries (O'Donoghuel et al. 2012) or endogenously cleaved protein substrates (Dix et al., 2008) during apoptosis.

Yeast cells have been widely used for recombinant protein production, however, proteolytic degradation of the recombinant protein of interest has been a perpetual problem (Sinha et al. 2005). Clearly, there exists a need for improved methods for measuring the specificity of enzymes, such as proteases or kinases, that covalently modify an amino acid or protein substrate. Such improved methods could be particularly useful, e.g., for more effectively engineering a therapeutic protease.

SUMMARY OF THE INVENTION

The present invention, in various aspects, overcomes limitations in the prior art by providing improved methods for generating and/or measuring the activity or specificity of enzymes such as proteases, sortases (convertases), or kinases, that can covalently modify a genetically encoded substrate. In some embodiments, the patterns of the sequences of amino acid or protein substrates that are cleaved by endogenous convertases or proteases (referred to as a "cleaveOme") in cells such as a yeast may be identified, in some embodiments, by methods involving expressing a library of substrates in the cells in combination with next-generation sequencing to identify particular sequences of substrates that are selectively cleaved or covalently modified. These approaches may be used, e.g., to more accurately identify the specific sequences or substrates that are cleaved, cleaved and ligated, or phosphorylated by a wild-type or engineered protease, convertase, or kinase. In some embodiments, a Kex2 knockout yeast (e.g., EBY100$^{Kex2}$) may be used to prevent unwanted cleavage of proteins and peptides.

Provided are methods and vectors for the expression and generation of engineered enzymes that covalently modify a genetically encoded substrate. In some embodiments, the enzyme is a protease. In these embodiments one or more vectors may be introduced into eukaryotic cells, such as yeast (e.g., a Kex2 knockout yeast), that encode a protease (which may or may not be randomized or mutated relative to wild-type) and a substrate amino acid sequence (which may or may not be randomized or mutated). In some embodiments, the protease and the substrate are encoded in a single vector; nonetheless, the protease and substrate may be encoded by separate vectors, if desired. The protease and the substrate may be expressed as a fusion construct comprising an endoplasmic reticulum (ER) targeting sequence and an ER retention sequence. In this way, the protease and the amino acid substrate can be brought together in the confines of the ER, and this approach may, e.g., favorably affect protein folding of the protease and/or increase the likelihood of an interaction between the protease and the substrate by bringing the substrate and protease into closer proximity in the ER. Nonetheless, in some embodiments, it may be desirable to exclude the ER targeting and/or ER retention sequence from the fusion construct comprising the protease and/or the fusion construct comprising the substrate; for example, excluding the ER targeting or ER retention sequence may be useful for identifying proteases that exhibit increased potency or catalytic activity. The substrate may be expressed as a fusion protein comprising a surface expression protein and an epitope tag on separate sides of the substrate sequence. In this way, cleavage events may be detected (e.g., using FACS) based on detection of one or both of the epitopes in the substrate on the surface of the eukaryotic cells (e.g., yeast cells). In some embodiments, a library of randomized substrates in a vector including the cell expression surface protein and the two epitopes may be expressed in eukaryotic cells, such as yeast, to observe endogenous protease activity (cleaveOme). These endogenous cleavage events may be measured using next-generation sequencing. In some embodiments, data indicating background cleavage events may be subtracted from data indicating cleavage events, e.g., obtained by expressing a protease in yeast cells as described above. In this way, the identification of specific cleavage specificity and/or catalytic activity may be significantly improved. These approaches may be particularly useful, e.g., for the identification of wild-type proteases and/or generation of mutant proteases that may be used therapeutically or to treat a disease, particularly considering that off-target cleavage events would generally be undesirable in these situations. Additionally, these approaches may be useful to identify proteases with a particular specificity and/or catalytic activity that may be used in a laboratory or industrial setting such as, e.g., TEV proteases and similar proteases are commonly used in the production of therapeutic proteins, such as antibodies, fusion proteins, immunotoxins, etc.

Some aspects of the present invention relate to methods for producing a polypeptide or protein (e.g., a recombinant polypeptide) in a Kex2 knockout yeast, wherein the polypeptide or protein comprises a Kex2 cleavable sequence (e.g., as shown in Table 1 below). As shown in the below examples, the endogeneous convertase cleaveOme in the yeast secretory pathway was mapped, revealing the major cleavage patterns K/RR and LXXR (SEQ ID NO:54). These patterns were verified to be due to Kex2 cleavage after comparison to a newly generated Kex2 knockout strain (EBY100$^{Kex2-}$). These results demonstrate that Kex2 is the major endogenous protease in the yeast secretory pathway. The YESS method was also successfully applied to profile the sequence specificity of the wild-type and an engineered variant of the tobacco etch mosaic virus protease.

TABLE 1

The analysis of top 20 peptide substrates of the sorted library in the EBY100 and EBY100$^{Kex2-}$ strains.

| Substrate | SEQ ID NO: | EBY100 | EBY100$^{Kex2-}$ |
|---|---|---|---|
| ARKPA | 33 | X | X |
| GSFRP | 34 | X | X |
| NAFSH | 35 | X | X |
| ALARR | 36 | ✓ | X |
| LRPRA | 37 | ✓ | X |
| ALSRR | 38 | ✓ | X |
| RLRPR | 39 | ✓ | X |
| RLLPR | 40 | ✓ | X |
| YPVCV | 52 | X | X |
| RLSRR | 41 | ✓ | X |
| RLTPR | 31 | ✓ | X |
| PLLPR | 42 | ✓ | X |
| PLLRR | 43 | ✓ | X |
| PLRPR | 44 | ✓ | X |
| SPAWR | 53 | X | X |
| RLAPR | 45 | ✓ | X |
| ALLPR | 46 | ✓ | X |
| PLLAR | 47 | ✓ | X |
| PLVPR | 48 | ✓ | X |
| SLRRR | 49 | ✓ | X |

Some aspects of the present invention relate to methods of generating an engineered convertase (sortase). Generally, two fusion proteins are expressed in a eukaryotic cell such as a yeast: a first fusion protein comprising an epitope tag and a cleavage sequence, and a second fusion protein containing a ligation sequence and a second epitope tag. In some embodiments, the yeast is a Kex2 knockout yeast. Either the first fusion protein or the second protein further comprises a cell surface expression sequence. Thus, if a convertase cleaves and ligates the cleavage sequence with the ligation sequence, then the first and second epitope tag will both be expressed on the cell, such as a yeast, and can be detected, e.g., using FACS. Part or all of the cleavage sequence and/or the ligation sequence may be randomized. In some embodiments, the endogenous activity of sortases in a cell, such as a yeast, may be measured by expressing the first and second fusion proteins in the cell, separating cells based on ligation of the two sequences, and then sequencing the cleavage and ligation sequences, e.g., using next generation sequencing. In some preferred embodiments, the first and second fusion proteins are encoded by a single vector. Nonetheless, in some embodiments, the first and second fusion proteins may be expressed in separate vectors. In some embodiments, the vector may encode fusion proteins, e.g., as shown in FIG. 8 or FIG. 9. In some embodiments, a negative control plasmid construct and/or a positive control plasmid construct may be used as shown in FIGS. 5A-B. In some embodiments a convertase may also be expressed in the cell. The convertase may be a wild type or an engineered convertase, and a portion of the convertase may have been randomized. In some embodiments, the convertase and the first and second fusion proteins are encoded in a single vector. In other embodiments, the convertase, first fusion protein, and second fusion protein are encoded by more than one vector; for example, in some embodiments, the convertase is encoded by a first vector and the first and second fusion proteins are encoded by a second vector. The convertase, first fusion protein, and second fusion protein may each further comprise an ER targeting and ER retention sequence. Inclusion of the ER targeting and ER retention sequences may promote interactions between the convertase, the first fusion protein, and the second fusion protein in the confines of the ER, and/or the convertase, first fusion protein, and second fusion protein may benefit from the improved folding environment of the ER. In some embodiments, the activity or specificity of a sortase may be measured by randomizing a portion of the cleavage sequence or the ligation sequence, measuring the activity of the convertase as described above, sequencing the cleavage sequences and the ligation sequences, and then subtracting the endogenous cleavage and ligation activity present in the cell, such as yeast, measured as described above. Engineered convertases may be used, e.g., in the production of antibodies or ligation of various proteins to molecular probes, nucleic acids, glycans and solid supports.

Yet another aspect of the present invention relates to detecting the kinase activity in a eukaryotic cell, such as a yeast (e.g., a Kex2 knockout yeast). A vector expressing a first fusion protein comprising a peptide sequence and cell surface expression sequence may be expressed in the cell. Then, the presence or absence of phosphorylation of an amino acid in the peptide may be detected, e.g., using FACS, based on the presence or absence of the binding of an antibody that selectively recognizes a phosphorylated amino acid. As would be appreciated by one of skill in the art, several antibodies that selectively recognize phosphorylated amino acids (e.g., phosphor-tyrosine, etc.) are commercially available. The first fusion protein may further comprise an ER targeting and ER retention sequence. In some embodiments the peptide sequence is at least partially randomized, and the peptide sequences are sequenced using next-generation sequencing. In this way, the endogenous kinase activity in a cell may be measured. In some embodiments, a wild-type or engineered kinase may also be expressed in the cell, e.g., in the same vector as the first fusion protein or a different vector. In some embodiments, a portion of the kinase is randomized. The kinase may further comprise an ER targeting and ER retention sequence. In this way, when the kinase and the first fusion protein each comprise an ER targeting and ER retention sequence, the kinase and first fusion protein may be brought into closer proximity in the ER and/or benefit from the improved folding environment of the ER. In some embodiments, the specificity or activity of a kinase may be measured by expressing the kinase in eukaryotic cells with the first fusion protein, sequencing the peptides encoded by the first fusion protein, e.g., via next generation sequencing, and then subtracting data from the sequenced data representing endogenous kinase activity in the eukaryotic cells or yeast cells.

As shown in the below examples, methods involving the use of both Yeast Endoplasmic Reticulum Sequestration Screening (YESS) and next-generation sequencing (NextGen) has been used to provide the first comprehensive cleaveOme (endogeneous protease cleavage specificity) mapping of the yeast secretory pathway. This cleaveOme was then used to support a thorough profiling of the substrate specificity of the wild-type and an engineered tobacco etch mosaic virus protease (TEV-P).

As further shown in the below examples, the inventors have combined yeast endoplasmic reticulum (ER) sequestration screening (YESS) technology with NextGen sequencing (see FIGS. 1A-B) and a comparative sequence analysis to profile protease specificity using a large number of possible sequences in a single experiment. In this approach, the YESS reporter substrate fusion construct included an Aga2 protein, the Flag antibody epitope sequence, a randomized putative substrate sequence, the HA epitope and an ER retention signal peptide, in that order. The N-terminal Aga2 sequence can ensure that following transit through the ER and secretion, the substrate/product is covalently attached to the outer surface. Cells were probed simultaneously with anti-FLAG and anti-HA antibodies conjugated to phycoerythrin (PE) and fluorescein (FITC), respectively. Cleavage was detected via two-dimensional FACS analysis by monitoring the ratio of PE to FITC fluorescence. A high amount of both signals indicated a lack of cleavage, while high PE and low FITC signals indicates cleavage at the substrate site. After FACS-based sorting and isolation, the cleaved sequences were identified by next generation DNA sequencing (NextGen) followed by a comparative sequence analysis to deconvolute cleavage patterns.

An aspect of the present invention relates to a method for measuring the activity of an enzyme in a eukaryotic cell, comprising: (a) expressing in each of a plurality of eukaryotic cells: (i) a first fusion protein comprising an ER targeting sequence, an enzyme, and an ER retention sequence; and (ii) a vector encoding a first peptide; (b) separating or purifying said eukaryotic cells; and (c) sequencing a plurality of said first peptides; wherein the enzyme is a protease, a kinase, or a convertase (sortase); wherein if the enzyme is a protease, then: (ia) the vector encodes a second fusion protein comprising in an N- to C-direction: an endoplasmic reticulum (ER) targeting sequence, a surface expression sequence, a first epitope tag sequence, the first peptide sequence, a second epitope tag sequence, and a endoplasmic reticulum (ER) retention sequence; (ib) the endoplasmic reticulum (ER) targeting sequence and the endoplasmic reticulum (ER) retention sequence, the surface expression sequence, the first epitope tag sequence, the first peptide sequence, and the second epitope tag sequence are expressed as a fusion protein; and (ic) said separating or purifying comprises separating cells based on the presence or absence of expression of the first epitope tag and the second epitope tag on the surface of the eukaryotic cells; wherein if the enzyme is a kinase, then: (iia) the vector encodes a second fusion protein comprising: an endoplasmic reticulum (ER) targeting sequence, a surface expression sequence, the first peptide sequence, and a endoplasmic reticulum (ER) retention sequence; and (iib) said separating comprises separating cells based on the presence or absence of phosphorylation of at least one amino acid of the first peptide on the surface of the eukaryotic cells; wherein if the enzyme is a convertase (sortase), then: (iiia) the vector encodes a second fusion protein and a third fusion protein, wherein the second fusion protein comprises an endoplasmic reticulum (ER) targeting sequence and a endoplasmic reticulum (ER) retention sequence, a surface expression sequence, the first peptide sequence, and a first epitope tag; and wherein the third fusion protein comprises a second peptide sequence and a second epitope tag; and (iiib) said separating comprises separating cells based on the presence or absence of expression of the first epitope tag and the second epitope tag on the surface of the eukaryotic cells; wherein the first peptide sequence is at least partially randomized or a plurality of different first peptide sequences are encoded by each of said vectors. In some embodiments, the enzyme is a convertase (sortase), and wherein the second fusion protein comprises in an N- to C-direction: the endoplasmic reticulum (ER) targeting sequence, the surface expression sequence, the first peptide sequence, the first epitope tag, and the endoplasmic reticulum (ER) retention sequence; and wherein the third fusion protein comprises in an N- to C-direction: the second peptide sequence and the second epitope tag. The first peptide sequence may be a sortase sorting sequence, such as, e.g., LPTEG (SEQ ID NO:13). The second peptide sequence may be a di-glycine amino terminus or a tri-glycine amino terminus. In some embodiments, the enzyme is a kinase, and wherein the vector encodes a second fusion protein comprises in an N- to C-direction: an endoplasmic reticulum (ER) targeting sequence, a surface expression sequence, the first peptide sequence, and a endoplasmic reticulum (ER) retention sequence. The eukaryotic cell may be a yeast cell (e.g., a Kex2 knockout yeast cell). In some embodiments, said sequencing comprises next-generation sequencing. The next-generation sequencing may comprise single-molecule real-time sequencing, an ion semiconductor method, a pyrosequencing method, a sequencing by synthesis method, or a sequencing by ligation method. The method may further comprise analyzing data from said sequencing with a computer. For example, said analyzing may comprises excluding sequences comprising a stop codon. The analyzing may comprise applying a specificity score algorithm to data from said sequencing; wherein said specificity score algorithm comprises assigning a positive specificity score or a negative specificity score to locations on the first peptide sequence. The analyzing may comprise fixing one or more individual positions of the first peptide sequence as an individual amino acid and applying a specificity score algorithm to data for the remaining from said sequencing; wherein said specificity score algorithm comprises assigning a positive specificity score or a negative specificity score to locations of the first peptide sequence. In some embodiments, the first peptide is a selection substrate peptide sequence and the second peptide is a counterselection substrate peptide sequence. In some embodiments, said endoplasmic reticulum (ER) targeting sequence encoded in the vector is comprised in said surface expression sequence in the vector. The surface expression sequence may be Aga2. The method may further comprise sequencing the first peptide in the plurality of eukaryotic cells both before and after step (b). The method may comprise subtracting sequencing data of said first peptide obtained before step (b) from sequencing data of said first peptide obtained after step (b). In some embodiments, step (b) comprises repeated separations or multiple rounds of separation. In some embodiments, step (b) comprises multiple rounds of FACS separation and expansion or culture of the eukaryotic cells. The method may further comprise repeating steps (a) and (b). In some embodiments, the method comprises repeated FACS separation and culture of the eukaryotic cells. In some embodiments, the first peptide may be less than 20 amino acids in length, less than 10 amino acids in length, or 4, 5, 6, 7, or 8 amino acids in length. The first peptide may comprise 1, 2, 3, 4, 5, or 6 randomized amino acids. The first peptide may be comprised in a protein, wherein the protein is encoded by the vector. In some embodiments, said separating comprises fluorescence-activated cell sorting (FACS). In some embodiments, the enzyme is a kinase and wherein step (iib) comprises FACS separation of cells via an antibody that selectively binds a phosphorylated amino acid (e.g., a phosphorylated tyrosine). The method may further comprise transfecting said eukaryotic cells with a vector encoding an enzyme. The enzyme may be a protease such as, e.g., a human protease. In some embodiments, the enzyme is a TEV-protease, rTPA, a coagulation factor, factor 7, factor 9, human trypsin, a granzyme, a caspase, trypsin, human granzyme K, or a human caspase. The enzyme may be a convertase (sortase) such as, e.g., a gram-positive bacteria convertase, a gram-negative bacteria (e.g., *Shewanella putrefaciens*) convertase, or an Archaea (e.g., *Methanobacterium thermoautotrophicum*) convertase. The enzyme may be a sortase A. In some embodiments, the enzyme is a kinase such as, e.g., a human kinase. The enzyme may be a tyrosine kinase. In some embodiments, the enzyme is a wild-type enzyme. In some embodiments, the enzyme is mutated relative to wild-type. In some embodiments, a plurality of the cells have been exposed to a test compound. The test compound may be a protease inhibitor or a kinase inhibitor. In some embodiments, a first promoter controls expression of the first fusion protein, wherein the first promoter is expressable in yeast. The first promoter may be Gal1 or Gal10. The endoplasmic reticulum (ER) targeting sequence may be MQLLRCFSIFSVIASVLA (SEQ ID NO:3). The endoplasmic reticulum (ER) retention sequence may be FEHDEL (SEQ ID NO:4), KDEL (SEQ ID NO:5), HDEL (SEQ ID NO:6), or RDEL (SEQ ID NO:7).

Another aspect of the present invention relates to a method of measuring the activity or specificity of a protease, comprising: (a) expressing a in a plurality of eukaryotic cells a vector encoding: (i) a first fusion protein comprising the protease, a first endoplasmic reticulum (ER) targeting sequence, and a first endoplasmic reticulum (ER) retention sequence; and (ii) a second fusion protein comprising a second endoplasmic reticulum (ER) targeting sequence and a second endoplasmic reticulum (ER) retention sequence, a surface expression sequence, a first epitope tag sequence, a first peptide sequence, and a second epitope tag sequence; (b) purifying or separating the cells based on the presence or absence of a first antibody that selectively binds the first epitope tag sequence and a second antibody that selectively binds the second epitope tag sequence; (c) sequencing the first peptide sequences after step (b) to produce a dataset; and (d) subtracting or eliminating endogenous cleavage events (cleaveOme) in the eukaryotic cells from the dataset. The cleaveOme may determined by a method of the present invention. The cells may be yeast cells (e.g., Kex2 knockout yeast cells). The antibody may be labeled with a fluorophore. The purifying or separating may comprise or consist of fluorescence activated cell sorting (FACS). The method may further comprise randomizing one or more amino acids in the protease. The method may comprise further characterizing the protease. The protease may be a human protease. The protease may be a TEV-protease, rTPA, a coagulation factor, factor 7, factor 9, human trypsin, a granzyme, a caspase, trypsin, human granzyme K, or a human caspase. The protease may be a therapeutic protease. The enzyme may be a wild-type enzyme. The enzyme may be mutated relative to wild-type. In some embodiments, step (d) further comprises excluding sequences including lysine and/or arginine. In some embodiments, at least a portion of the protease is randomized. In some embodiments, the method is further defined as a method of generating an engineered protease, wherein step (b) is repeated. In some embodiments, the first endoplasmic reticulum (ER) targeting sequence and the second endoplasmic reticulum (ER) targeting sequence are MQLLRCFSIFSVIASVLA (SEQ ID NO:3). In some embodiments, the first endoplasmic reticulum (ER) retention sequence and the second endoplasmic reticulum (ER) retention sequence are FEHDEL (SEQ ID NO:4), KDEL (SEQ ID NO:5), HDEL (SEQ ID NO:6), or RDEL (SEQ ID NO:7).

Yet another aspect of the present invention relates to a method of measuring the activity or specificity of a convertase (sortase), comprising: (a) expressing a in a plurality of eukaryotic cells a vector encoding: (i) a first fusion protein comprising the convertase, a first endoplasmic reticulum (ER) targeting sequence, and a first endoplasmic reticulum (ER) retention sequence; and (ii) a second fusion protein comprising a second endoplasmic reticulum (ER) targeting sequence and a second endoplasmic reticulum (ER) retention sequence, a surface expression sequence, a first epitope tag sequence, a first peptide sequence, and a second epitope tag sequence; (b) purifying or separating the cells based on the presence or absence of a first antibody that selectively binds the first epitope tag sequence and a second antibody that selectively binds the second epitope tag sequence; (c) sequencing the first peptide sequences after step (b) to produce a dataset; and (d) subtracting or eliminating endogenous convertase activity in the eukaryotic cells from the dataset. The first peptide sequence may be a sortase sorting sequence such as, e.g., LPTEG (SEQ ID NO:13). The second peptide sequence may be a di-glycine amino terminus or a tri-glycine amino terminus. The endogenous convertase activity may be determined by the method of the present invention. The cells may be yeast cells (e.g., Kex2 knockout yeast cells). The antibody may be labeled with a fluorophore. The purifying or separating may comprise or consists of fluorescence activated cell sorting (FACS). The method may further comprising randomizing one or more amino acids in the convertase. The method may comprise further characterizing the convertase. The convertase a gram-positive bacteria convertase or a gram-negative bacteria convertase. In some embodiments, the convertase is sortase A. The convertase may be a wild-type convertase. In some embodiments, the convertase is mutated relative to wild-type. In some embodiments, at least a portion of the convertase is randomized. In some embodiments, the method is further defined as a method of generating an engineered convertase, wherein step (b) is repeated. In some embodiments, the first endoplasmic reticulum (ER) targeting sequence and the second endoplasmic reticulum (ER) targeting sequence are MQLLRCFSIFSVIASVLA (SEQ ID NO:3). In some embodiments, the first endoplasmic reticulum (ER) retention sequence and the second endoplasmic reticulum (ER) retention sequence are FEHDEL (SEQ ID NO:4), KDEL (SEQ ID NO:5), HDEL (SEQ ID NO:6), or RDEL (SEQ ID NO:7).

Another aspect of the present invention relates to a method of measuring the activity or specificity of a kinase, comprising: (a) expressing a in a plurality of eukaryotic cells a vector encoding an endoplasmic reticulum (ER) targeting sequence and a endoplasmic reticulum (ER) retention sequence, a surface expression sequence and the first peptide sequence; (b) purifying or separating the cells based on the presence or absence of a first antibody that selectively binds a phosphorylated amino acid; (c) sequencing the first peptide sequences after step (b) to produce a dataset; and (d) subtracting or eliminating endogenous kinase activity in the eukaryotic cells from the dataset. The endogenous kinase activity may be determined by a method of the present invention. The cells may be yeast cells (e.g., Kex2 knockout yeast cells). The antibody may be labeled with a fluorophore. The purifying or separating may comprise or consists of fluorescence activated cell sorting (FACS). The method may further comprising randomizing one or more amino acids in the kinase. The method may comprise further characterizing the kinase. The kinase may be a human kinase. In some embodiments, the kinase is a tyrosine kinase. The kinase may be a wild-type kinase. In some embodiments, the kinase is mutated relative to wild-type. In some embodiments, at least a portion of the kinase is randomized. In some embodiments, the method is further defined as a method of generating an engineered kinase, wherein step (b) is repeated. In some embodiments, the first endoplasmic reticulum (ER) targeting sequence and the second endoplasmic reticulum (ER) targeting sequence are MQLLRCFSIFSVIASVLA (SEQ ID NO:3). In some embodiments, the first endoplasmic reticulum (ER) retention sequence and the second endoplasmic reticulum (ER) retention sequence are FEHDEL (SEQ ID NO:4), KDEL (SEQ ID NO:5), HDEL (SEQ ID NO:6), or RDEL (SEQ ID NO:7).

Yet another aspect of the present invention relates to a method for producing a polypeptide, comprising expressing the polypeptide in a Kex2(−/−) knockout yeast, wherein the polypeptide contains a sequence of Table 1. In some embodiment, the sequence is ALARR (SEQ ID NO:36), LRPRA (SEQ ID NO:37), ALSRR (SEQ ID NO:38), RLRPR (SEQ ID NO:39), RLLPR (SEQ ID NO:40), RLSRR (SEQ ID NO:41), RLTPR (SEQ ID NO:31), PLLPR (SEQ ID NO:42), PLLRR (SEQ ID NO:43), PLRPR (SEQ ID NO:44), RLAPR (SEQ ID NO:45), ALLPR (SEQ ID NO:46), PLLAR (SEQ ID NO:47), PLVPR (SEQ ID NO:48), or SLRRR (SEQ ID NO:49). The polypeptide may comprise or consist of an antibody, an antibody fragment, an immunotoxin, an scfv, or an enzyme. In some embodiments, the polypeptide is a humanized antibody.

Another aspect of the present invention relates to a polypeptide produced by a method of the present invention, e.g., as described above or herein. The polypeptide may be comprised in a pharmaceutical composition that further comprises an excipient.

In some embodiments, the endogenous activity of proteases (cleaveOme), kinases, or sortases may be evaluated in a diseased cell, such as a cancer, and compared to the levels of activity in a healthy cell. In this way, one may be able to determine if the diseased cell exhibits altered activity of an enzyme (e.g., kinase) and may be more effectively treated with an anti-cancer therapy (e.g., a particular kinase inhibitor). In some embodiments, methods provided herein may be used to measure the effects a compound on kinase activity; for example, if the compound is a kinase inhibitor, one may use methods provided herein to evaluate cleavage of substrates in the presence or absence of the compound to determine the effect(s) of the kinase inhibitor. Such approaches may be particularly useful for personalizing a therapy (e.g., to determine if a particular kinase inhibitor should be administered to a subject to treat a disease such as a cancer) or evaluating the specificity of an engineered or mutant protease or kinase.

YESS sequencing may employ expression of proteins in yeast for high-throughput screening. YESS may used to identify evolved proteases or protein kinases having altered substrate specificity or potency, and yeast cells displaying desirable protease or kinase variants can be separated, e.g., using fluorescence activated cell sorting (FACS). YESS may involve the targeted interaction of the protease or kinase variant with substrates in the yeast endoplasmic reticulum (ER). Following reaction with protease or kinase in the ER, substrate cleavage or phosphorylation products can be directed to display the yeast surface then detected with labeled antibodies. This method may be used, e.g., to alter the substrate specificity or catalytic efficiency of a protease, e.g., such as altering the P1 substrate specificity of a TEV protease. For example, two engineered TEV proteases have been isolated that recognize and cleave ENLYFES (SEQ ID NO:1) and ENLYFHS (SEQ ID NO:2) substrates, exhibiting 5000-fold and 1100-fold increases in activity with these substrates, respectively, compared to the wild-type TEV protease.

YESS may involve a nucleic acid vector, wherein the nucleic acid encodes: (i) a first endoplasmic reticulum (ER) targeting sequence and a first endoplasmic reticulum (ER) retention sequence; (ii) a surface expression sequence; (iii) a first peptide sequence; (iv) a first epitope tag sequence; (v) a second peptide sequence; (vi) a second epitope tag sequence; (vii) an enzyme, wherein the enzyme is a protease or a kinase; and (viii) a second endoplasmic reticulum (ER) targeting sequence and a second endoplasmic reticulum (ER) retention sequence; wherein (i), (ii), (iii), (iv), (v), and (vi) are expressed as a first fusion construct, wherein the first endoplasmic reticulum targeting sequence is located at or near the N-terminus of the first fusion construct and wherein the first endoplasmic reticulum retention sequence is located at or near the C-terminus of the first fusion construct; and wherein (vii) and (viii) are expressed as a second fusion construct, wherein the second endoplasmic reticulum targeting sequence is located at or near the N-terminus of the second fusion construct, and wherein the second endoplasmic reticulum retention sequence is located at or near the C-terminus of the second fusion construct. In some embodiments, the enzyme is a sortase or a glycosyltransferase. In some embodiments, (i), (ii), (iii), (iv), (v), and (vi) are operably linked to a first promoter, and (vii) and (viii) may be operably linked to a second promoter. The first peptide sequence may be a counter selection substrate. At least a portion of the first peptide may be randomized. The first peptide may be the native substrate of the protease or kinase. In some embodiments, the first peptide is a sequence that is unrelated to the native substrate or shares no or essentially no sequence identity with the native substrate. The first peptide may be a mutated native substrate of the protease or kinase. The first peptide may have 1, 2, 3, 4, 5 or more mutations, such as substitution mutations, additions, or deletions as compared to the native substrate of the protease or kinase but otherwise shares complete amino acid sequence with the protease or kinase.

In some embodiments, the second peptide sequence is a selection substrate. At least a portion of the second peptide may be randomized. The second peptide may be the native substrate of the protease or kinase. The first peptide may be a mutated native substrate of the protease or kinase. The first peptide may have 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, additions, or deletions as compared to the native substrate of the protease or kinase but otherwise shares complete amino acid sequence with the protease or kinase. In some embodiments, a first promoter controls expression of the first fusion protein, and a second promoter controls expression of the second fusion protein. The first promoter and the second promoter may be expressible in yeast. In some embodiments, the first promoter is Gal1 or Gal10. In some embodiments, the second promoter is Gal1 and Gal10. The nucleic acid may comprise one or more enhancers. The nucleic may also encode a third epitope tag sequence. The third epitope tag sequence may be a hemagglutinin epitope tag. The third epitope tag may be comprised in the first fusion construct. The third epitope tag may be located between (ii) and (iii). The protease or kinase may be a human protease or kinase. The protease may be a TEV-protease, rTPA, human trypsin, a granzyme, a caspase, trypsin, human granzyme K, or a human caspase. The kinase may be a tyrosine kinase. At least a portion of the protease or kinase may be randomized. The first endoplasmic reticulum (ER) targeting sequence and the second endoplasmic reticulum (ER) targeting sequence may be MQLLRCFSIFSVIASVLA (SEQ ID NO:3). The first endoplasmic reticulum (ER) retention sequence and the second endoplasmic reticulum (ER) retention sequence may be FEHDEL (SEQ ID NO:4), KDEL (SEQ ID NO:5), HDEL (SEQ ID NO:6), or RDEL (SEQ ID NO:7).

In some embodiments, the nucleic acid may comprise one or more of the following: (1) the first and/or second ER retention sequences may be removed from the nucleic acid, (2) a stronger promoter may be used for expression of the first and second peptide sequences and/or a weaker promoter may be used to express the protease or kinase, and/or (3) multiple copies of the first and second peptide sequence may be expressed in the nucleic acid vector. To achieve differential expression levels of the first and second peptide sequences versus the protease or kinase, the first and second promoters may be variants of the same promoter, e.g., a Gal1 promoter and a mutant Gal1 promoter that is more or less active than the wild-type Gal1 promoter. Alternatively, the first and second promoters may be different promoters, e.g., a Gal1 promoter and a Gal10 promoter. In either case, the first and second promoters may have relative strengths that are different, e.g., between at least about 1.5- and 100-fold different, between about 2- and 20-fold different, between about 10- and 50-fold different, and any ranges derivable therein.

YESS may comprise expressing the nucleic acid vector in a eukaryotic cell such as, e.g., a yeast cell. The nucleic acid may be expressed in another eukaryotic cell such as, e.g., a mammalian cell. In some embodiments, the nucleic acid is expressed in a diseased cell, such as a cancer cell. In some embodiments, the cell may lack (e.g., via knockout) of the gene such as, e.g., a gene encoding a kinase.

The YESS method may be used for producing a protease, a kinase, a glycosyltransferase, or a sortase, comprising: (i) expressing one or more nucleic acid of the present invention in a plurality of cells; and (ii) purifying or separating cells based on the presence or absence of an antibody that selectively binds the first epitope tag sequence or the second epitope tag sequence. In some embodiments, the eukaryotic cell is a yeast cell. Nonetheless, it is anticipated that other eukaryotic cells, such as mammalian cells, human cells, or human cancerous cells may be used in certain embodiments. The nucleic acid may further comprise a third epitope tag. The method may further comprise purifying cells that express the third epitope tag. The antibody may be labeled with a fluorophore. The purifying or separating may comprise FACS. The method may comprise isolating the nucleic acid. The method may comprise further randomizing the nucleic acid. The method may comprise further characterizing the protease or kinase encoded by the nucleic acid. The method may comprise repeating steps (i) and (ii).

In some aspects, the methods may be used to generate a modified protease or kinase with increased potency or efficiency as compared to a wild-type protease or kinase. For example, in order to identify a protease or kinase with increased efficiency or potency, one or more of the following strategies may be employed: (1) the first and/or second ER retention sequences may be removed from the nucleic acid, (2) a stronger promoter may be used for expression of the first and second peptide sequences and/or a weaker promoter may be used to express the protease or kinase, and/or (3) multiple copies of the first and second peptide sequence may be expressed in the nucleic acid vector. Thus, one may modify the methods to insure that only a protease or kinase with only at least a certain level of activity is identified as a result of the methods. These approaches may be particularly suited for subsequent rounds of evolution or when steps (i)-(iii) are repeated. These methods may also be used to generate a modified sortase or glycosyltransferase that displays a modified or increased potency or efficiency as compared to a wild-type sortase or a wild-type glycosyltransferase, respectively.

Another aspect of the present invention relates to a protease or kinase produced by a method of the present invention. The protease or kinase may be comprised in a pharmaceutical formulation. In some embodiments, the protease is an rTPA protease. In some embodiments, the kinase is a rAbl tyrosine kinase.

Unless defined otherwise, all technical and scientific terms used herein have the meaning commonly understood by one of ordinary skill in the art relevant to the invention. The definitions below supplement those in the art and are directed to the embodiments described in the current application.

As used herein, an "amino molecule" or "amino acid" refers to any amino acid, amino acid derivative, or amino acid mimic as would be known to one of ordinary skill in the art. In certain embodiments, the residues of the protease or proteinaceous molecule are sequential, without any non-amino molecule interrupting the sequence of amino molecule residues. In other embodiments, the sequence may comprise one or more non-amino molecule moieties. In particular embodiments, the sequence of residues of the protease or proteinaceous molecule may be interrupted by one or more non-amino molecule moieties.

The term "selection substrate sequence" as used herein refers to an amino acid sequence in a protein or peptide that may be used to select, identify, or screen for enzymes that can cleave (e.g., proteases or convertases) or modify (e.g., phosphorylated by a kinase) the amino acid sequence. The selection substrate sequence may be, e.g., 2, 3, 4, 5, 6, 7, 8, or 9 aa in length. The selection substrate sequence may be at least partially randomized, or particular amino acid sequences may be chosen and used. As described herein, based on the location of the selection substrate sequence in a vector, cleavage or modification of the selection substrate sequence may be detected, e.g., using FACS to detect the presence or absence of expression of an epitopes on the surface of a eukaryotic cell expressing the vector.

The term "counterselection substrate sequence" as used herein refers to an amino acid sequence in a protein or peptide that may be used to exclude enzymes that can cleave (e.g., proteases or convertases) the amino acid sequence. The counterselection substrate sequence may be, e.g., 2, 3, 4, 5, 6, 7, 8, or 9 aa in length. The selection substrate sequence may be at least partially randomized, or particular amino acid sequences may be chosen and used. As described herein, based on the location of the selection substrate sequence in a vector, cells expressing an enzyme that causes cleavage or modification of the counterselection substrate sequence may be excluded from cells that are purified, e.g., using FACS. Cleavage or modification of the counterselection substrate sequence may be used to exclude enzymes that exhibit undesirable or promiscuous activity. For example, cleavage of a counterselection substrate sequence by an enzyme may result in removal one or more epitopes from a fusion protein that can be expressed on the cell of a eukaryotic cell; in this way, either the lack of any detectable signal or the detection of an undesirable cleavage event (e.g., using FACS) may be used to exclude cells that express the enzyme having the undesirable activity.

The term "antibody" is used herein in the broadest sense and specifically encompasses at least monoclonal antibodies, polyclonal antibodies, multi-specific antibodies (e.g., bispecific antibodies), naturally polyspecific antibodies, chimeric antibodies, humanized antibodies, human antibodies, and antibody fragments. An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon, and mu constant region genes, as well as myriad immunoglobulin variable region genes.

"Antibody fragments" comprise a portion of an intact antibody, for example, one or more portions of the antigen-binding region thereof. Examples of antibody fragments include Fab, Fab', F(ab')2, and Fv fragments, diabodies, linear antibodies, single-chain antibodies, and multi-specific antibodies formed from intact antibodies and antibody fragments.

An "intact antibody" is one comprising full-length heavy- and light-chains and an Fc region. An intact antibody is also referred to as a "full-length, heterodimeric" antibody or immunoglobulin.

The term "variable" refers to the portions of the immunoglobulin domains that exhibit variability in their sequence and that are involved in determining the specificity and binding affinity of a particular antibody.

As used herein, the term "complementary nucleotide sequence" refers to a sequence of nucleotides in a single-stranded molecule of DNA or RNA that is sufficiently complementary to that on another single strand to specifically hybridize to it with consequent hydrogen bonding.

An "expression vector" is intended to be any nucleotide molecule used to transport genetic information.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

(FIGS. 3A-C) Identification of enrichment of Arg (R) residues following Lys (K) at positions II-IV. (FIGS. 3D-F) Identification of enrichment of one or more Arg (R) residues following Arg (R) at positions II-IV. (FIGS. 3G-H) Identification of enrichment for Arg (R) in the third position following Leu (L) in positions I and II and (FIG. 3F, FIG. 3I) identification of corresponding enrichment of Leu (L) in the third position preceding Arg (R) in positions IV and V.

(FIG. 5A) Negative and (FIG. 5B) positive control plasmid constructs for analysis of sortases.

(FIG. 6A) Negative and (FIG. 6B) positive control FACS signals. The HA-FITC signal is on the x-axis and FLAG-PE signal is on the y-axis. Histograms of the individual HA-FITC and FLAG-PE fluorescence counts are to the right of the respective plots.

FIGS. 12A-B: Sequence analysis. FIG. 12A, PhosphoSitePlus lists 127 known substrates of human ABL1. The most conserved residue is a proline at the Y+3 position. FIG. 12B, Enrichment data from YESS screening and HTP Sequencing. MiSeq produced approximately 10 million reads of substrate genes, barcoded by sorting round. Amino acid frequencies were normalized to the unsorted library frequency to calculate an enrichment for each amino acid-position combination. While there is agreement between known substrates and the enrichment data, there are key differences, for instance the enrichment of aromatics at the Y+1, Y+2, and Y+3 positions.

FIG. 13: Cross-talk between substrate residues. When only a subset of recovered sequences were examined with a given amino acid fixed, it was observed that patterns emerge, which are different from the overall enrichment pattern. This indicates cross-talk between substrate residues, which cannot be represented or accounted for in one-dimensional sequence logos.

DESCRIPTION OF ILLUSTRATIVE EMBODIMENTS

Figure 1A:
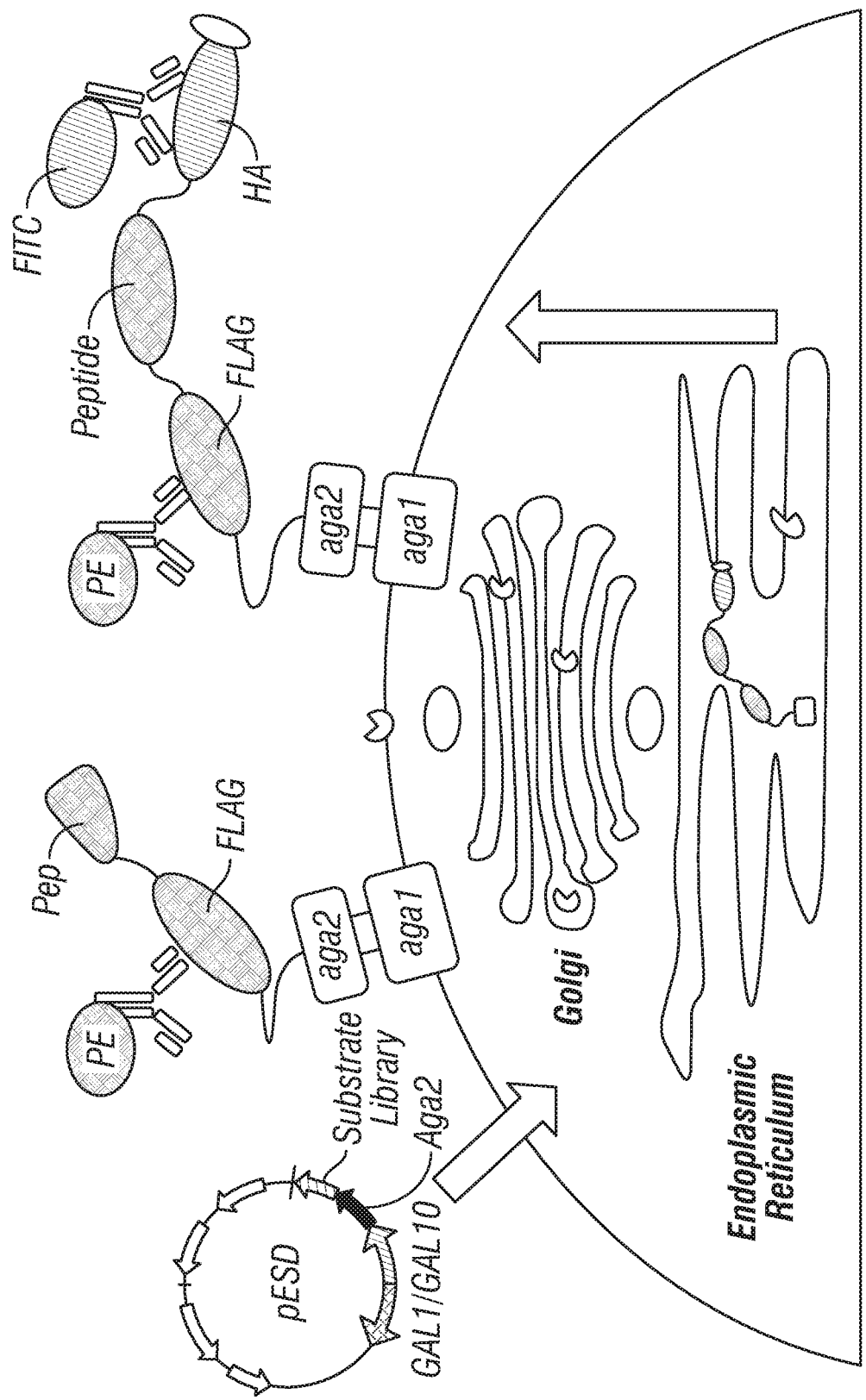
FIGS. 1A-C: The Yeast Endoplasmic Reticulum Sequestration Screening (YESS) system for mapping endopeptidase cleaveOme in yeast secretory pathway. (a) Concept: The Aga2-substrate polypeptide library is expressed from the pESD shuttle vector, and translocated to the ER secretory pathway. The proteolytic cleavage of the substrate fusion polypeptide by the endogenous proteases gives rise to a product with cleaved signal that is displayed on the cell surface by virtue of the N-terminal Aga2. The presence of epitope tags in the processed substrate fusion is detected with fluorescently labeled antibodies to identify the cleaved or non-cleaved signals. (b) Overview of the method. Substrate library is screened and enriched by selecting the library pool of clones showing the cleaved signals. Next generation sequencing is performed to sequence the substrate libraries. Bioinformatic processing is used to analyze the cleaveOme in the yeast secretory pathway. (c) In EBY100 cells, 2-color FACS analysis of cells with cleaved substrate and non-cleaved substrate signals. From Left to Right panel: wild-type TEV substrate (ENLYFQS, SEQ ID NO:8); RLTPR (SEQ ID NO:31) (LXXR (SEQ ID NO:54) pattern); VARRD (Arg-Arg pattern; SEQ ID NO:14); SPAKR (Lys-Arg pattern; SEQ ID NO:32).

The present invention provides, in various aspects, improved methods are provided for measuring the specificity and/or catalytic activity of an enzyme, such as a protease, convertase, or kinase, that can covalently modify a genetically encoded substrate. In some embodiments, methods are provided that employ next generation (NextGen) DNA sequencing in combination with an enzyme engineering platform technology involving yeast endoplasmic reticulum (ER) sequestration screening to identify patterns of substrate specificity and recognition by an enzyme of interest. In some embodiments, an engineered protease, kinase, or convertase may be generated via the methods described herein.

As shown in the below examples, the yeast endoplasmic reticulum (ER) sequestration screening (YESS) platform was used in combination with NextGen sequencing and a comparative sequence analysis to enable an extensive analysis of protease specificity. In these experiments, an Aga2-tagged combinatorial substrate library is targeted to the yeast endoplasmic reticulum (ER) and transported through the secretory pathway, where the substrate can interact with the endogenous and any exogenous protease residing in the ER. After being transported outside of the cell and attached to the yeast surface, the substrate/product can be probed with fluorescently labeled antibodies for the presence or absence of epitopes that reveal the location and extent of substrate cleavage. Multi-color FACS screening was then used to isolate cells with appropriately cleaved substrate, followed by next generation DNA sequencing (NextGen) of the selected sequences to profile substrate specificity. As provided herein, in select preferred embodiments, the endogeneous convertase cleaveOme in the yeast secretory pathway has been mapped and may be used, e.g., to more accurately evaluate and measure the activity of a protease or a mutant protease. As shown in the below examples, comparative sequence analysis demonstrated two and possibly three important cleavage patterns existing within the yeast secretory cleaveOme. Using the YESS-NextGen approach, the inventors were then able to profile the sequence specificity of the wild-type and an engineered variant of the tobacco etch mosaic virus protease (TEV-P).

In some embodiments, the yeast cleaveOme identified by this method may be included computational models to predict the potential cleavage sites in the proteins when transporting in the yeast secretory pathway. Such embodiments may be particularly useful to address or avoid problems associated with proteolytic degradation of a recombinant protein in a yeast cell during production of the recombinant protein in yeast.

As shown in the below examples, the inventors were able to use the combined YESS-NextGen approach to evaluate in comprehensive fashion the sequence specificity of the wild-type TEV-P and an engineered variant TEV-PE10 of the tobacco etch mosaic virus protease. This approach may also be used to evaluate or generate other recombinant or engineered proteases. Having a comprehensive substrate profiling capability within the YESS protease engineering platform may be used in various embodiments to facilitate the rapid identification and full characterization of engineered proteases with desirable cleavage activities.

I. Yeast Endoplasmic Reticulum Sequestration Screening (YESS)

Yeast Endoplasmic Reticulum (ER) Sequestration Screening (YESS) allows for the generation of mutant or modified enzymes including proteases, convertases, and kinases. YESS typically involves expression of a population of enzymes (e.g., proteases, convertases, or kinases) in eukaryotic cells, such as yeast, and detecting the presence or absence of a cleavage or phosphorylation event due to differences in expression of signals on the surface of the yeast using, e.g., using fluorescence activated cell sorting (FACS). YESS may employ sequences on the enzyme and a target sequence that direct the enzyme and the target sequence to the ER of the yeast. In this way, the presence or absence of a cleavage or phosphorylation event may be more accurately detected, since both proteins are directed to the endoplasmic reticulum. YESS may be used to produce a mutant or non-natural protease, convertase, or protein kinase that displays an altered substrate specificity, activity, and/or potency. In order to screen against unwanted promiscuous enzyme or protease variants, the substrate construct can be designed to contain a single selection substrate sequence along with one or more counter-selection substrate sequences. An advantage of this strategy is that intracellular expression of both the protease and substrate are used such that a library of protease variants can be screened against a library of substrate sequences in a "library-on-library" experiment. The library on library approach should increase the odds that a highly active engineered protease-novel substrate pair can be identified through directed evolution. Additional details regarding the YESS method can also be found in WO 2014/004540, Yi et al. (2013), and Yi et al., (2015).

YESS may be used to evaluate a diverse library of substrates to evaluate substrate specificity of an enzyme. Regarding enzyme substrate specificity, there is generally no quantitative measure of absolute substrate specificity; rather, specificity must be discussed in relative terms in which ratios of catalytic parameters with multiple substrates are presented to ascertain patterns of reactivity. Thus, enzyme substrate specificity is defined better when more substrates are considered. Taken to the logical limit, the best possible characterization of enzyme substrate specificity would involve screening all possible substrates using a quantitative analysis followed by a comprehensive deconvolution of reactivity patterns.

Embodiments which utilize comparison of protease or convertase activity in a cell with a cleaveOme of the cell may be used to more accurately determine substrate specificity of the protease or convertase. Generally, a recombinant protease of interest being analyzed in the YESS system will be hydrolyzing substrates above a background of endogenous yeast protease cleavage, in particular, the endogenous proteolysis involved with the yeast cellular secretion pathway. The cellular secretion machinery, including associated processing enzymes, is crucial for successful operation of the eukaryotic secretome (Girard et al. 2013). Even minimal modification of a secretory pathway can drive global change in protein secretion and create wide-ranging cellular effects (Roebroek et al. 1998; Aridor et al. 2000; Aridor et al. 2002). Studies of cellular secretory processes are essential to better understand the factors contributing to effective secretion, with application to recombinant protein production (Sudbery 1996; Porro et al. 2004) as well as helping to uncover potential secretome alterations in diseases such as cancer (Paltridge et al. 2013). In eukaryotes, proteolytic processing in cellular secretory pathways plays an important role in protein maturation and protein sorting into secretory vesicles (Zhou et al. 1999; Seidah et al. 2002). Most secreted proteins, including growth factors, receptors, enzymes and neuropeptides, require proteolytic processing at specific sites (Beinfeld 1998). Emphasizing their importance, null mutation in certain of these known convertase genes have lethal effects on embryos (Roebroek et al. 1998).

An overview of the YESS protease engineering strategy used in the below examples is presented in FIGS. 1A-C. In some embodiments, a protease variant and a cell-surface display (e.g., Aga2)-fused peptide substrate are co-expressed, transported into the yeast endoplasmic reticulum (ER) due to an N-terminal ER signal sequence (e.g., MQLLRCFSIFSVIASVLA, SEQ ID NO:3), and anchored on the ER inner membrane through a C-terminal fusion to the ER retention signal peptide (e.g., FEHDEL, SEQ ID NO:4). In some embodiments, a protein kinase variant may be substituted for the protease variant using these methods. Without wishing to be bound by any theory, the ER targeting may be used to increase the opportunity for a protease-substrate interaction to occur in the confined environment of the ER, thus improving the sensitivity of the assay. Due to a cell-surface (e.g., Aga2) fusion in the substrate construct, the cleaved or uncleaved substrate can be subsequently transported then attached to the yeast surface where it can be labeled with antibodies to detect and quantify the location and extent of cleavage. On a pESD vector, co-expression of the protease and its substrates may be under the control of the galactose inducible GAL1 and GAL10 promoters, respectively. The bidirectional GAL1-GAL10 hybrid promoter, in which GAL1 promoter has a similar individual strength with GAL10 promoter, may be used to drive relatively high-level expression of both the protease and the substrate constructs, although they are expressed as entirely separate polypeptides.

In some aspects, a modified kinase such as a protein kinase may be generated by these methods. The protein kinase may be, e.g., a tyrosine kinase, a serine/threonine-specific protein kinase, a protein-dual-specificity protein kinase, a protein histidine protein kinase, a protein-histidine pros-kinase, a protein-histidine tele-kinase, or a histidine kinase. It is anticipated that virtually any kinase may be used with the methods disclosed herein. For example, if one has one or more enzymes that can distinguish between phosphorylated and unphosphorylated peptides or proteins, then one or more cells expressing a mutant kinase may be identified, e.g., via FACS. Specific kinase types that may be generated include, e.g., members of the eukaryotic protein kinases superfamily including the AGC, CAMK (CaM Kinases), CMGC, CK1, STE, TKL, and thymidine kinases (TK kinases).

In some embodiments, methods of the present invention may be used to generate an engineered convertase. The convertases (also called sortases) are an enzyme class characterized by the ability to ligate two different peptide sequences together. In the sortase reaction mechanism, a first substrate peptide sequence is recognized and cleaved at a specific site to produce a free carboxylic acid group, then the amine terminus of a second specific peptide is attached to this carboxyl group to give the ligated construct. Adapted to the YESS approach, a first peptide substrate sequence containing the sortase cleavage site may be attached or fused to a sequence to allow for yeast cell surface attachment (e.g., such as the AGA2 sequence in some preferred embodiments), and a second peptide substrate sequence that can serve as the peptide to (possibly) be ligated at its amine terminus is preferably fused to an antibody epitope. Both of these substrate sequences may be targeted to the ER for expression via an ER specific signal sequence similar to those used in the protease and kinase embodiments. Only if a sortase, also expressed in the same yeast cell and targeted to the ER, ligates the first peptide substrate sequence to the second peptide substrate sequence, will the epitope be attached to the cell surface via the AGA2 linkage. The presence of epitopes (from the second sequence) attached to the yeast surface will therefore be a direct measure of sortase activity, that can be identified though binding of a labeled antibody that recognizes the epitope (e.g., via FACS). Sequences in the engineered sortase may be randomized, e.g., at or near sites involved sequence recognition, cleavage, and/or ligation, etc. Thus, a sortase may be included as the enzyme in a nucleic acid vector of the present invention and used to engineer a modified sortase that displays, e.g., modified activity, potency, or specificity. In addition, one or both of the substrate sequences can be randomized to develop a comprehensive profile of the substrate specificity of a sortase of interest.

Figure 5A:
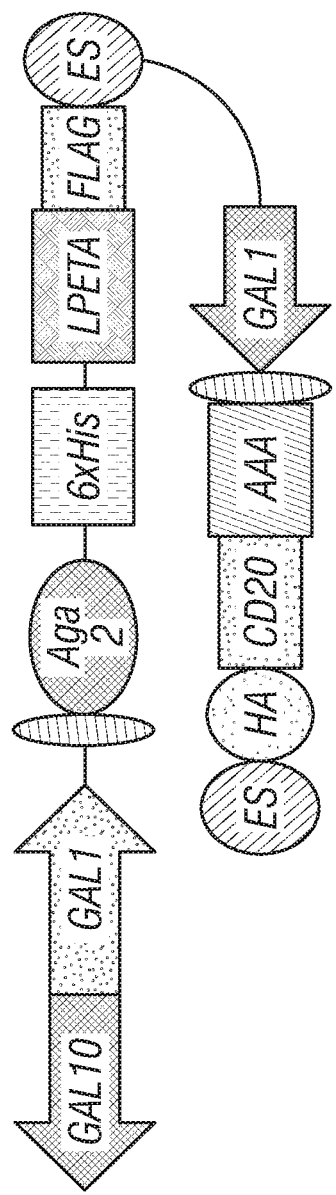
FIGS. 5A-B.
Figure 5B:
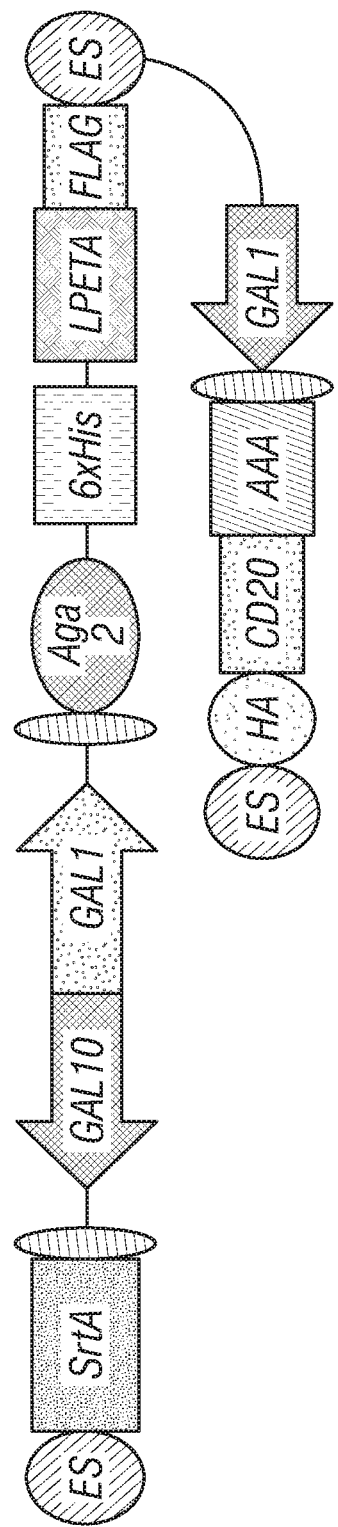

The sortase family of prokaryotic enzymes can catalyze sequence specific transpeptidation reactions on the cell surface of gram-positive bacteria. These membrane-bound enzymes can anchor various virulence factors to the outer cell wall of bacteria that can aid in acquiring nutrients, adhering to sites of infection, and in the evasion of host immunity. There are four classes of sortase enzymes: A, B, C and D. Each enzyme typically recognizes a specific sorting signal, for example LPETG (SEQ ID NO:15) is the sorting signal of sortase A (SrtA) of S. aureus. The thiolate of an active site cysteine in SrtA can catalyze the attack of the scissile threonine-glycine bond. The acyl-enzyme intermediate formed during the reaction is typically resolved via nucleophilic attack by the amino group of a penta-glycine at the N-terminus of branched chain peptidoglycan precursors on the cell wall. As shown in the below examples, various vector constructs may be used, e.g., to analyze sequence specificity of a sortase; for example, in some embodiments positive and/or negative plasmid constructs may be used as shown in FIGS. 5A-B.

Sortases may be utilized for various biotechnological applications including the ligation of various proteins to molecular probes, nucleic acids, glycans and solid supports. For C-terminal labeling, the protein to be labeled generally contains the sortase sorting sequence (e.g., LPETG, SEQ ID NO:15, for S. Aureus SrtA) and the probe generally must contain at minimum a di-glycine amino terminus for ligation. N-terminal labeling may also occur if the probe contains the sorting signal and the protein contains the polyglycine motif. For example, the sequence specificity for various sortases can differ across the different classes of sortases, as well as across species of gram-positive bacteria.

In some embodiments, methods of the present invention may be used to generate an engineered glycosyltransferase. For example, methods used to engineer a glycosyltransferase may be very similar to a the methods used to generate an engineered kinase; however, instead of using an antibody to recognize the presence or absence of a phosphorylation event, an antibody that recognizes the presence or absence of a glycosylation event (e.g., transfer of a carbohydrate, glycoside, oligosaccharide, or a polysaccharide to an amino acid sequence) may be used to identify and or separate one or more glycosyltransferases that exhibit a desired activity. Sequences in an engineered glycosyltransferase may be randomized, e.g., at or near sites involved in sequence recognition or activity, etc. Thus, a glycosyltransferase may be substituted for a kinase in nucleic acid vectors of the present invention and used to engineer a modified glycosyltransferases that displays, e.g., modified activity, potency, or specificity.

A major problem encountered in early protease engineering work was that often, attempts to alter protease specificity only resulted in the production of promiscuous enzymes. In some embodiments, one or more counter selection substrate sequences may be incorporated into the screening protocol (Varadarajan et al., 2008; Varadarajan et al., 2009a), e.g., and included in the vector encoding the substrate and/or the enzyme of interest (e.g., protease, kinase, etc.). In a simultaneous selection/counter selection screen, proteases that maximize cleavage of a desired new substrate sequence while minimizing promiscuous cleavage of the original wild-type or other unwanted substrate sequence are selectively isolated. In various aspects, the protease itself may on occasion act as an effective counter selection substrate in the sense that any protease variant with specificity relaxed to the point that it efficiently cleaves itself will not exhibit a positive signal.

A simultaneous selection/counter selection FACS assay may be achieved by placing elements in the following order: An N-terminal Aga2P anchoring sequence followed by the wild-type preferred counter selection substrate sequence (Peptide 1), the FLAG epitope tag sequence, the selection substrate sequence, a 6×His sequence, and a C-terminal ER retention signal. Note that the 6×His sequence can serve as an epitope tag owing to the ready availability of anti-6×His antibodies. Anti-FLAG and anti-6×His antibodies may be purchased as the phycoerythrin (PE) and FITC conjugates, respectively. Specific cleavage at the desired new substrate sequence (only Peptide 2) would result in a product that maintains the FLAG epitope, but not the 6×His sequence. Thus, a yeast cell harboring a protease variant with a desired new substrate activity would have high PE fluorescence, but relatively low FITC fluorescence. A nonspecific protease would lead to cleavage at both the counter selection and selection sequences, leading to no signal with either antibody. Similarly, an enzyme with unaltered wild-type specificity would give a similar lack of signal with either antibody due to cleavage at the Peptide 1 sequence. Protease variants with no activity with either sequence would have similarly high PE and FITC signals. These three outcomes are easily separated by FACS using a two-dimensional analysis in which gates are set for high signal in the PE channel, but low signal in the FITC channel.

In some aspects, the YESS approach can utilize a tunable dynamic range. For example, one may vary the sequence of the protease, or the selection substrate cleavage sequence, or both simultaneously. Thus, the YESS system may be used to carry out a variety of experiments, including, e.g., the following three distinct types of experiments: 1) A protease library may be screened in an effort to identify activity with a single, desirable new target sequence. 2) A single protease could be screened against a library of substrate sequences to identify the overall substrate preferences of a protease. 3) In an attempt to maximize the chances of finding a protease variant with altered sequence specificity, a protease library could be screened against a library of potential target substrate sequences, a so-called "library-on-library" experiment. An advantage of the YESS approach is that the dynamic range of the assay can be adjusted by subtracting the ER retention sequences on either the protease or substrate sequences, or both, if desired. In this way, the stringency of the assay can be significantly increased by reducing the amount of time the protease and substrate can interact in the confines of the ER.

In addition, the compartmental nature of eukaryotic cells makes possible the specific targeting of both protease and substrate to the same compartment, namely the ER. Having the protease interact with substrate in the relatively confined environment of the ER provides a considerable level of control that is not possible in the cytoplasmic milieu. In particular, by adding a C-terminal ER retention sequence, both the protease and substrate can be anchored on the ER membrane, increasing ER residence time, local protease/substrate concentrations, and therefore assay sensitivity. Increased assay sensitivity may be particularly helpful during initial library screens. When intermediate sensitivity is needed, for example during the middle rounds of library optimization/screening, the ER retention signal can be left off of either the protease or substrate. At the end of a screening experiment, when only the most active variants are being sought, the assay can be made even less sensitive by leaving off the ER retention sequences altogether.

The YESS approach can incorporate features useful for library screening. For example, simultaneous selection and counter selection screens may be used to avoid isolating variants with relaxed specificity (Varadarajan et al., 2005; Varadarajan et al., 2008; Sellamuthu et al., 2008; O'Loughlin et al., 2006). Any number of counter selection substrate sequences (e.g., 1, 2, 3, 4, 5, 6, 7, 8, 9, 10, or more) can be added to the YESS substrate construct to refine specificity. Additionally, because both the protease and substrate constructs are typically genetically encoded in the YESS approach, a library can be used for either one. Thus, a novel protease substrate specificity for a single desired substrate can be sought, e.g., by using a protease library with one substrate construct. The converse situation, in which a single protease is used in conjunction with a substrate library, can be used to identify the substrate specificity profile of a protease. In order to improve the chances of finding a new protease-substrate combination, a protease library can be screened against a substrate library (also referred to as a "library-on-library" approach).

Notably, a stop codon inserted in the substrate sequence or an otherwise truncated construct, such as a frame-shift, would give a false positive FACS signal by mimicking a cleaved product. For this reason, all stop codon containing or frame-shifted substrate constructs may be removed in a preliminary FACS screen. The prescreened substrate library may then be combined with the enzyme (e.g., protease) library, followed by FACS screening. In order to increase the probability of in the initial screens, assay sensitivity was increased by including the C-terminal ER retention signals in both the protease and substrate constructs.

In various embodiments, the YESS system can be used to generate enzymes such as proteases with significantly altered substrate specificity while maintaining high overall catalytic activity. These methods may be used, e.g., to produce a protease with improved industrial, laboratory, or clinical utility (e.g., due to alterations in catalytic efficiency and/or specificity of the protease). In addition, the methods disclosed herein may be used to detect other enzymatic reactions compatible with reaction in the ER, where the reaction product can be displayed and detected on the yeast outer surface.

II. Proteases

The present invention may be used in various aspects to engineer a protease. A variety of proteases may be generated via these methods, such as, e.g., a TEV protease, a tissue plasminogen activator, such as a recombinant tissue plasminogen activator (rTPA), a protease that targets or affects the function of a proteinase-activated receptor (PAR), or any protease capable of expression in yeast. In some embodiments, the engineered protease may be used in research to cleave a peptide linker, e.g., to separate protein entities in a fusion protein. In some embodiments, the engineered protease is a therapeutic protease. The therapeutic protease may be useful in treating diseases, including, but not limited to, cardiovascular disease, sepsis, a digestive disorder, inflammation, cystic fibrosis, a retinal disorder, psoriasis, cancer, a cell proliferative disease, diabetes, blood coagulation disorders (e.g., hemophilia, a deficiency in factor 7 and/or factor 9), an autoimmune disorder (e.g., psoriasis, lupus, etc.), an inflammatory lung disease (e.g., cystic fibrosis, emphysema, sarcoidosis, etc.), or asthma, as well as in disorders of the cardiovascular, musculoskeletal, gastrointestinal, respiratory, and/or central nervous system.

The methods provided herein may be used to identify new proteases. Several proteases, such as the important protease rTPA, are currently used clinically (Craik et al., 2011; Ramachandran et al., 2012), but the therapeutic application of proteases has thus far been limited to situations in which a naturally occurring protease cleavage specificity is of therapeutic benefit. The ability to precisely engineer a desired new sequence specificity into a human protease may facilitate the investigation of proteases as a general alternative to antibody therapeutics (Craik et al., 2011; Ramachandran et al., 2012). Compared to antibodies, which are relatively large molecules that bind/inactivate their therapeutic targets in stoichiometric fashion, a properly engineered therapeutic protease may require a much lower dose because it is significantly smaller and capable of catalytic inactivation of its target. Moreover, other proteases, such as TEV-P and subtilisin, have found significant academic as well as commercial applications, and adding one or more new specificities may be used to increase their potential uses.

III. Nucleic Acid Constructs

Certain aspects of the present invention involve nucleic acids that encode an enzyme that can modify a genetically encoded substrate (e.g., a protease, convertase, or kinase) and/or an amino acid substrate. The protease and the substrate may be expressed as a fusion protein with one or more additional sequences, such as an ER targeting sequence, an ER retention sequence, a cell-surface sequence, and/or one or more immunotag sequences. In some embodiments, a single nucleic acid may be used to express both a protease and an amino acid substrate in a cell. It is generally anticipated that, although expressing both a protease and an amino acid substrate from a single vector or construct may effectively allow for interactions between the protease and amino acid substrate in a cell, in some embodiments the protease and amino acid substrate may be encoded by two different or separate nucleic acids or vectors, and the two nucleic acids may be expressed in a cell, such as a yeast cell.

In some embodiments, the following construct may be generated and used. Under the control of the GAL10 promoter and after the Aga2 gene used for yeast surface display, a five-part cassette may be cloned that includes (1) the native substrate of a protease (e.g., TEV-P, ENLYFQS, SEQ ID NO:8); (2) a first epitope tag sequence (e.g., a FLAG tag, DYKDDDDK, SEQ ID NO:9); (3) the designed peptide substrate library (e.g., ENLYFXS, X can be any residue, SEQ ID NO:10); (4) a second epitope tag (e.g., 6×His tag, HHHHHH, SEQ ID NO:11); and (5) an ER retention signal peptide (e.g., FEHDEL, SEQ ID NO:4). Under the control of the GAL1 promoter, the protease library (such as the TEV-P library, see below) may be cloned along with a designed N-terminal ER targeting signal peptide (QLLRCFSIFSVIASVLA, SEQ ID NO:12) and with or without a C-terminal ER retention signal peptide.

Endoplasmic Reticulum (ER) Targeting Sequences

The construct may comprise 1, 2, or more sequences for targeting an amino acid sequence (e.g., comprising a protease or a substrate sequence) to the endoplasmic reticulum (ER). In some embodiments, the HDEL (SEQ ID NO:6) system may be used as described in Monnat et al. (2000), which is incorporated by reference herein in its entirety. In some embodiments, the ER targeting signal peptide (QLLRCFSIFSVIASVLA, SEQ ID NO:12) is used. The ER targeting signal peptide may be at or near the N-terminal portion such that an amino acid comprising a protease or substrate sequence can be targeted to the ER.

Without wishing to be bound by any theory, the ER targeting sequence may bind a ribosome and allow for the amino acid to be transported into the ER. Generally, an ER targeting sequence may promote entry of an amino acid sequence, peptide, or protein, by promoting entry of the protein into the ER through the translocon, e.g., via a protein-conducting channel formed by a conserved, heterotrimeric membrane-protein complex referred to as the Sec61 or SecY complex. In some embodiments, a sequence disclosed as an ER targeting sequence of Rapoport (2007), Hedge and Keenan (2011), or Park and Rapoport (2012) may be used with the present invention. In some embodiments, an N-terminal targeting sequence for promoting entry into the endoplasmic reticulum may be identified via the Predotar (Prediction of Organelle Targeting sequences) method disclosed in Small et al. (2004).

Endoplasmic Reticulum (ER) Retention Sequences

Once in the ER, in certain embodiments, it may be preferable to include an ER retention sequence or peptide in order to allow or promote an amino acid (e.g., comprising a protease or a substrate sequence) to remain in the interior of the ER.

In some embodiments, the ER retention signal peptide is FEHDEL (SEQ ID NO:4). The HDEL (SEQ ID NO:6) system may be used as described in Monnat et al. (2000). In some embodiments, a protein chimera may be generated that contains a C-terminal tetrapeptide sequences of (-KDEL (SEQ ID NO:5), -HDEL (SEQ ID NO:6), or -RDEL (SEQ ID NO:7)) to promote retention in the ER. If only a partial retention in the ER is desired, a protein chimera may be generated that contains C-terminal sequence (-KEEL, SEQ ID NO: 16). In some embodiments where it is desirable a mammalian cell line for expression of constructs, it may be useful to use the mammalian (-KDEL, SEQ ID NO:5) sequence in a fusion protein with a protease or a substrate. The particular ER retention sequence used may be chosen based on the amount of retention in the ER produced in a particular eukaryotic cell type. In some embodiments, an upstream sequence beyond the C-terminal tetrapeptide may be included that can influence or may be part of the structure of reticuloplasmin retention signals. In various aspects, a sequence may be included in a chimeric protease or in a chimeric substrate that promotes retention of the protein or peptide in the ER by affecting one or more of the following mechanisms: sorting of exported protein, retention of residents, and/or retrieval of escapees.

HDEL (SEQ ID NO:6) sequences are further described in Denecke et al. (1992). In some embodiments, an ER targeting sequence or ER retention sequence of Copic et al. (2009) may be used. In some embodiments, an ER-targeting sequence, such as the cytoplasmic KKXX (SEQ ID NO:17) or RR of Teasdale and Jackson (1996), may be used. The ER-targeting sequence may be a Kar2p retention mutant, e.g., as described in Copic et al. (2009). In some embodiments, the C-terminal sequence -VEKPFAIAKE (SEQ ID NO:18) described in Arber et al. (1992), may be used to promote localization to a subcompartment of the ER. Each of the foregoing references is incorporated by reference in its entirety.

Epitope Tag Sequences

A construct of the present invention may comprise one, two, or more epitope tag or immunotag sequences conjugated to or expressed as a fusion protein with the substrate target on the surface of a cell (e.g., a yeast cell). It is anticipated that virtually any epitope tag may be used in various embodiments of the present invention. For example, epitope tags that may be included in a peptide or encoded by a nucleic acid of the present invention include, e.g., FLAG, 6×His, hemagglutinin (HA), HIS, c-Myc, VSV-G, V5 HSV, and any peptide sequence for which a monoclonal antibody is available. Antibodies that selectively bind the epitope tag sequences may be used to detect the presence or absence of the epitope tag(s); for example, a first antibody with a first fluorophore may be used to detect the presence or absence of a first epitope tag sequence, a second antibody with a second fluorophore may be used to detect the presence or absence of a second epitope tag sequence, and additional antibodies may be used to detect the presence or absence of a third, fourth, fifth, etc. epitope tag, as desired. In some embodiments, the antibodies are labeled with a dye, such as a fluorophore, and used for cell sorting. As would be appreciated by one of skill in the art, a wide variety of antibodies that selectively recognize an epitope tag and are labeled with a detectable label such as a fluorophore are commercially available. Antibodies that selectively bind different epitope tags may be labeled with different fluorophores; in this way, cells may be separated or purified based on the presence or absence of one, two, three, or more fluorometric signals, e.g., using ratiometric FACS.

A wide variety of epitope tags have been engineered into recombinant proteins and may be used in various embodiments of the present invention. Epitope tags that may be used include, e.g., FLAG®, HA, HIS, c-Myc, VSV-G, V5, and HSV. Select epitope tags that may be used with the present invention are listed below.

TABLE 2

Select Epitope Tag Sequences

| Tag | Sequence | SEQ ID NO: |
|---|---|---|
| HIS | HHHHHH | SEQ ID NO: 11 |
| c-MYC | EQKLISEEDL | SEQ ID NO: 19 |
| HA | YPYDVPDYA | SEQ ID NO: 20 |
| VSV-G | YTDIEMNRLGK | SEQ ID NO: 21 |
| HSV | QPELAPEDPED | SEQ ID NO: 22 |
| V5 | GKPIPNPLLGLDST | SEQ ID NO: 23 |
| FLAG | DYKDDDDK | SEQ ID NO: 9 |

Cell Surface Display Sequence

The construct may comprise a sequence for expression on the cell surface. For example, after Golgi-derived vesicle to plasma membrane fusion occurs where the vesicle contains a substrate (containing a ER targeting sequence and an ER retention sequence), a cell-surface display sequence may be used to retain an amino acid (e.g., comprising one or more cleaved or uncleaved substrate sequences) on the surface of a eukaryotic cell, such as, e.g., a yeast cell.

In some embodiments, an Aga2p sequence can be used to display an amino acid sequence, such as a cleaved or uncleaved substrate amino acid sequence, on the surface of a eukaryotic cell, such as a yeast. For example, yeast cells can display a substrate from a randomized library extracellularly as a fusion to the Aga2p cell surface mating factor, which is covalently bound to the Aga1p mating factor via disulfide bonds (e.g., see FIG. 1). Expression of a fusion construct comprising Aga2p on the surface of yeast. Aga2p is an adhesin protein that is involved in agglutinin interaction mediated by Aga1p-Aga2p complexes and Sag1p (Huang et al., 2009), and Aga2p may be used for extracellular expression of a fusion protein in yeast (e.g., Kim et al., 2010; Boder and Wittrup, 1997). The Aga2p approach for expression of fusion proteins on the surface of yeast may be used for expression of a wide variety of proteins (Gai et al., 2007).

In other embodiments, an amino acid sequence, such as a cleaved or uncleaved substrate, may be displayed on the cell surface of a cell, such as a yeast using a glycosylphosphatidylinositol (GPI) anchor attachment signal sequence.

A mammalian mannosetypeMan5GlcNAc2 N-linked glycans may also be used to display a substrate. For example, a glycoengineered *Pichia pastoris* host strain that is genetically modified to secrete glycoproteins may be particularly useful for displaying a glycoprotein via this method as described, e.g., in Lin et al. (2011). This surface display method may use a linker (e.g., a pair of coiled-coil peptides) while using a GPI-anchored cell surface protein as an anchoring domain, such as, e.g., the *Saccharomyces cerevisiae* Sed1p GPI-anchored cell surface protein.

A self-assembled amyloid-like oligomeric-cohesin scaffoldin may be used for protein display on a yeast, such as, e.g., *Saccharomyces cerevisiae*. For example, the cellulosomal scaffolding protein cohesin and its upstream hydrophilic domain (HD) may be genetically fused with the yeast Ure2p N-terminal fibrillogenic domain consisting of residues 1 to 80 (Ure2p1-80). The resulting Ure2p1-80-HD-cohesin fusion protein may be expressed in *Escherichia coli* to produce self-assembled supramolecular nanofibrils that can serve as a protein scaffold. The excess cohesin units on the nanofibrils provide ample sites for binding to dockerin fusion protein, such as a dockerin-substrate fusion protein. Self-assembled supramolecular cohesin nanofibrils created by fusion with the yeast Ure2p fibrillogenic domain can provide a protein scaffold that can be effectively used for yeast cell surface display. Related methods are described in additional detail in Han et al. (2012).

In some embodiments, the construct may comprise an Aga2p sequence. The Aga2p yeast display system (Boder and Wittrup, 1997) has been previously characterized and may be used in various aspects of the present invention. Non-limiting examples of proteins that may be used as cell-surface proteins are described in Chen et al. (2011); Lee et al. (2011); Lin et al. (2012); Han et al. (2012); Gai et al. (2007); and article in press as: Gera et al. (2012), each of which are incorporated by reference in their entirety.

Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques. In certain preferred embodiments, the vector can express a nucleic acid sequence in a eukaryotic cell, such as, e.g., a yeast cell.

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well, such as those described herein.

An expression vector may comprise, for example, one or two or more promoters, enhancers, initiation signals, internal ribosome binding sites, multiple cloning site (MCS), RNA splicing sites, termination signals, polyadenylation signals, origins of replication (often termed "ori"), or selectable or screenable markers.

IV. Expression in Eukaryotic Cells

In certain aspects of the present invention, a protease and protease substrate may be expressed in eukaryotic cells. Cells that may be used with the present invention include, e.g., yeast, mammalian cells, insect cells, stem cells, human cells, primate cells, induced pluripotent stem cells, cancerous cells, and embryonic cell lines (e.g., HEK 293 cells, etc.). In some embodiments, yeast cells are used. In some embodiments, the yeast cells are Kex2 (−/−) knockout yeast cells. It is anticipated that, in various embodiments, virtually any cell that contains an endoplasmic reticulum (ER) may be used to selectively target a protease and a substrate to the ER of the cell.

Using eukaryotic cells, such as yeast, for expression of a protein or enzyme of interest can offer significant advantages over using bacteria. For example, in view of previous experience with *E. coli*-based protease engineering systems (Varadarajan et al., 2008) as well as yeast surface expression (Boder and Wittrup, 1997), the YESS approach uses eukaryotic cells and thus can offer several potential advantages for protease engineering. For example, the eukaryotic expression machinery in yeast can be more compatible with mammalian proteases, especially human proteases, as compared with bacteria, such as *E. coli*.

In some embodiments, yeast cells are used for selection of a protease. Yeast cells may in some embodiments be advantageously used since, e.g., they are capable of dividing quickly and are relatively robust and allow for a reasonably simple culture. Yeast cell lines that may be used with the present invention include, e.g., GS115 cells, INVSc1 cells, KM71H cells, SMD1168 cells, SMD1168H cells, and X-33 cells. It is anticipated that virtually any strain of yeast may be used with the present invention. In some embodiments the yeast may be, e.g., *Saccharomyces cerevisiae* or *Pichia pastoris*. The yeast may be an Ascomycota, such as a Saccharomycotina (referred to as "true yeasts"), or a Taphrinomycotina, such as Schizosaccharomycetales (the "fission yeasts").

Various insect cell lines may be used with the present invention. For example, insect cells that may be used with the present invention include, e.g., *Drosophila* cells, Sf9 cells, and Sf21 cells.

Mammalian cell lines that may be used with the present invention include, e.g., HEK 293 cells, CHO cells, 3T3 cells, BHK cells, CV1 cells, Jurkat cells, and HeLa cells. In some embodiments, a human cell line may be used.

V. Cell Sorting

Cells may be sorted based on the presence of one or more sequences on the surface of the cell. For example, cells may be sorted using fluorescence-activated cell sorting (FACS) or magnetic-activated cell sorting (MACS).

Subsequent to cell sorting, the specific protease produced by a yeast may be determined by genotyping nucleic acids from a colony of the yeast. A variety of known methods may be used for nucleotide sequencing. Virtually any sequencing method, such as, for example, traditional methods of sequencing or next-generation sequencing methods, may be used to determine one or more of the proteases expressed in a cell. In some embodiments, the nucleotide sequencing can be determined, e.g., by pyrosequencing or by chain termination sequencing.

Magnetic-Activated Cell Sorting (MACS)

Cells that selectively express a particular target sequence on the surface of the cells (e.g., a substrate sequence that displays cleavage due to expression of a protease that selectively cleaves a target substrate) may be isolated from other cells using a magnetic-activated cell sorter (MACS). MACS typically utilizes an antibody (e.g., an antibody that selectively binds an epitope tag sequence located within an expressed protein or peptide), in combination with magnetic beads to separate cells over a column. MACS may, in certain embodiments, be relatively gentle on cells and favorably affect cell viability and integrity of certain mammalian cell lines as compared to FACS.

Various MACS products are commercially available, including MACS MicroBeads™ columns or AutoMACS™ (Miltenyi Biotec, CA, USA), and may be used according to the manufacturer's instructions. PBS/0.5% BSA (without EDTA) may used as the buffer for cell isolation. In some experiments, a Dead Cell Removal Kit (Miltenyi Biotec) may be used to remove dead cells prior to isolation of cells that express a cleaved target sequence. Repeated MACS columns may be used if necessary.

Fluorescence-Activated Cell Sorting (FACS)

Fluorescence-activated cell sorting (FACS) may also be used to separate cells that express a particular target sequence, e.g., that has been cleaved by a protease. FACS utilizes the degree of fluorescence exhibited by a cell to separate cells. In certain embodiments, one, two, or more anti-epitope tag antibodies comprising different fluorescent labels may be used to separate or purify a cell, such as a yeast cell, that expresses a cleaved or uncleaved substrate on the surface of the cell (indicating the presence of a protease with a particular specificity, activity, or potency).

In some embodiments, FACS screening or other automated flow cytometric techniques may be used for the efficient isolation of a eukaryotic cell (e.g., a yeast cell) comprising a protease that exhibits a desired specificity, potency, or efficiency. Instruments for carrying out flow cytometry are known to those of skill in the art and are commercially available to the public. Examples of such instruments include FACStar™ Plus, FACScan™, and FACSort™ instruments from Becton Dickinson (Foster City, Calif.), Epics C from Coulter Epics Division (Hialeah, FA), and MOFLO™ from Cytomation (Colorado Springs, Colo.).

FACS may be used for sorting of cells. In various embodiments, the presence or absence of 1, 2, or more antibodies, which recognize 1, 2, or more epitope tags on the surface of a cell, reflects the activity of a protease. For example, the absence of a signal may indicate undesired activity of a protease, no activity of a protease, or desired activity of a protease. FACS may also be used to separate cells that have been transformed with a desired construct from cells that do not contain or have not been transformed with a desired construct.

Flow cytometric techniques in general involve the separation of cells or other particles in a liquid sample. Typically, the purpose of flow cytometry is to analyze the separated particles for one or more characteristics, such as, e.g., presence of a labeled ligand or other molecule. FACS generally involves the direction of a fluid sample through an apparatus such that a liquid stream passes through a sensing region. The particles should pass one at a time by the sensor and are categorized base on size, refraction, light scattering, opacity, roughness, shape, fluorescence, etc.

Rapid quantitative analysis of cells proves useful in biomedical research and medicine. Apparatuses permit quantitative multiparameter analysis of cellular properties at rates of several thousand cells per second. These instruments provide the ability to differentiate among cell types. Data are often displayed in one-dimensional (histogram) or two-dimensional (contour plot, scatter plot) frequency distributions of measured variables. The partitioning of multiparameter data files involves consecutive use of interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls.

FACS is described further, e.g., in U.S. Pat. Nos. 3,826,364; 4,284,412; 4,989,977; 4,498,766; 5,478,722; 4,857,451; 4,774,189; 4,767,206; 4,714,682; 5,160,974; and 4,661,913, each of which are specifically incorporated herein by reference.

In some embodiments, flow cytometry can be used repeatedly during multiple rounds of screening that are carried out sequentially. Cells may be isolated from an initial round of sorting and immediately reintroduced into the flow cytometer and screened again to improve the stringency of the screen. In some embodiments, non-viable cells can be advantageously recovered or separated using flow cytometry. Since flow cytometry generally involves a particle sorting technology, the ability of a cell to grow or propagate is not necessary in various embodiments of the present invention. Techniques for the recovery of nucleic acids from such non-viable cells are well known in the art and may include, for example, use of template-dependent amplification techniques, including PCR.

Bioreactors and Robotic Automation

One or more steps for the culture or separation of cells may be automated. Automating a process using robotic or other automation can allow for more efficient and economical methods for the production, culture, and differentiation of cells. For example, robotic automation may be utilized in conjunction with one or more of the culture of eukaryotic cells, passaging, addition of media, and separation of cells expressing a cleaved or uncleaved substrate, e.g., using MACS or FACS.

A bioreactor may also be used in conjunction with the present invention to culture or maintain cells. Bioreactors provide the advantage of allowing for the "scaling up" of a process in order to produce an increased amount of cells.

Various bioreactors may be used with the present invention, including batch bioreactors, fed batch bioreactors, continuous bioreactors (e.g., a continuous stirred-tank reactor model), and/or a chemostat. A bioreactor may be used, e.g., to produce increased numbers of eukaryotic cells, such as yeast.

VI. Next Generation Sequencing

A variety of next generation-sequencing systems may be used with the present invention include. For example, the next-generation sequencer may utilize single-molecule real-time sequencing (e.g., produced by Pacific Biosciences, Menlo Park, Calif.), an ion semiconductor method (e.g., Ion Proton™, Ion PGM™), a pyrosequencing method (e.g., 454), a sequencing by synthesis method (e.g., an Illumina™ sequencer), or a sequencing by ligation method (e.g., a SOLiD™ sequencer). In some embodiments, the next generation sequencer is an Illumina™ sequencing system, or an Ion Torrent system (e.g., the Ion Proton™ Sequencer or the Ion PGM™ sequencer) from Life Technologies (Carldbad, Calif., USA), SOLID, SOLID 2.0, 5500 Genetic Analyzer (e.g., 5500, 5500 W, etc.; Life Technologies, Carlsbad, Calif.) may be used in various embodiments of the present invention. In some embodiments, an automated method for sample preparation may be used; for example, the Ion Chef™ system may be used, e.g., in combination with an ion semiconductor sequencer such as, e.g., Ion Proton™ or Ion PGM™ (e.g., using the Ion 314™ Chip, Ion 316™ Chip, Ion 318™ Chip Ion PI™ Chip, or Ion PII™ Chip). Various Illumina systems are available and may be used in embodiments of the present invention such as, e.g., the HiSeq X Ten, HiSeq 2500, NextSeq 500, and MiSeq systems. The next-generation sequencing method may involve constructing a library by generating DNA, fragmenting the DNA, and then adding adaptors. Then the fragmented DNA may be amplified on beads, e.g., using emulsion PCR. In some embodiments, the next-generation sequencing method does not utilize beads (e.g., 5500 W, Illumina sequencers, etc.). It is anticipated that In some embodiments, amplification of sequences may be accomplished on a glass surface or solid support.

A. Data Analysis

Data obtained regarding the endogenous activity of an enzyme (e.g., a protease, a convertase, or a kinase) in a eukaryotic cell such as a yeast may be subjected to data analysis to identify patterns in the amino acid sequences associated with the catalytic activity (e.g., cleavage, phosphorylation, cleavage and ligation, etc.). As would be appreciated by one of skill in the art, a variety of algorithms may be used for this purpose. For example, sequences comprising a stop codon may be excluded. In some embodiments, each amino acid in a randomized sequence (e.g., a cleavage sequence that is 4-7 amino acids in length, a protein comprising a cleavage sequence that comprises 4-7 randomized amino acids) may be sequentially fixed as a given amino acid, and then the relative likelihood of the other randomized amino acids in the sequence may be determined, e.g., by calculating a specificity score for the remaining amino acids.

In some embodiments, the sequences may be first subjected to a quality filter to check for proper FLAG tag and HA tag sequences and to exclude the sequences containing a stop codon before extracting the peptide substrate repertoire information. In some instances (e.g., for recombinant TEV protease substrate profiling), sequences containing Lys or Arg may also be excluded before extracting the peptide repertoire information. Software programs may then be used to identify peptide substrate counts and positional-based amino acids compositions. In some embodiments, a specificity score algorithm may be used to identify enrichment in a given position described as follows: positive specificity score=(frequency of amino acid at a given position (in postselection library) −frequency of amino acid at position (preselection))/(1-frequency of amino acid at position (preselection)); negative specificity score=(frequency of amino acid at position (postselection) −frequency of amino acid at position (preselection))/(frequency of amino acid at position (preselection)). Positive specificity scores reflect amino acids that appear with greater frequency in the post-selection library than in the starting library at a given position. Negative specificity scores reflect amino acids that are less frequent in the post-selection library than in the starting library at a given position.

The positional correlation of amino acids in a substrate amino acid sequence within a cleaveOme may be measured based on the effects of mutations at each position of the substrate amino acid. For the mutations, both pre-selection library sequences and post-selection sequenced may be filtered to include the sequences that only contain specific residues at each position. Specificity scores may then be calculated, for the mutation-filtered libraries, based on the same specificity score algorithm described above to identify enrichment in a given position corresponding to the mutations at indicated positions. Sequence logo for the PWM (position weight matrix) of the postselection substrate libraries may also be generated by WEBLOGO 3.

In some embodiments, amino acid frequencies may vary based on the amino acid's neighbor's identity. By fixing a particular amino acid at a given position (e.g., position Y-1), the enrichment or de-enrichment of a particular amino acid at neighboring positions (e.g., Y-2, Y-3, etc.) may be calculated. To build a model accounting for this co-variation, the frequency of each amino acid-position combination may be calculated in the context of one or two other amino acid-position combinations. This model may then be queried by submitting a 6-mer amino acid sequence with tyrosine in the third position. The frequency of each amino acid-position combination may be multiplied, along with the co-frequencies of every possible di- and tri-amino acid combination. This overall frequency may be calculated from both a post-sorted pool (e.g., DNA from yeast after separation by FACS) and the unsorted pool (e.g., yeast prior to FACS sorting). Dividing the post-sorting frequency value by the pre-sorting frequency value results in a ratio of the frequencies. Logarithmic transformation of this ratio produces a "Likelihood Score", where positive values indicate the sequence was more likely to be found in the post-sorting pool than the pre-sorting pool, and vice versa.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Plasmid Construction

The plasmid pESD-Q97 was based on the vector pESD (Li et al., 2013). The Aga2 gene downstream of the GAL10 promoter was fused to a four-part cassette encoding: (1) the FLAG tag sequence, DYKDDDDK (SEQ ID NO:9); (2) the native substrate of TEV-P, ENLYFQS (SEQ ID NO:8); (3) the HA tag sequence, YPYDVPDYA (SEQ ID NO:20); and (4) the ER retention signal sequence, FEHDEL (SEQ ID NO:4). The plasmid pESD-Q97 contained NheI and PstI restriction enzyme sites for homologous recombination. The vectors for recombinant TEV protease substrate profiling (pESD-Q105 and pESD-Q106) were generated by cloning of wild-type TEV-P sequence with the ER retention signal sequence or the engineered TEV-PE10 variant sequence with the ER retention signal sequence into the pESD-Q97 vector downstream of the GAL1 promoter.

Substrate Library Construction

For the construction of the five-amino acid randomized substrate library, PAGE-purified primers (Primer 1 and Primer 2, Table 3), which contained five randomized NNS codons, were used to amplify the entire substrate fusion construct composed of Aga2, Flag antibody epitope sequence, the randomized substrate sequence, the HA antibody epitope sequence and a C-terminal ER retention sequence. The PCR products were then inserted downstream of the GAL10 promoter in pESD-Q97 vector by homologous recombination, in the *Saccharomyces Cerevisiae* EBY100 strain (URA+, leu−, trp−). PAGE-purified primers (Primer 1 and Primer 4, Table 3), which contained four randomized NNS codons at positions P1', P1, P3 and P6 within the substrate region (XNLXFXX, SEQ ID NO:24), were used to generate the substrate library of recombinant TEV protease.

TABLE 3

Primers

| Primers | Sequences |
|---|---|
| Primer 1 | 5'-CTA GTA TCG ATG CAG TTA CTT CGC TGT TTC TCA ATC TTT TCG GTG ATT GCT AGC GTT TTA GCA CAG GAA CTG ACA ACT ATA TGC G-3' (SEQ ID NO: 25) |
| Primer 2 | 5'-GGAGACTTGA CCAAACCTCT GGCGAAGAAT TGTTAATTAA GAGCGCATGC CGACTCCTGC AGTCACAATT CGTCGTGTTC GAAACTACCA GCGTAGTCTG GAACGTCGTA TGGGTAACTA CCACTGCCSN NSNNSNNSNN SNNACTACCA CTGCCTTTAT CGTCGTCATC TTTATAATC-3' (SEQ ID NO: 26) |
| Primer 3 | 5'-GCGTAGTCTGGAACGTCGTATGGG-3' (SEQ ID NO: 27) |
| Primer 4 | 5'-GGAGACTTGACCAAACCTCTGGCGAAGAATTGTTAAT TAAGAGCGCATGCCGACTCCTGCAGTCACAATTCGTCGTG TTCGAAACTACCAGCGTAGTCTGGAACGTCGTATGGGTAA CTGCCSNNSNNGAASNNCAAATTSNNACTACCT TTATCGTCGT CATCTTTATA ATC-3' (SEQ ID NO: 28) |

In Vivo Selection

Cells were grown to an $OD_{600}$ of 2.0-3.0 in 1 L YNB-CAA+glucose medium, and then $3 \times 10^8$ cells, around 10-fold larger than the library size, were induced with YNB-CAA+galactose medium at a final $OD_{600}$ of 0.5. Following media exchange, the cells were grown at 30° C. overnight, with shaking. $3 \times 10^8$ cells were washed and then labeled with fluorescently labeled antibodies: anti-FLAG-PE antibody (ProZyme, Hayward, Calif., USA) and anti-6×His-FITC antibody (Genscript, Piscataway, N.J., USA). During the antibody labeling steps, the cells were resuspended into 1×PBS solution containing 0.5% BSA with a final cell density of $10^5$ cells/μL. To avoid the bacterial contamination, penicillin and streptomycin were added into the growth and inducing medium, with the final concentration of 100 units and 100 μg per mL, respectively. The amounts of antibody used for labeling are 0.02 μg/μL and 0.1 μg/L for anti-FLAG-PE antibody and anti-HA-FITC antibody, respectively. The antibody labeled cells were washed and resuspended in 1×PBS buffer and sorted using a BD Biosciences FACSAria II flow cytometer (BD Biosciences San Jose, Calif., USA). A total of ~$3 \times 10^8$ cells were sorted. After 3 rounds of cell sorting and resorting, DNA was isolated from the pools of both the enriched substrate libraries and naïve substrate library using an Omega Bio-Tek yeast plasmid Mini Kit. PCR amplification was performed with Phusion DNA polymerase (NEB) to obtain DNA fragments containing the substrate sequences (Primer 1 and Primer 3). The 443 bp PCR product was extracted by agarose gel electrophoresis and submitted to the University of Texas at Austin Genomic Sequencing and Analysis Facility (GSAF). The samples were sequenced using the Hiseq NextGen platform (Illumina, San Diego, Calif.).

Data Analysis

Illumina sequencing reads were analyzed using programs written in Python and Perl. The programs are available upon request. The sequences were first subjected to a quality filter to check for proper FLAG tag and HA tag sequences and to exclude the sequences containing a stop codon before extracting the peptide substrate repertoire information. As for recombinant TEV protease substrate profiling, sequences containing Lys or Arg were also excluded before extracting the peptide repertoire information. The programs were then used to identify peptide substrate counts and positional-based amino acids compositions. In particular, a specificity score algorithm was used to identify enrichment in a given position described as follows: positive specificity score=(frequency of amino acid at a given position (in postselection library) −frequency of amino acid at position (preselection))/(1−frequency of amino acid at position (preselection)); negative specificity score=(frequency of amino acid at position (postselection) −frequency of amino acid at position (preselection))/(frequency of amino acid at position (preselection)). Positive specificity scores reflect amino acids that appear with greater frequency in the post-selection library than in the starting library at a given position. Negative specificity scores reflect amino acids that are less frequent in the post-selection library than in the starting library at a given position.

The positional correlation within the cleaveOme was studied by analyzing the effects of mutations at the position specified by the grey columns on the specificity profile. For the mutations, indicated by the grey columns at the positions, both pre-selection library sequences and post-selection sequenced were filtered to include the sequences that only contained the indicated residues in the grey columns at the positions. Specificity scores were then calculated, for the mutation-filtered libraries, based on the same specificity score algorithm described above to identify enrichment in a given position corresponding to the mutations at indicated positions. Sequence logo for the PWM (position weight matrix) of the postselection substrate libraries were also generated by WebLogo 3 (weblogo.threeplusone.com/create.cgi).

Example 2

Profiling Protease Specificity: Combining Yeast ER Sequestration Screening (YESS) with Next Generation Sequencing System Validation Negative and positive controls were run to validate the YESS-NGS approach (FIGS. 1A-C). For a negative control, a YESS substrate fusion construct was created without an exogenous protease but with a substrate sequence not expected to have an endogenous yeast cleavage site (the TEV-P cleavage sequence ENLYFQS (SEQ ID NO:8)). Antibody labeling following incubation yielded cells with equally high PE and FITC signals as expected for a substrate that is not cleaved (FIG. 1C). As a positive control for cleavage, a YESS substrate fusion construct was created incorporating a known Kex2 cleavage sequence, VARRD (SEQ ID NO:14; Bostian et al. 1984). As expected, yeast cells containing the VARRD (SEQ ID NO: 14) cleavage sequence displayed relatively high PE fluorescence and low FITC fluorescence in the FACS fluorescence scatter plots, indicating od proteolysis within the VARRD (SEQ ID NO: 14) sequence (FIG. 1c).

Understanding Background Cleavage: The Yeast Secretory CleaveOme

Figure 1B:
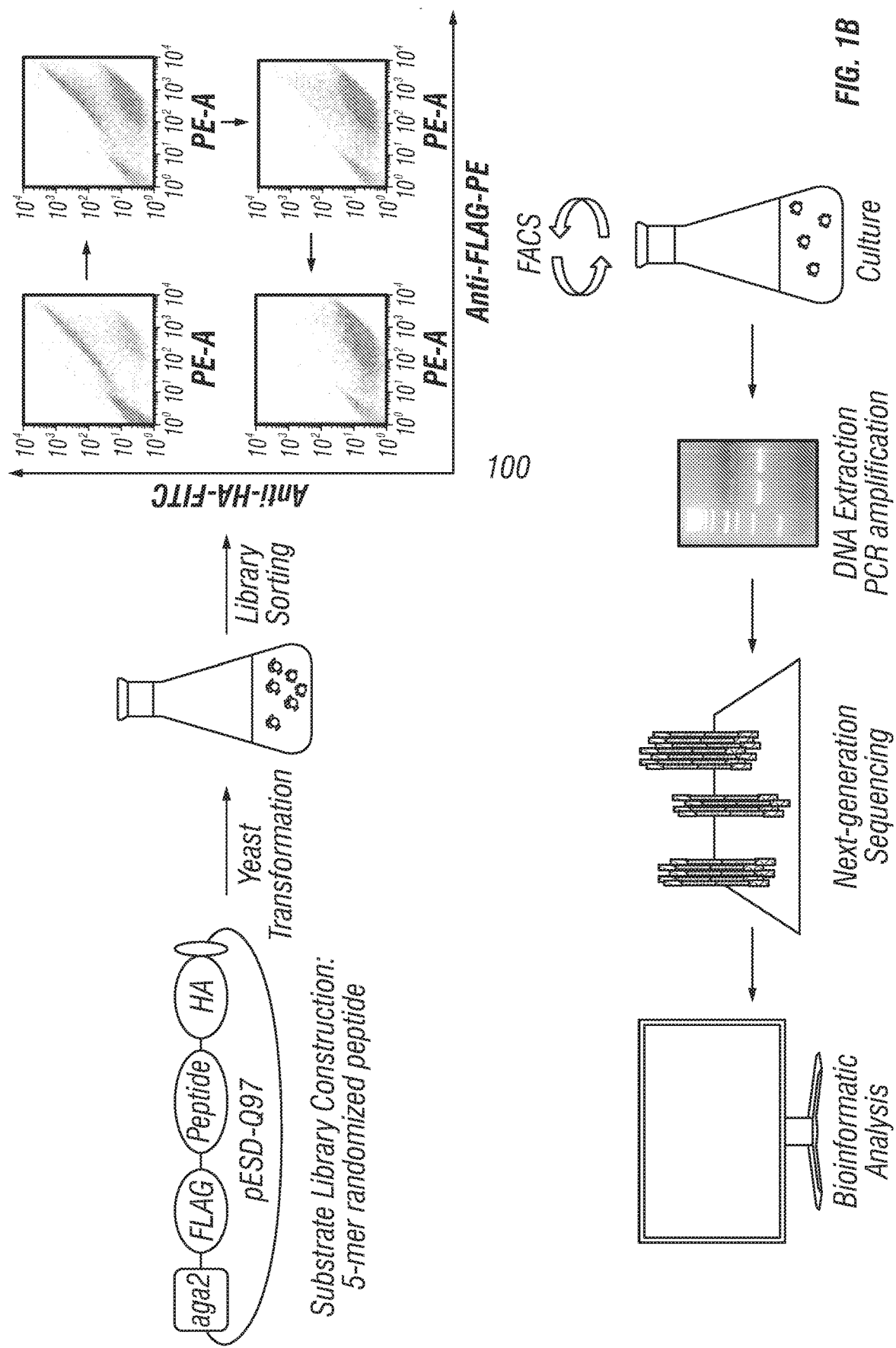
Figure 1C:
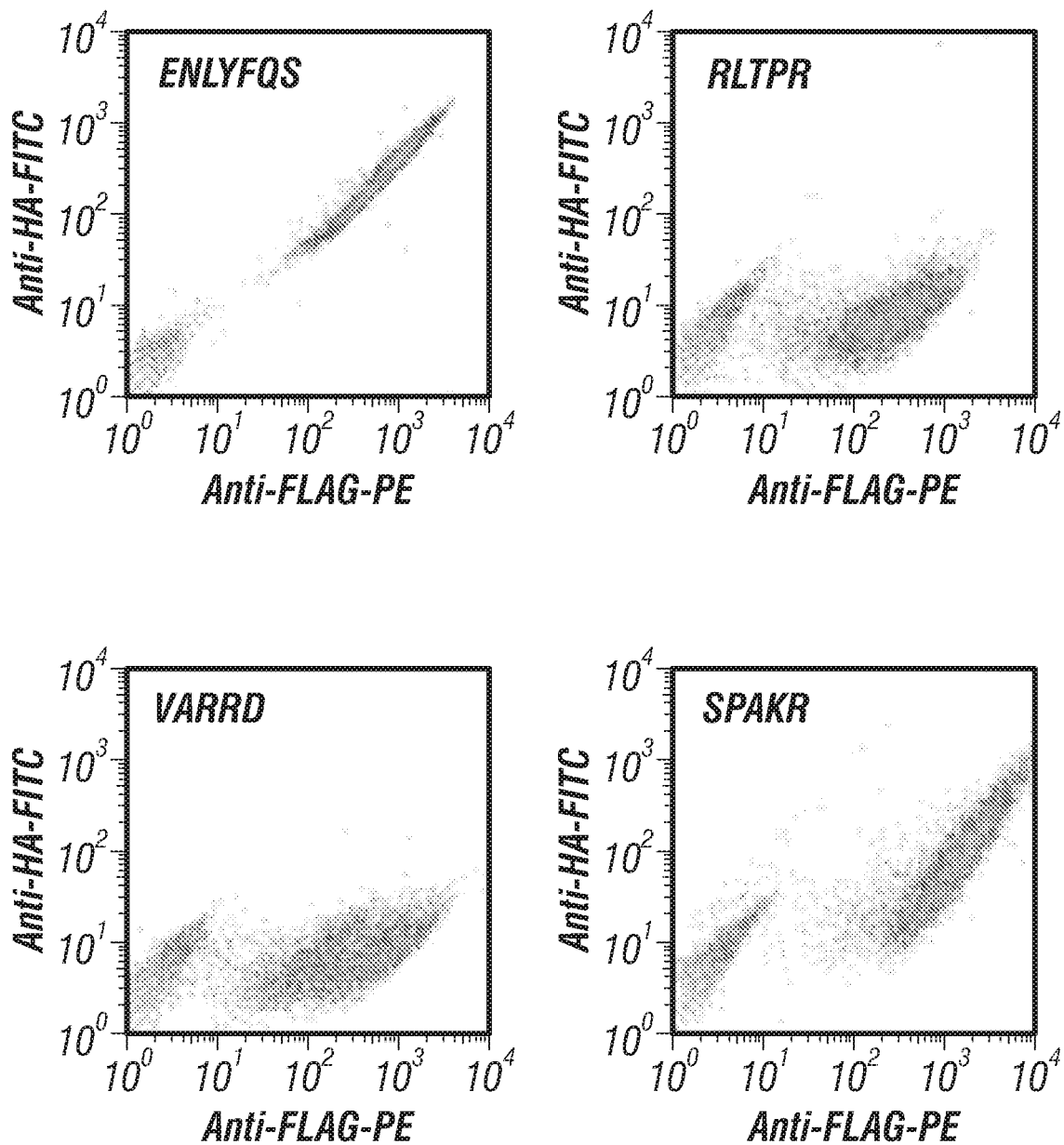

To characterize the endogeneous convertase cleaveOme in the yeast secretory pathway, a substrate library was prepared by combinatorial NNS randomization of five sequential amino acid positions within the substrate region of the reporting construct (labeled as "peptide" in FIG. 1A cartoon). A total of $3 \times 10^8$ cells were analyzed for the substrate library that has a theoretical diversity of $3.2 \times 10^6$ different members. Three consecutive rounds of FACS sorting for high PE and low FITC signal intensity yielded $8.5 \times 10^5$ DNA sequences. Recall that in analogy to the VARRD (SEQ ID NO:14) positive control sequence, this high PE and low FTIC signal is consistent with cleavage within the substrate region of the reporting construct. A total of $1.0 \times 10^7$ sequences from the same library were also analyzed before sorting to provide an accurate basis for comparative sequence analyses. For both libraries, isolated DNA fragments containing the substrate sequences were amplified and analyzed with a Hiseq NextGen DNA sequencer (Illumina).

Figure 2:
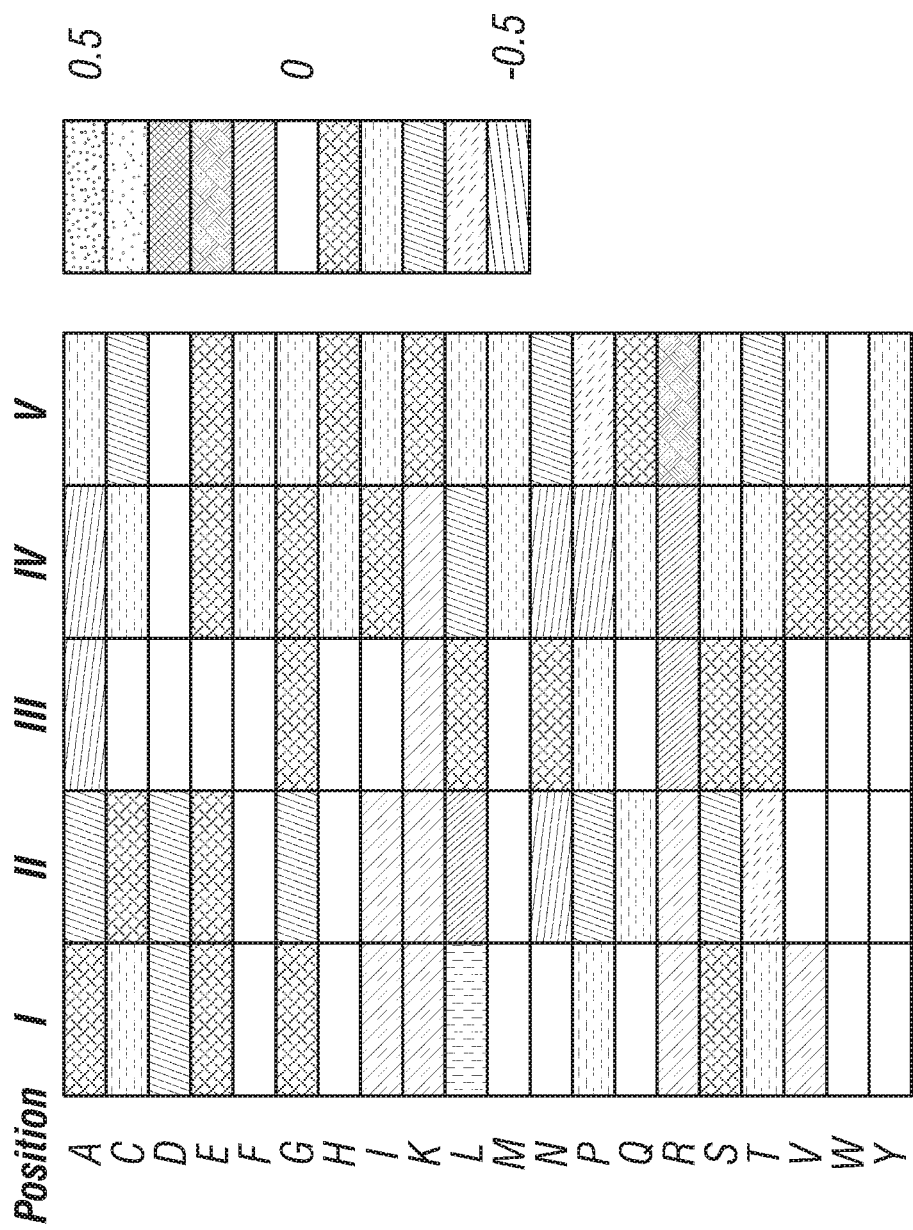
FIG. 2: Yeast Secretory Pathway Endopeptidase CleaveOme Specificity Profile. Heat map shows the specificity scores compiled from all sequences identified in selection. Specificity scores were calculated by dividing the change in frequency of the amino acid at each position in the postselection pool compared to the preselection pool by the maximal possible change in frequency from preselection library to postselection library of the AA at each position. Blue and red boxes indicate enrichment for and against an AA at a given position, respectively, as indicated by the color scale.

Increased prevalence, i.e. enrichment, of particular residues at any of the five randomized positions of the sorted library relative to the unsorted library was taken as evidence of enhanced representation within the cleaved substrates, indicated by blue color in FIG. 2. Conversely, several amino acids were found to be substantially deenriched following the FACS sorting, and these residues are shaded red in FIG. 2.

The greatest enrichments observed in the sorted library were for the basic residue Arg at positions III, IV and V, and the hydrophobic residue Leu at positions I and II. Note that the Roman numerals relate to the position of the substrate randomization, consisting of five consecutive positions, I-V, in the YESS substrate reporting construct. Enrichment for the basic residue Lys at positions III and IV was also seen, but not to the same extent as Arg. No patterns were identified when the sorted libraries were analyzed after excluding all sequences containing the basic residues Lys and Arg. The most significant deenrichment was seen at position II, with the small or hydrophilic residues Ala, Asp, Glu, Gly, Pro, Gln, Ser, and Thr experiencing the greatest deenrichment.

Figures 3A, 3B, 3C:
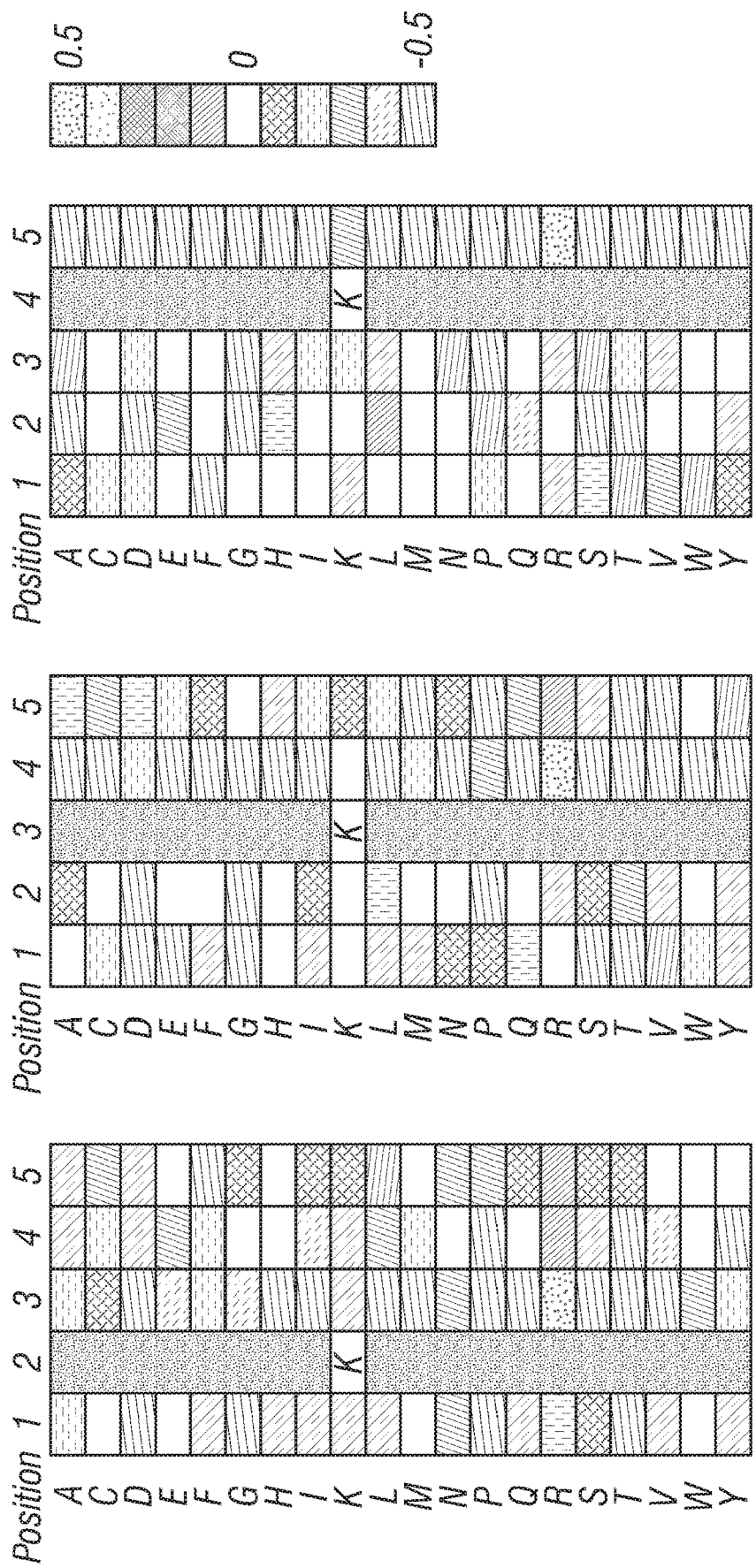
FIGS. 3A-I: Analysis of cleavage sequence patterns in the yeast secretory cleaveOme when selected sequences are filtered for the presence of a particular residue (indicated by gray bar) at one of the randomized positions labeled as I-V. Blue color indicates a strongly enriched residue in the cleaved/selected pool relative to the unsorted pool, while red indicates a residue that is strongly deenriched in the cleaved pool using the same scaling as in FIG. 2.

To identify positive linkages between residues in cleaved sequences, all selected sequences with a specific residue in a given position (i.e., Leu at position I, etc.) were examined for the presence of residues appearing at a frequency above background in any other positions. The known Lys/Arg-Arg specificity of Kex2 (MEROPS database accessible at merops.sanger.ac.uk) would predict that among the cleaved substrates, a strong enrichment for Lys/Arg-Arg would be found throughout the targeted area. This turned out to be the case. As can be seen in FIGS. 3A-C, when positions II, III, or IV were fixed as Lys, all amino acids immediately adjacent on the C-terminal side were strongly deenriched with the exception of Arg, which was strongly enriched, and Lys which was not deenriched or enriched. Lys at position I showed modest enrichment of Arg at the II position, but not at the level seen with Lys in positions II-IV. One possibility is that other residues, such as L at the N-terminal side of Lys-Arg, will facilitate the recognition of Lys-Arg by the endogenous protease (FIG. 3).

Figures 3D, 3E, 3F:
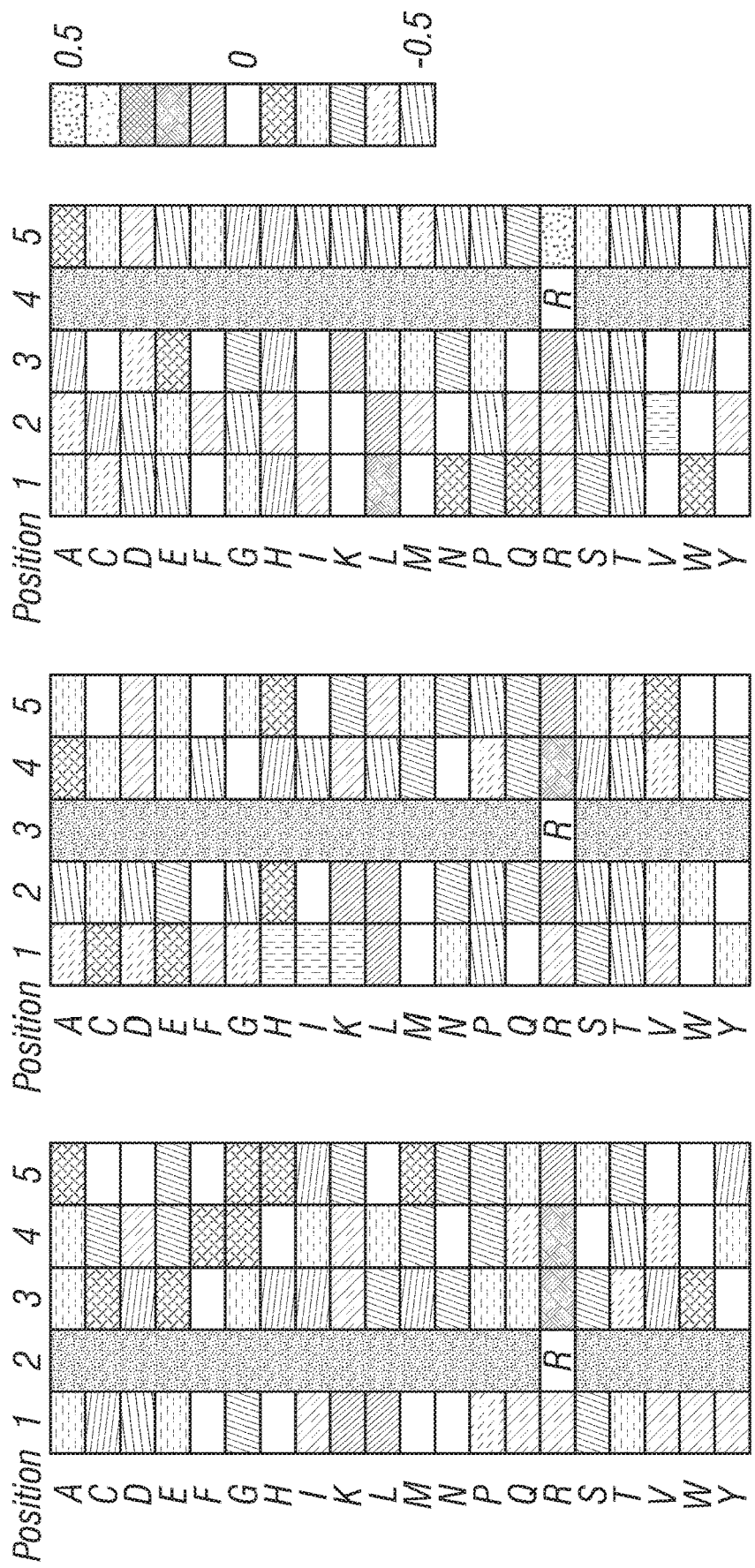
Figures 3G, 3H, 3I:
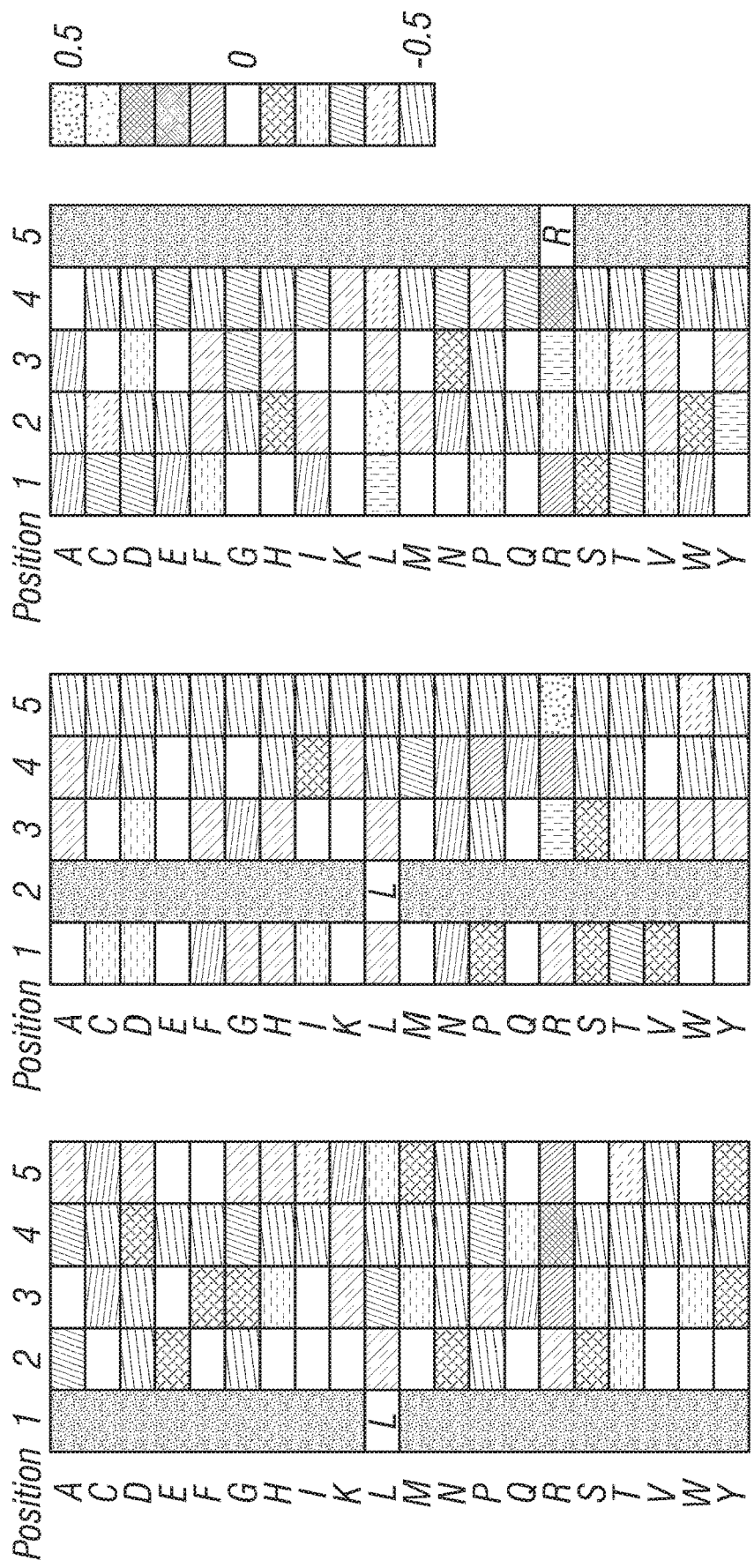
Figure 4A:
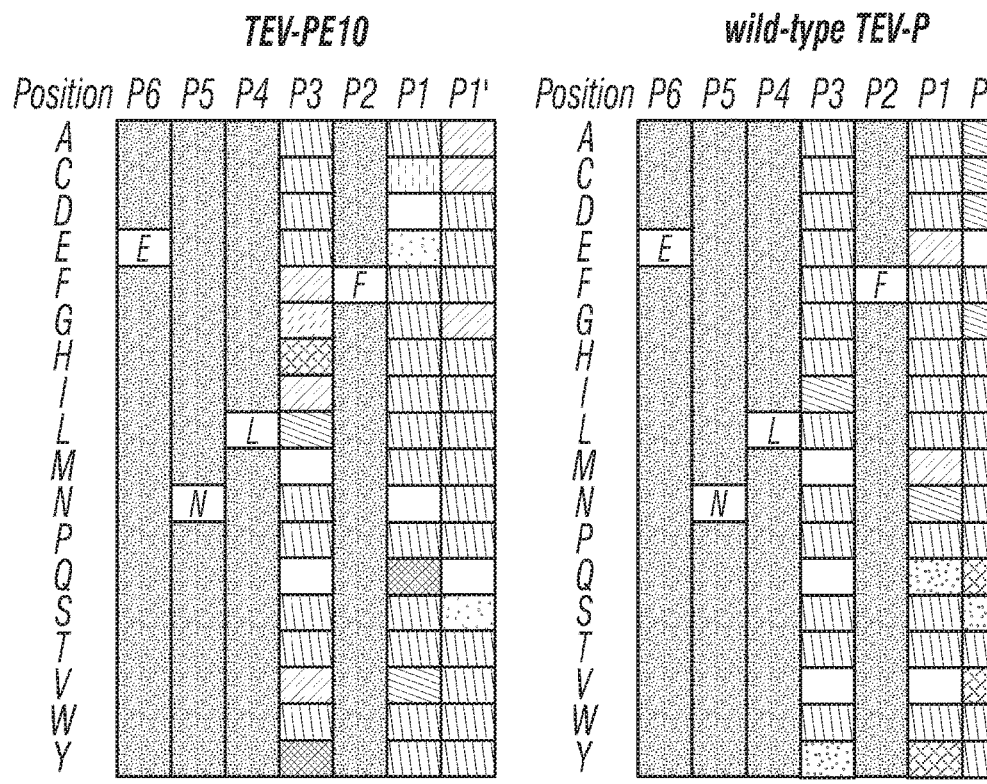
FIGS. 4A-D: Specificity profiles of engineered TEV-PE10 (left panels) and wide-type TEV-P (right panels) based on the substrate library being randomized at P1', P1, P3 and P6 within the substrate region, and mutation at position P6 with amino acid E (FIG. 4A) or position P3 with amino acid Y (FIG. 4B) or position P1 with amino acid E/Q (FIG. 4C) or position P1' with amino acid S (FIG. 4D).
Figure 4B:
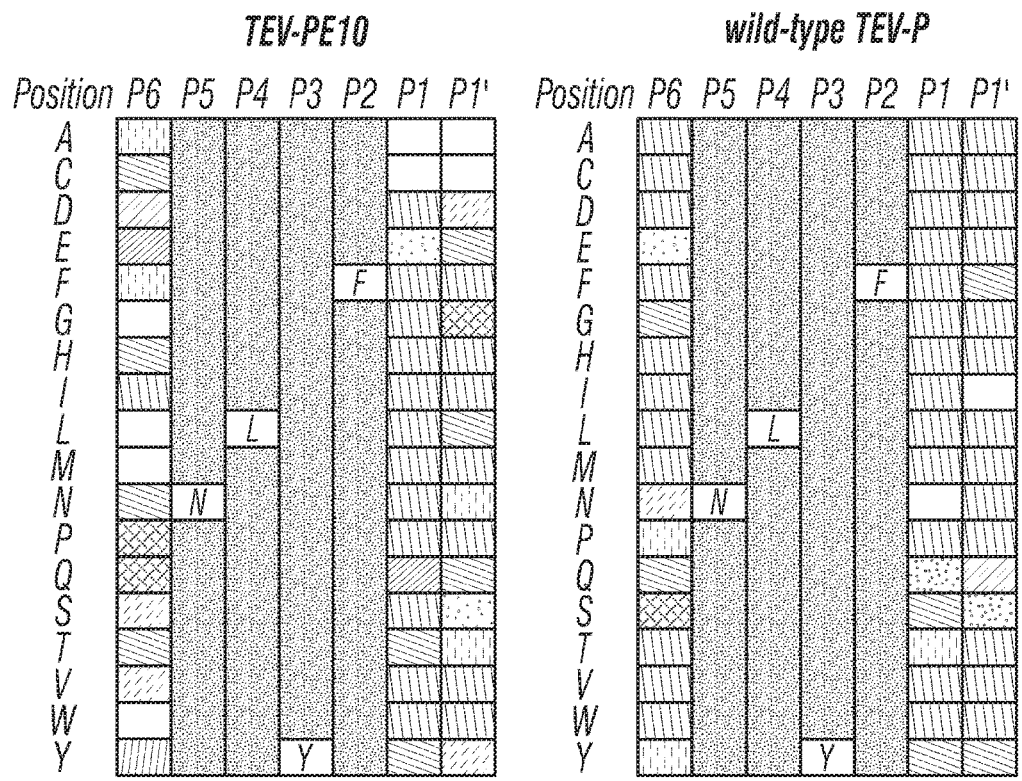
Figure 4C:
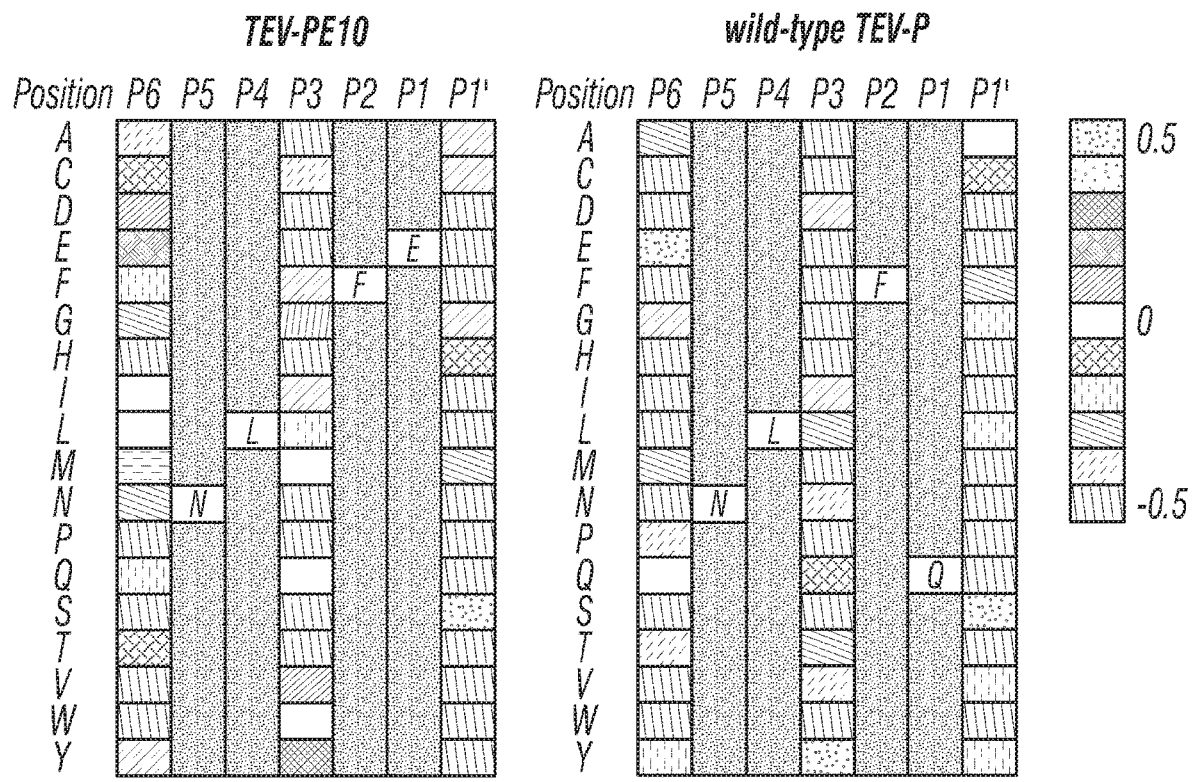
Figure 4D:
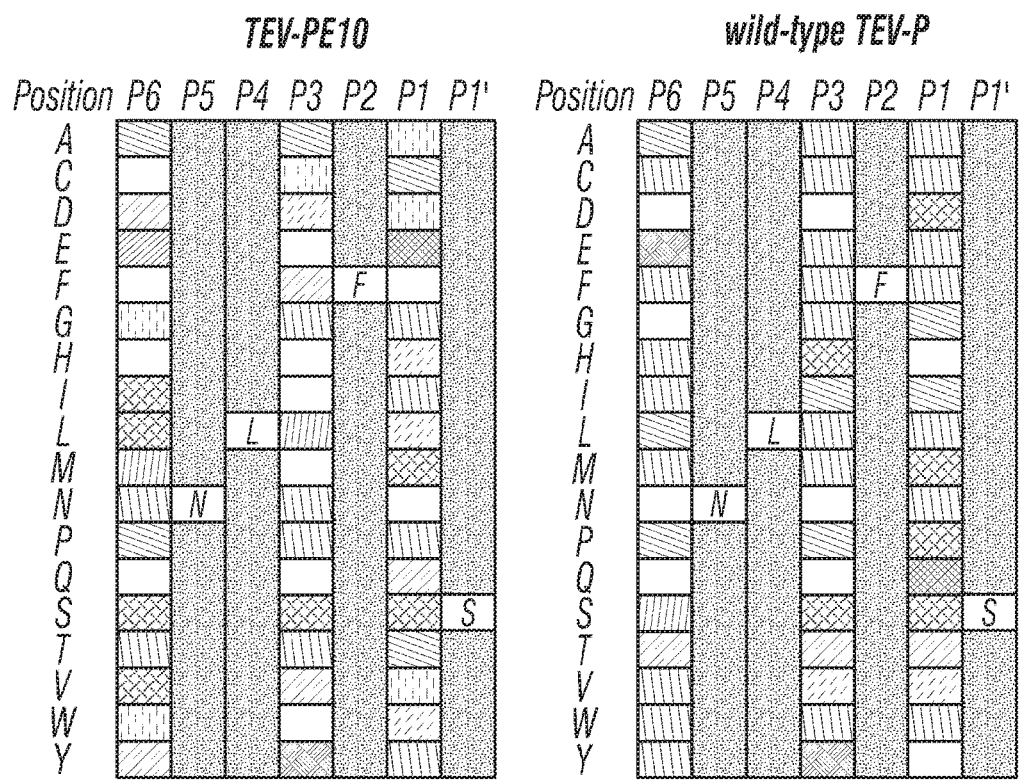

A related dibasic pattern exists for Arg at positions II-V, with Arg or Lys being enriched to the N-terminal side and usually Arg being enriched to the C-terminal side as well. Interestingly, Arg was observed to be enriched to some extent at all positions in these substrates indicating that the recognition might actually involve more of the mono-Arg or poly-Arg motifs rather than just Arg-Arg (FIGS. 3D-F). Note also that Arg is enriched overall to a greater extent than Lys (FIG. 2). Collectively, these data were interpreted to indicate the presence of a strong mono-Arg, Arg-Arg or possibly poly-Arg recognition pattern that is enriched more so than Lys-Arg. In addition, some other resides other than the Lys or Arg also contributed to the enrichment of Arg, such as Leu to the N-terminal side (FIGS. 3G-I). Interestingly, only a small amount of Lys-Lys and no Arg-Lys enrichment was detected in this analysis.

The highly enriched Leu residues in positions I and II (FIG. 2) are strongly linked to Arg residues later in the sequence. Filtering the data for all selected sequences containing Leu at position II shows significant enrichment for Arg at position V (FIG. 3H). In corresponding fashion, looking at all selected sequences containing Arg at position V reveals enrichment of Leu at position II (FIG. 3I). Similarly, the selected sequences with Leu at position I show a strong enrichment of Arg at position IV (FIG. 3G) and the selected sequences with Arg at position IV show enrichment of Leu at position I (FIG. 3F). What emerges from this analysis is a strong Leu-X-X-Arg (SEQ ID NO:54) pattern, and further analysis provides justification for extending this to be Ali-X-X-Arg (SEQ ID NO:55) in which Ali is Leu, Phe, Met, Ile and Val, although Leu is clearly the dominant residue found in the cleaved sequences. To validate the dibasic pattern and the Leu-X-X-Arg (SEQ ID NO:54) monoR pattern, four substrates were isolated and tested, which contained the amino acid sequences SPAKR (SEQ ID NO:32), LLCKR (SEQ ID NO:50), RLTPR (SEQ ID NO:31) and LQPRA (SEQ ID NO:51), respectively. The FACS results indicated that all of these substrates could be cleaved by the endogenous proteases in the yeast secretory pathway, while the cleavage of SPAKR (SEQ ID NO:32) is less efficient due to the Pro instead of Leu existing at position II.

Identification of Kex2 being the Major Endogenous Protease in Yeast CleaveOme Pathway The profiling of the sorted library clearly indicated significant enrichment of few residues, including Leu at positions I and II, and Arg at positions III, IV and V, which gave a representative pattern of LXXR (SEQ ID NO:54) (FIG. 2). In addition, Lys at positions III and IV, and Arg at positions I and II, were also enriched to a lesser extent, giving a representative K/RR dibasic pattern. Val was also slightly enriched at position I. However, it might be associated with Arg at its C-terminal side as no patterns were identified when Lys and Arg were excluded in the analysis. The K/RR dibasic peptide was known as a Kex2 substrate (MEROPS database accessible at merops.sanger.ac.uk), while the LXXR (SEQ ID NO:54) pattern and the association of Val with other residues were not previously reported. To further investigate these two major patterns, especially the LXXR (SEQ ID NO:54) pattern, the inventors generated a Kex2 knockout EBY100 strain (EBY100$^{Kex2-}$), and analyzed the top 20 substrates obtained after the sorting enrichments, respectively (Table 1).

In the top 20 substrates obtained after the three-rounds sorting enrichments, 15 out of 20 substrates contained the LXXR (SEQ ID NO:54) pattern, which all presented efficient cleavage in EBY100 and non-cleavage in EBY100$^{Kex2-}$, indicating that they are either directly recognized by the Kex2 or indirectly associated with Kex2 in the yeast secretory pathway. The other five substrates, ARKPA (SEQ ID NO:33), GSFRP (SEQ ID NO:34), NAFSH (SEQ ID NO:35), YPVCV (SEQ ID NO:52), and SPAWR (SEQ ID NO:53), presented non-cleavage in either EBY100 or EBY100$^{Kex2-}$, which might be caused by mutations or bias during the NGS sample preparation or sequencing. Three dibasic peptide substrates, VARRD (SEQ ID NO:14), SPAKR (SEQ ID NO:32), and LLCKR (SEQ ID NO:50), were evaluated in both EBY100 and EBY100$^{KEX2-}$ strains (FIG. 1C). All three substrates exhibited cleavage in EBY100 and non-cleavage in EBY100$^{Kex2-}$, confirming the recognition of K/RR dibasic peptide by Kex2 in yeast cells. In addition, RLTPR (SEQ ID NO:31) and LQPRA (SEQ ID NO:51) were also evaluated, with efficient cleavage in the EBY100 and non-cleavage in the EBY100$^{Kex2-}$ strain, respectively (FIG. 1C). The non-cleavage of RLTPR (SEQ ID NO:31) and LQPRA (SEQ ID NO:51) in the EBY100$^{Kex2-}$ strain suggests correlation of the LXXR (SEQ ID NO:54) pattern with Kex2.

Analysis of Recombinant Protease Specificity

The combined YESS-NGS approach was next used to profile the sequence specificities of two recombinant proteases: wild-type (TEV-P) and an engineered variant (TEV-PE10:S120R, D148R, T173A, N177K, M218I) (Yi et al. 2013) of the tobacco etch mosaic virus (TEV) protease. Being previously engineered using the YESS system, TEV-PE10 exhibited a 5000-fold increase in reactivity (as k/Ku) for a peptide substrate containing Glu at P1 instead of the wild-type preferred Gin.

To profile the substrate specificity of wild-type TEV-P as well as TEV-PE10, a sequence encoding wild-type TEV-P or TEV-PE10 was introduced into the protease side of the YESS vector downstream of the GAL1 promoter. An abbreviated substrate library was generated by NNS randomization of four residues corresponding to the P1', P1, P3 and P6 positions on the reporter construct side of the same YESS vector. Positions P2, P4 and P5 were fixed to be Phe, Leu and Asn, respectively, consistent with wild-type preferences at these positions (Dougherty et al. 1988). After three rounds of FACS sorting for high PE and low FITC signal intensity, the enriched libraries were isolated, the DNA fragments encoding the substrate sequences were amplified then analyzed using Hiseq NextGen DNA sequencing (Illumina). A large unsorted aliquot of the same library served as a reference. As before, sequences found to be enriched after sorting based on comparison to the unsorted reference were assumed to have undergone protease cleavage. In order to overcome the background signal from the endogeneous convertase cleaveOme in the yeast secretory pathway, sequences were excluded that contained the amino acids Lys and Arg. The exclusion of Lys and Arg had very little affects to the final sequence profiling results, as Lys and Arg were not tolerated at P position based on the previous study (Dougherty et al. 1988).

The overall specificity profiles of recombinant TEV proteases revealed that, as expected, wild-type TEV-P selectively recognizes Gln (Q) at P1 while the engineered TEV-PE10 variant prefers Glu (E) at P1. Both recombinant TEV proteases exhibited strong preferences at P1', P3, or P6 for Ser (S), Tyr (Y), or Glu (E), respectively. To further deconvolute the positional correlations within the substrate profiles of recombinant TEV proteases, the specificity profiles were analyzed by looking at only selected sequences that contained a particular amino acid at one of the randomized positions (indicated by the grey boxes in FIGS. 4A-D). Consistent with the overall specificity profiles, significant enrichments of the ENLYFQS (SEQ ID NO:8) sequence were observed for the wide-type TEV-P and ENLYFES (SEQ ID NO:1) sequence for the engineered TEV-PE10 (FIGS. 4A-D). Note that while TEV-PE10 did appear to cleave substrates with Gln at P1 to some extent, no detectable enrichment was seen for Glu at P1 with TEV-P.

The bottom line is that by far the most important change in specificity observed among the P1', P1, P3 and P6 residues is that TEV-P prefers Gln, while TEV-PE10 prefers Glu at P1. The other three positions examined appeared similar or identical in specificity between the two, indicating that the engineered TEV-PE10 maintained a specificity profile that is only altered at the P1 position relative to wild-type. This is consistent with previous research that TEV-PE10 was obtained through engineering TEV-P against the ENLYFES (SEQ ID NO:1) sequence (Dougherty et al. 1988). No other residues were enriched to a significant extent at any of the randomized positions when cleaved by either protease. Further, the TEV-PE10 specificity for Glu at P1 is not the result of relaxed specificity at that position, but represents a genuine alteration of specificity in favor of Glu while retaining some activity for Gln, as no other amino acids are enriched at P1.

The extent of enrichment or deenrichment observed in these analyses may not necessarily have a strictly linear correlation to protease substrate preference; nonetheless, these data are qualitatively consistent with previous quantitative data on the TEV protease. For example, other factors beyond protease catalytic rates such as relative representation in the original library might influence the absolute amount of enrichment observed, making quantitative comparisons within data less reliable. It is therefore very notable that a previous quantitative analysis with individual peptide substrates different only at P1 indicated TEV-P displayed a roughly 380-fold preference for Gln relative to Glu, while TEV-E10 exhibited a roughly 13-fold prefence for Glu relative to Gln. These measured values track in a relative way with the data in FIGS. 4A-D in which some enrichment of P Gln substrates is noted with TEV-E10, but no enrichment of P1 Glu substrates is seen with TEV-P. These two conclusive examples support the hypothesis that this enrichment data obtained using YESS combined with NextGen sequencing and a comparative sequence analysis is qualitatively in-line with actual protease catalytic preferences.

Discussion

By combining the YESS protease engineering platform technology with NextGen sequencing and comparative sequence analysis, the endogeneous convertase cleaveOme in the yeast secretory pathway was mapped within living cells for the first time. At least two and possibly three distinct substrate patterns were identified. Specificities for both Arg-Arg and Lys-Arg were clearly present. The results indicated that they are not cleaved in the EBY100$^{Kex2-}$ strain, revealing their correlation with the Kex2. However, it is still not known whether these specificities directly correspond to Kex2 or other different proteases that were activated by the Kex2 in yeast secretory cleaveOme. It is worth pointing out that the data do not rule out the mono-Arg and poly-Arg recognition that may or may not be related to the dibasic recognition. Besides the K/RR dibasic peptide pattern, an entirely independent consensus of Leu-X-X-Arg (SEQ ID NO:54) was also revealed to be related to the Kex2 in yeast cells. No patterns were identified when basic residues were excluded from the sequences being examined. The implication is that basic residues, especially Arg, are crucial to recognition by all the major proteases of the yeast secretory cleaveOme.

At this point, not all of the observed consensus cleavage patterns can be correlated with certainty to specific proteases in the yeast convertase cleavOme. The observed dibasic pattern is consistent with the known Kex2 substrate preference for dibasic sites, especially Lys-Arg, and these results support the idea that the presence of many sequences in the enriched pool to Kex2 cleavage. In fact, there are some indications that Kex2 prefers Lys-Arg over Arg-Arg (MEROPS database accessible at merops.sanger.ac.uk), in contrast to the relative enrichments observed in the studies in which Arg-Arg was found to predominate. Although the substrate analysis of VARRD (SEQ ID NO:14) and SPAKR (SEQ ID NO:32) in the EBY100$^{Kex2-}$ strain indicated that they are Kex2 related, it is still conceivable that one or more other proteases might participate with or influence specificity for dibasic Arg-Arg or Lys-Arg. The analysis of the ARKPA (SEQ ID NO:33) and VARRR revealed that they were not cleaved in the EBY100$^{Kex2-}$ strain, which suggested that the substrate pattern for Kex2 may be more complicated than merely either KR or RR. In addition, the RRRRR was also found to be only cleaved in the EBY100 and not in the EBY100$^{Kex2-}$, indicating the correlation of ploy-Arg pattern with Kex2.

Besides Kex2 that was identified in this research, other proteases such as the yapsins, could be related to the Ali-X-X-Arg (SEQ ID NO:55) consensus pattern. The yeast homologue YPSI (also known as YAP3, peptidase 3.4.23.41), was reported to prefer Lys or Arg at P1(MEROPS database accessible at merops.sanger.ac.uk; Bourbonnais et al. 1993; Cawley et al. 1996; Gagnon-Arsenault et al. 2006; Komano et al. 1999; Komano et al. 1998; Ledgerwood et al. 1996; and Olsen et al. 1999). Although known to be accepted at the P4 position, there is no known strong preference for Leu at P4 by any of the yapsin family of proteases. Therefore, at this point there is no persuasive reason to assign the Ali-X-X-Arg (SEQ ID NO:55) pattern to either Kex2 or yapsin cleavage (MEROPS database accessible at merops.sanger.ac.uk). Further analysis of other yeast knockout strains besides EBY100$^{Kex2-}$ will be helpful to identify with certainty the proteases involved in the secretory cleavOme.

Yeast cells have been widely used for recombinant protein production, however, proteolytic degradation of the recombinant protein of interest has been a perpetual problem (Sinha et al. 2005). It is possible that the cleaveOme identified by this method could be applied to develop computational models to predict the potential cleavage sites in the proteins when transporting in the yeast secretory pathway. This information is particularly important for those using yeast display technology, as library members with dibasic or Ali-X-X-Arg (SEQ ID NO:55) patterns are likely being removed from screens without researcher's knowledge.

The combined YESS-NextGen approach was used to evaluate the sequence specificity of the wild-type TEV-P and an engineered variant TEV-PE10 of the tobacco etch mosaic virus protease in EBY100. This method may be extended to other recombinant or engineered proteases. Beyond just confirming the different specificities at P1 that were previously identified using individual peptide substrates, the data reported here verify that P1 preference represents the only significant difference in specificity between TEV-PE10 and TEV-P (Phan et al. 2002). This latter conclusion could only be reached with certainty following an exhaustive substrate specificity analysis enabled with a truly comprehensive method such as that reported here.

Here, the substrate profiling for TEV-P and TEV-PE10 were performed in the EBY100 instead of EBY100$^{Kex2-}$ cells. Unfortunately, the EBY100$^{Kex2-}$ was generated and identified after the substrate profiling experiments. Although it is a better host cell than the original EBY100, the final profiling results are barely affected by Kex2 in the yeast secretory pathway. All the substrate profiling data were subtracted by the naïve library background, and Lys and Arg were excluded from the final sequencing data (see the Materials and Methods), which minimized the side effects brought by the endogenous protease, such as Kex2, in the yeast CleaveOme. The substrates recognized by the endogenous proteases were not added to the substrate database of TEV-P and TEV-PE10. However, by subtracting the substrates recognized by the endogenous proteases, the related information was lost, which decreased the size of the original substrate library. Without wishing to be bound by any theory, the decreased size appears to be negligible as only 0.25% size of the original library will be lost if it is presumed that all LXXR (SEQ ID NO:54) sequences could be efficiently cleaved. Considering that the substrates identified in the results that could be cleaved by the endogenous proteases in yeast were all Arg related, the effects on the TEV-P substrate profiling are further minimized as TEV-P has been well characterized that it does not tolerate Arg at P1 position (Dougherty et al. 1988). More importantly, these substrate profiling results indicate that the best substrates for TEV-P and TEV-PE10 are ENLYFQS (SEQ ID NO:8) and ENLYFES (SEQ ID NO:1), respectively, which are well matched with the previously published results (Yi et al. 2013).

Defining substrate specificity with greater precision will be increasingly important as engineered proteases are developed for more sophisticated applications including therapies (Li et al. 2013). Having a comprehensive substrate profiling capability within the YESS protease engineering platform can be used to facilitate the rapid identification and full characterization of engineered proteases with desirable cleavage activities.

Example 3

Analysis of Sequence Specificity of Sortase a from *S. pyogenes* Via Yeast ER Sequestration Screening Sortases can be utilized for various biotechnological applications including the ligation of various proteins to molecular probes, nucleic acids, glycans and solid supports. For C-terminal labeling, the protein to be labeled contained the sortase sorting sequence (LPETG, SEQ ID NO:15, for *S. Aureus* SrtA) and the probe contained a di-glycine amino terminus for ligation. N-terminal labeling may also occur if the probe contains the sorting signal and the protein contains the poly-glycine motif. Sequence specificity can differ for various sortases across the different classes of sortases, as well as across species of gram-positive bacteria.

This example provides, in some aspects, techniques for analyzing the sequence specificity of various sortases utilizing the yeast ER sequestration screening technique, employing SrtA from *S. pyogenes* as a proof of principal. This class of sortase recognizes the sorting signal LPETA/G (SEQ ID NO:30) and can ligate either poly-alanine or poly-glycine probes.

In the positive control construct (FIGS. 5A-B), the sorting signal (LPETA, SEQ ID NO:29) of SrtA *S. pyogenes* was fused to the C-terminal end of the yeast adhesion receptor subunit Aga2 within the pESE plasmid. This fusion contained two antibody tag sequences and enabled the labeling of cells with the following fluorescently labeled antibodies: a six-histidine (6×His) tag to probe total Aga2 expression on the yeast cell surface, and a FLAG antibody tag (DYKDDDDK, SEQ ID NO:9) located downstream of the LPETA (SEQ ID NO:29) sorting signal to probe LPET/A cleavage during the transpeptidation reaction. This construct was under control of the galactose (GAL) induced GAL1 promoter, located within the GAL1-GAL10 bidirectional hybrid promoter. SrtA from *S. pyogenes* (residues 81-249) was cloned into the vector under control of the GAL10 portion of the GAL1-GAL10 promoter. The small stable B-lymphocyte antigen, CD20, was inserted elsewhere on the plasmid under control of a separate GAL1 promoter. CD20 was used as a ligation probe with the poly-alanine tag at the N-terminus and an HA antibody tag (YPYDVPDYA, SEQ ID NO:20) at the C-terminus to label for transpeptidation activity. All induced proteins (Aga2 fusion, SrtA and CD) also contained an N-terminal ER targeting sequence (MQLLRCFSIFSVIASVLA, SEQ ID NO:3) and a C-terminal ER retention sequence (FEHDEL, SEQ ID NO:4). The negative control construct is the same as the positive control, but with the SrtA gene removed. Negative and positive control plasmids are shown in FIGS. 5A-B.

Figure 6A:
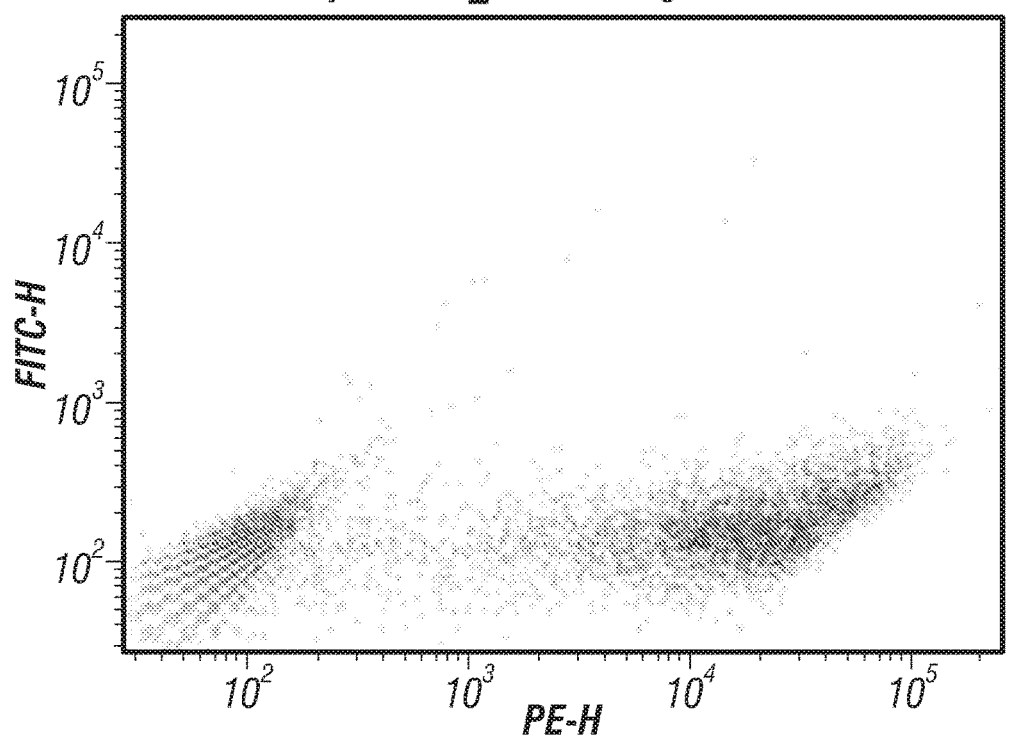
FIGS. 6A-B.
Figure 6A:
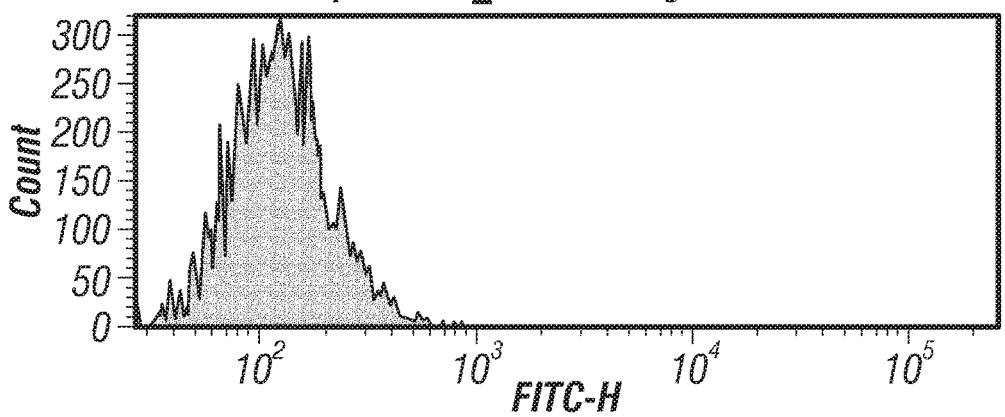
Figure 6A:
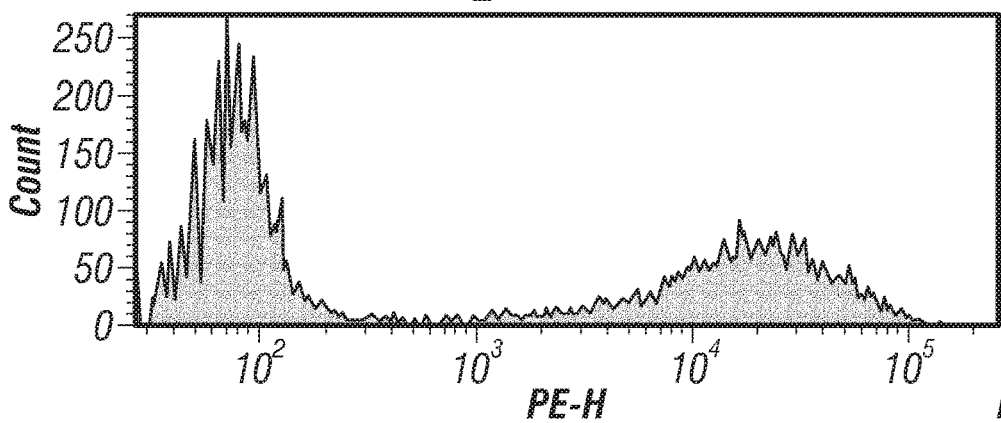
Figure 6B:
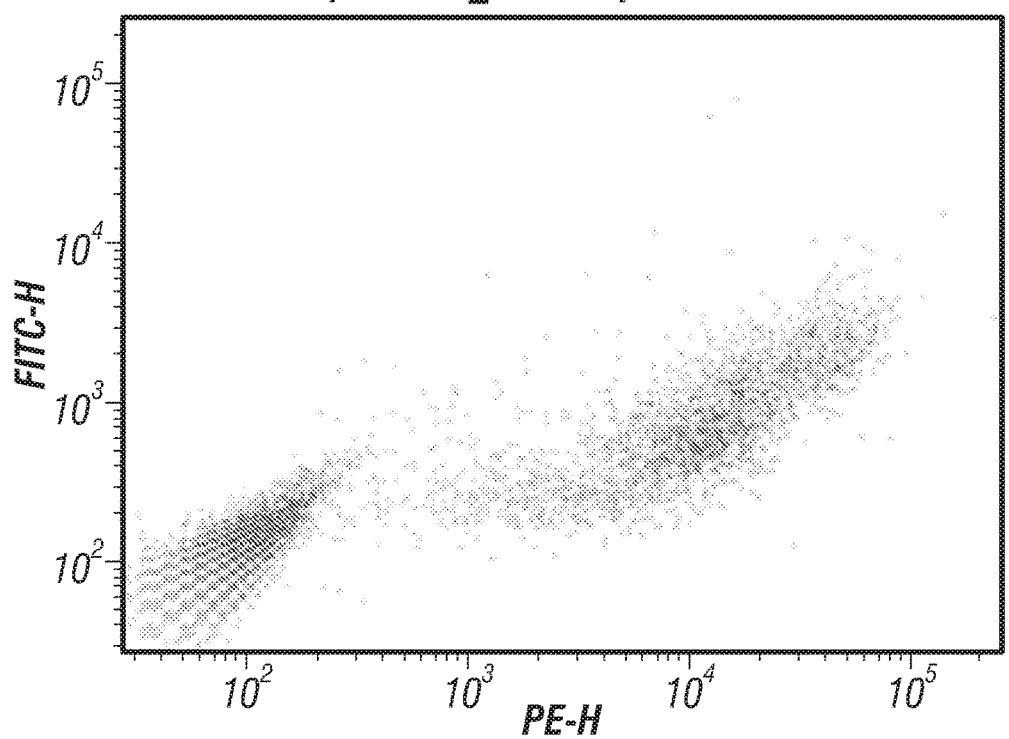
Figure 6B:
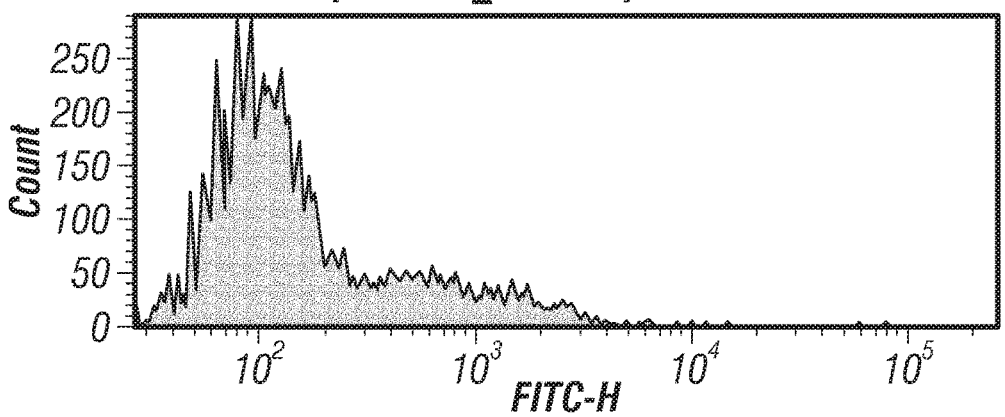
Figure 6B:
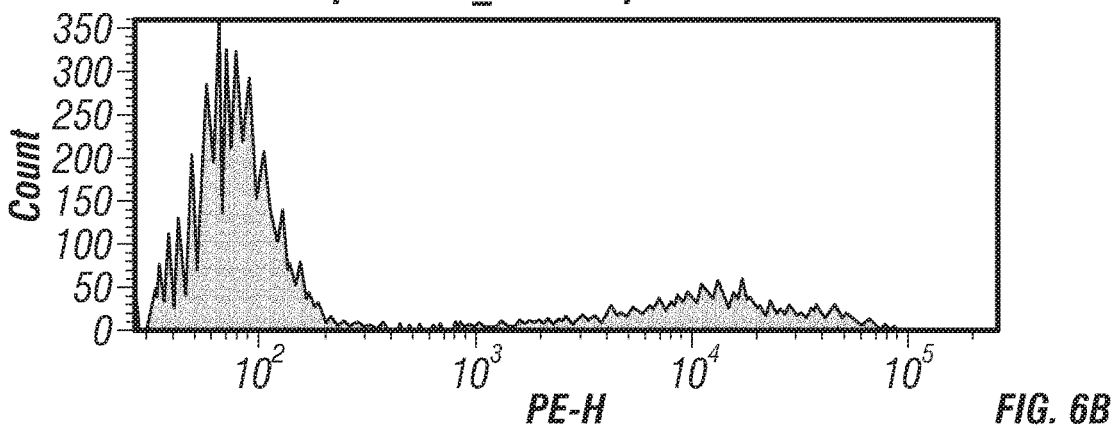
Figure 7:
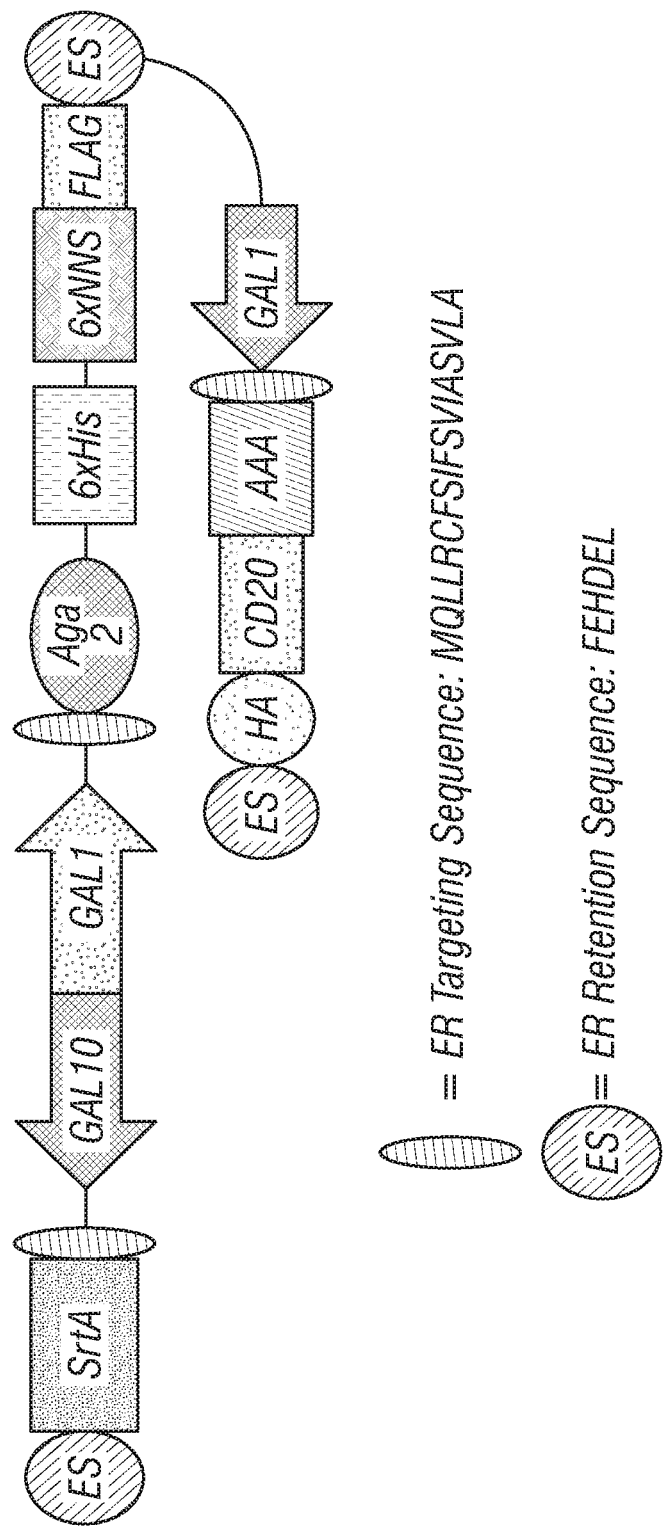
FIG. 7: 6×NNS library plasmid construct.
Figure 8:
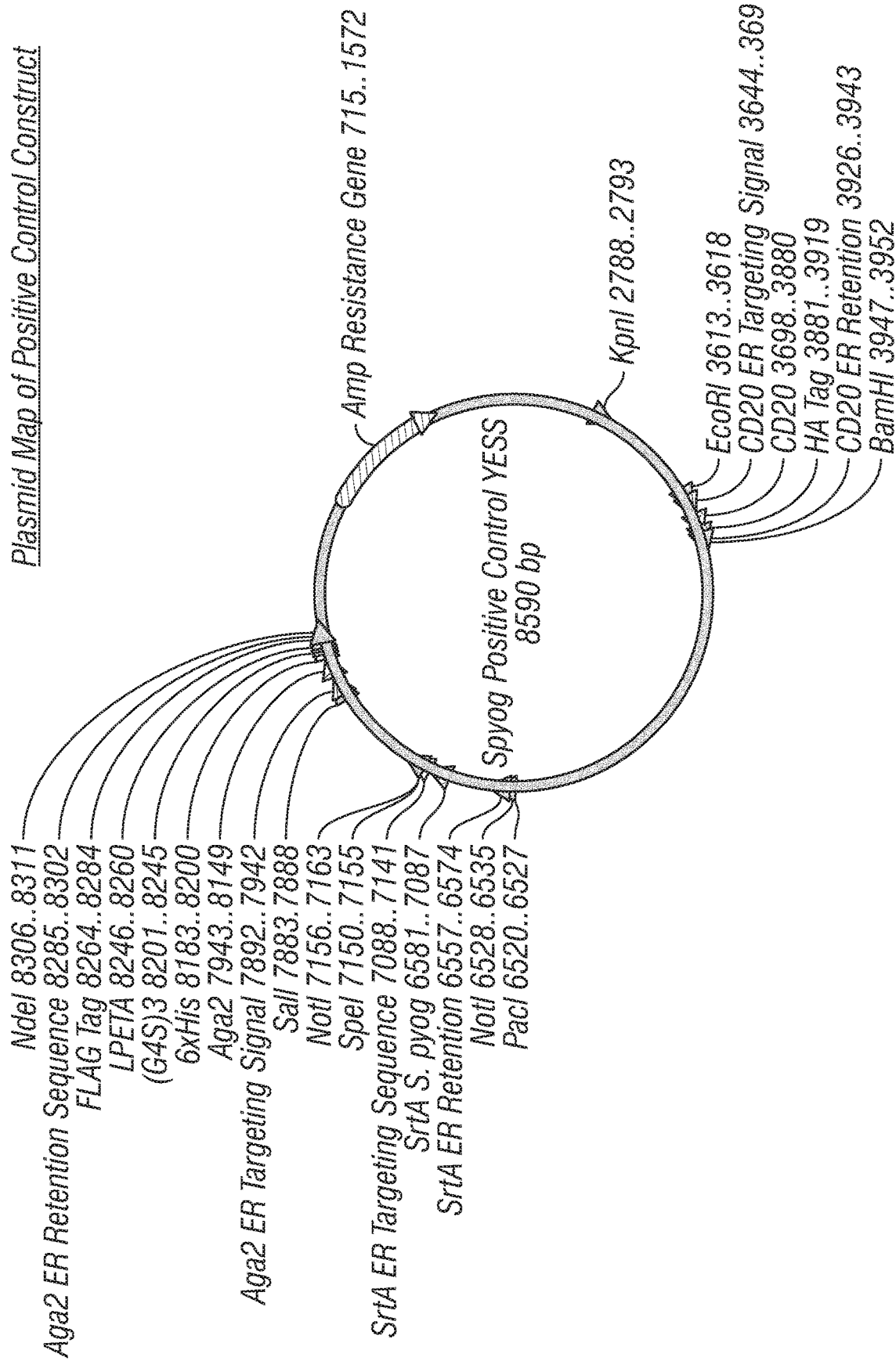
FIG. 8: Plasmid map of positive control construct.

Upon induction with galactose of the positive control plasmid construct, all proteins can be targeted to the ER lumen via the ER targeting signal. This signal is cleaved upon entry to the ER, resulting in a poly-alanine N-terminus for the CD20 construct. SrtA cleaves between the Thr-Ala of the LPETA (SEQ ID NO:29) sorting signal, releasing the Ala-FLAG-ER retention sequence fusion and generating the acyl-enzyme intermediate. This intermediate is resolved by nucleophilic attack by the amine of the N-termini poly-alanine-CD20-HA construct. A positive signal resulted in an increase in HA-FITC signal and decrease in FLAG-PE signal (FIG. 6B), in comparison to the negative control (FIG. 6A). Information about sequence specificity SrtA for the sortase signal can be obtained by generating a 6×NNS library, where N can be adenine (A), guanine (G), thymine (T), or cytosine (C) and S is either C or G, in place of the LPETA (SEQ ID NO:29) sorting signal FIG. 7.

The positive and negative control plasmids were transformed into chemically competent EBY100 cells and grown on YNB-CAA plates (5 g/L casamino acids, 6.7 g/L yeast nutrient broth, 20 g/L glucose, 15 g/L agar) at 30° C. Resulting colonies were grown in 5 mL SD-UT media (100 mM sodium phosphate, pH 5.8, 5 g/L casamino acids, 6.7 g/L yeast nutrient broth, 20 g/L glucose) overnight at 30° C., with shaking at 250 rpm. $5 \times 10^7$ cells were centrifuged at 500×g and resuspended in 5 ml SG-UT (5 g/L casamino acids, 6.7 g/L yeast nutrient broth, 20 g/L galactose, 15 g/L agar) for a final OD600=1. Cells were induced for up to 24 hours at 30° C. $5 \times 10^6$ cells were centrifuged, washed with PBS buffer containing 0.5% BSA and labeled with anti-HA-FITC (0.02 μg/μL final concentration) and anti-FLAG-PE (0.01 μg/μL final concentration) antibodies for 1 hour at a cell density of 105 cells/μL. Antibody labeled cells were washed with PBS buffer and analyzed by a BD Biosciences FACS Aria flow cytometer. Antibody labeled cells were excited by a 488 nm laser and read with 575/30 nm and 510/20 nm emission filters. 10,000 events were recorded. These results indicate that these approaches can successfully be applied to sortases.

Example 4

Kinase Specificity Profiling by Yeast Endoplasmic Reticulum Sequestration Screening (YESS)

Yeast endoplasmic reticulum sequestration screening (YESS) was used for the simultaneous expression and co-localization of a protein-modifying enzyme and its substrate, followed by cell-surface display of the substrate. Co-expression was achieved by inserting the enzyme and substrate genes downstream of the Gal10 and Gal1 inducible promoters, which are arranged in a tail-to-tail fashion on the plasmid. The N-termini of the proteins contained a signal sequence which directs the protease and substrate to the endoplasmic reticulum (ER). At the C-terminus of the proteins, the ER-retention signal peptide (FEHDEL, SEQ ID NO:4) causes the protein and its substrate to be co-localized in the lumen of the ER. By fusing the substrate sequence with the Aga2 protein, as in preceding yeast display technologies, the substrate is trafficked to the outer membrane of the cell, where it is displayed via disulfide bonding to the lipid-anchored membrane protein Aga1.

Figure 9:
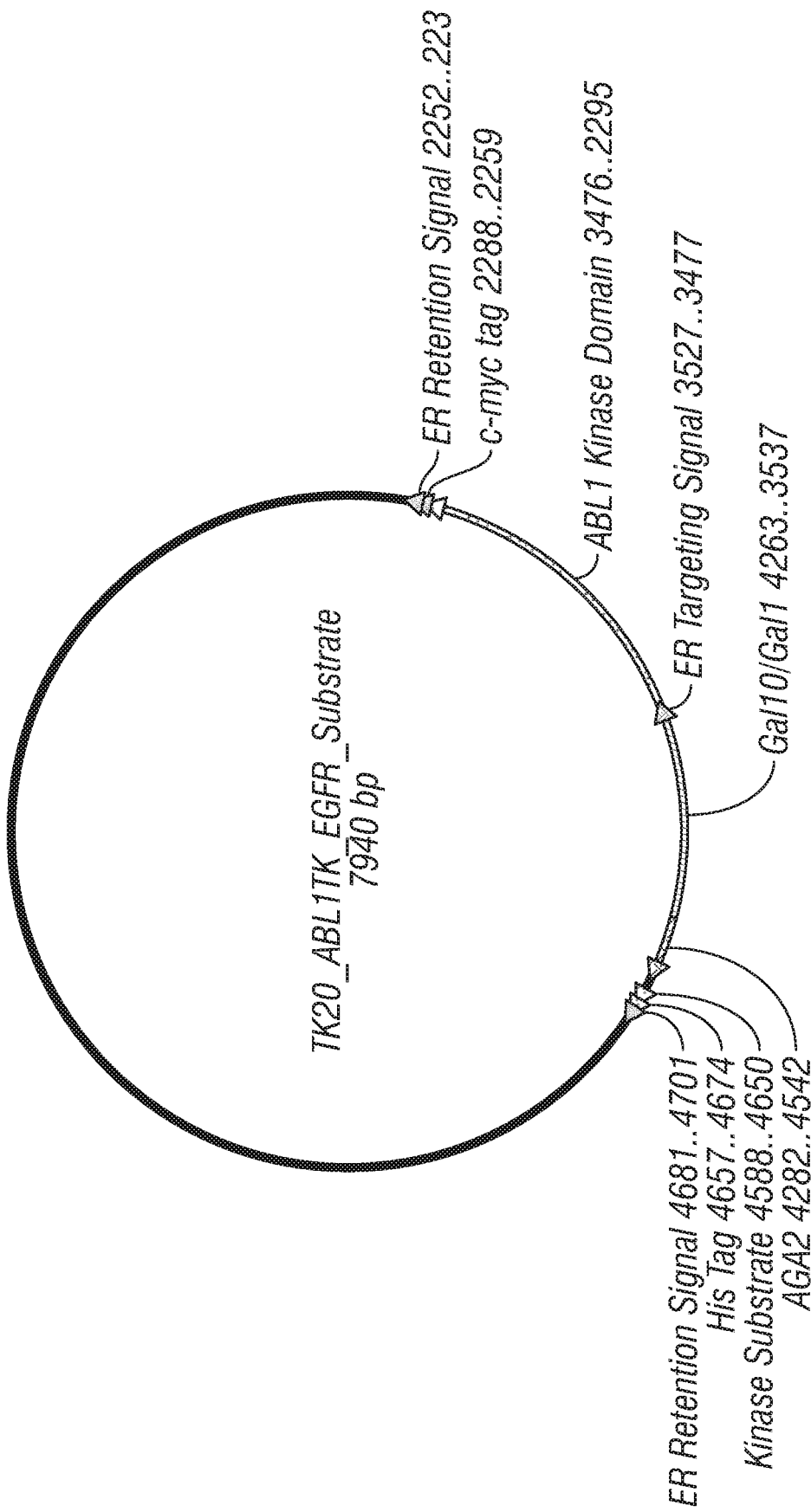
FIG. 9: Plasmid map of plasmid encoding the Abl1 tyrosine kinase and kinase substrate.
Figure 10:
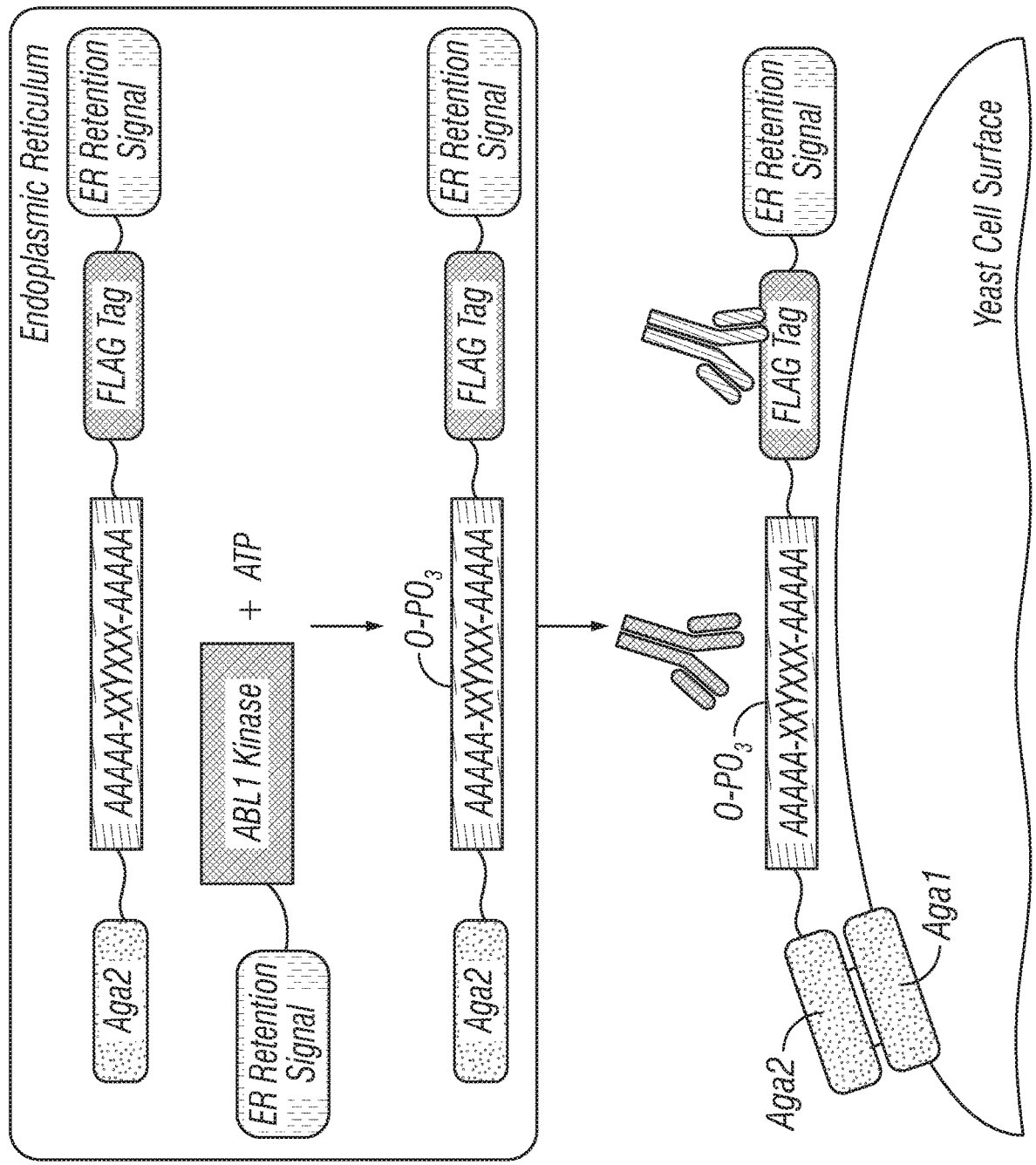
FIG. 10: Overview of approach used for detection of phosphorylation of a substrate by a kinase.

The YESS system was used to screen large numbers of unique substrates for phosphorylation by a kinase. First, a large diversity of substrate-encoding DNA sequences was produced by polymerase chain reaction (PCR) with degenerate codon primers. Next, yeast was co-transformed with plasmid DNA containing the kinase and promoters and the unique substrate-encoding DNA. Due to homology between the ends of the substrate and plasmid DNA sequences, the endogenous yeast homologous recombination pathway produces an intact circular plasmid upon transformation. This process resulted in a population of yeast cells wherein each contains a single substrate-encoding DNA sequence along with the kinase of choice under galactose promoters. The plasmid encoding the Abl1 tyrosine kinase and kinase substrate is shown in FIG. 9. A general overview of the approach is shown in FIG. 10.

After an initial outgrowth phase in glucose-containing medium, protein production was induced by growth in galactose-containing medium at 20 degrees C. for 42-48 hours. During this phase, the kinase and putative substrate was co-expressed and co-localized in the endoplasmic reticulum, allowing the phosphorylation reaction to occur. Subsequent surface display of the substrate-Aga2 fusion allowed for detection by fluorophore-labeled antibodies. Phosphotyrosine-specific antibodies (e.g., 4G10, PY20) were used to discriminate between cells with active substrates and those without. C-terminal to the substrate is a hexahistidine tag, allowing detection of the substrate-Aga2 fusion to verify expression and surface display.

Fluorescence Activated Cell Sorting (FACS) was used to enrich the population for cells containing active substrates. After incubating the population with fluorophore-labeled anti-phosphotyrosine antibody and anti-hexahistidine antibody, cells which were stained with both fluorophores were considered to have phosphorylated substrate tyrosines on the surface of the cell. This process of growth, induction, and enrichment by FACS (a "round") was repeated up to six times. After each round's FACS step, a number of cells exceeding the population's diversity was sampled for DNA sequencing.

For each round (including the initial unsorted library), plasmid DNA was isolated from the pool of yeast cells. The substrate-encoding gene was amplified using a "barcode" primer, which introduces a unique DNA sequence upstream of the substrate gene. This barcode allows pooled DNA from all rounds to be properly assigned after high-throughput sequencing. A full run on the Illumina MiSeq instrument with 250 base-pair paired-end reads yielded approximately 18 million DNA sequences, corresponding to 9 million unique sequences.

Sequence processing was begun by trimming low-quality sequences. Next, the antisense reads (opposite strand of the substrate gene's reading frame) were discarded due to redundancy with the sense-strand reads. Sequences were assigned to their round of origin based on the five nucleotide barcode from the amplification step. Finally, the DNA sequences were translated into amino acid sequences.

Amino acid frequencies and co-frequencies at each of the randomized positions were calculated and compiled into a database. "Enrichment" was calculated by dividing the frequency of an amino acid at a position by its frequency in the unsorted library. This number suggests the preference for a given amino acid at a position. Positive enrichment results in a value greater than 1, while negative enrichment (or depletion) results in a value between 0 and 1.

In the case of ABL kinase, a more detailed analysis revealed that amino acid frequencies vary based on their neighbor's identity. For instance, when glutamate is fixed at position Y-1 (immediately N-terminal to the phosphorylated tyrosine), the enrichment of glycine at position Y-2 nearly doubles, while the enrichment of aspartate at Y-2 is cut in half. To build a model accounting for this co-variation, the frequency of each amino acid-position combination was calculated in the context of one or two other amino acid-position combinations. This model was then be queried by submitting a 6-mer amino acid sequence with tyrosine in the third position. The frequency of each amino acid-position combination was multiplied, along with the co-frequencies of every possible di- and tri-amino acid combination. This overall frequency was calculated from both the post-sorted pool and the unsorted pool. Dividing the post-sorting frequency value by the pre-sorting frequency value results in a ratio of the frequencies. Logarithmic transformation of this ratio produces a "Likelihood Score", where positive values indicate the sequence was more likely to be found in the post-sorting pool than the pre-sorting pool, and vice versa.

Figure 11:
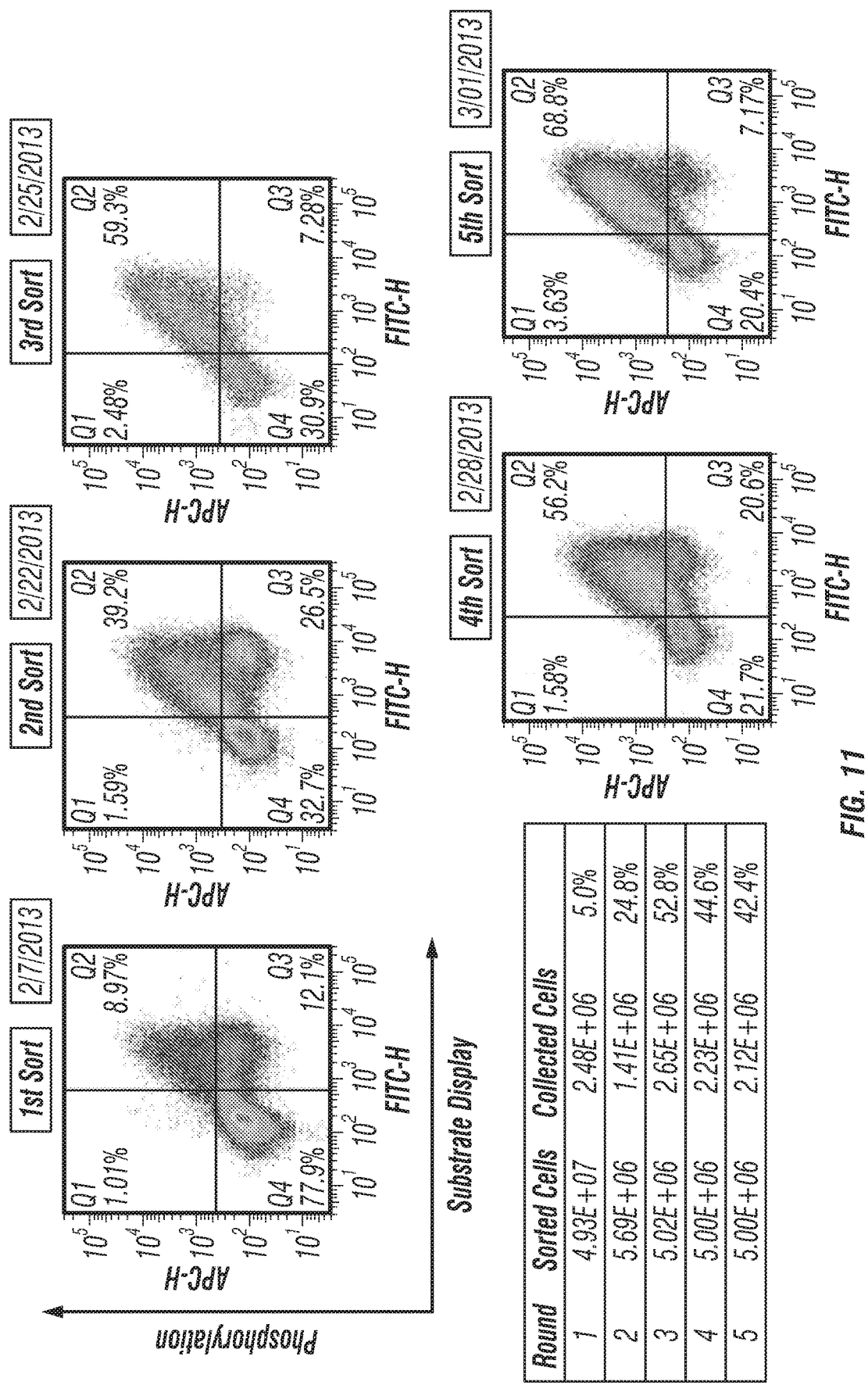
FIG. 11: Results from Abl1 kinase profiling.
Figure 12A:
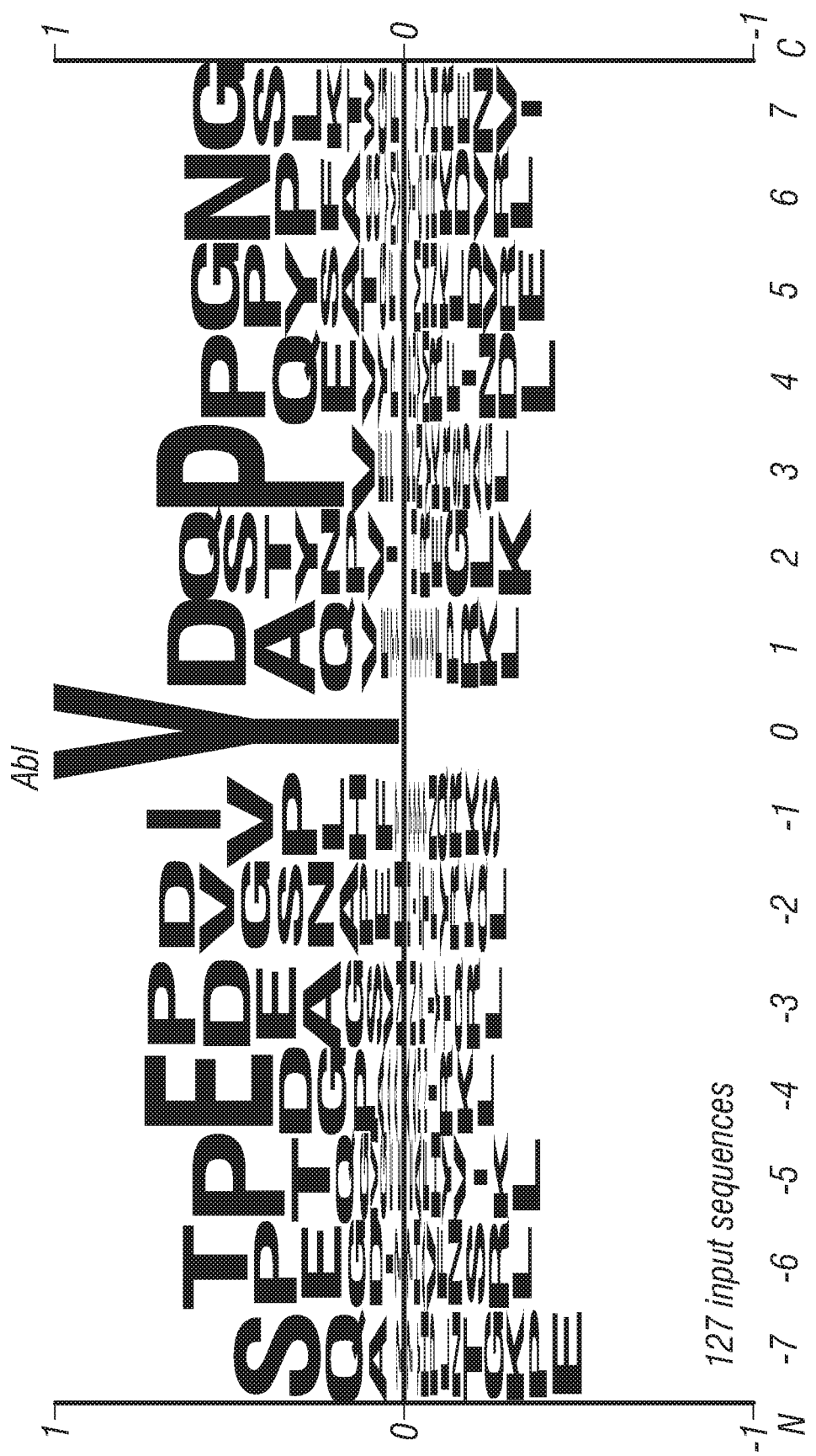
Figure 14:
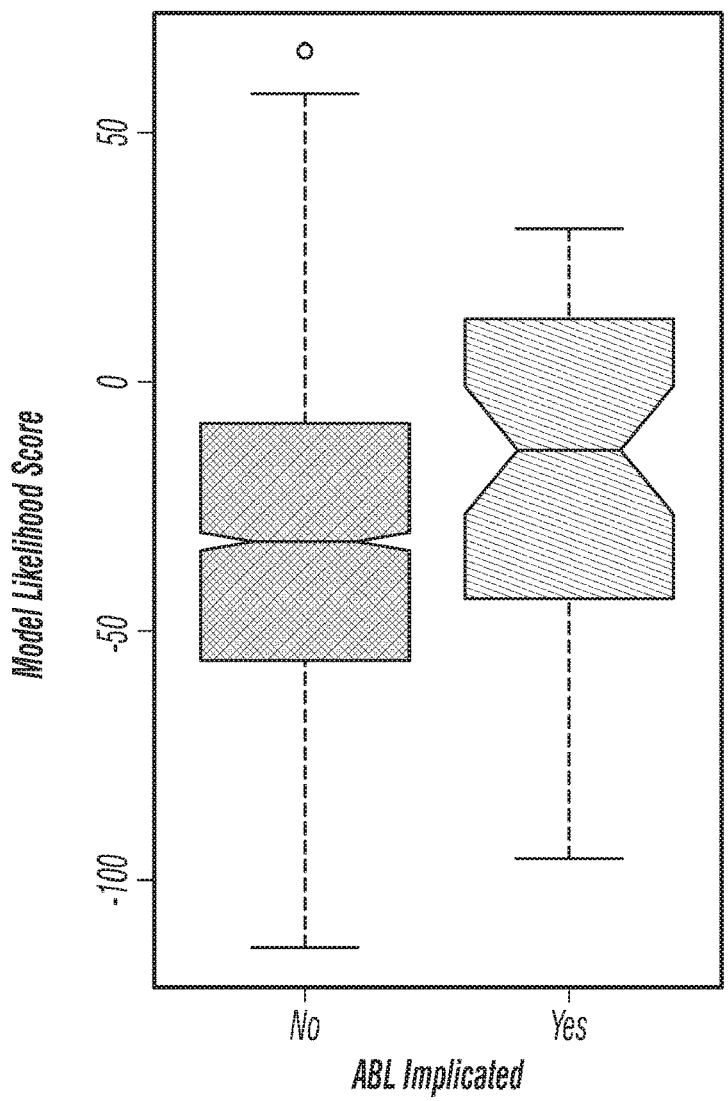
FIG. 14: Likelihood Calculations and Scoring the Human Phosphoproteome. (Above) The likelihood score of a sequence is calculated from the probabilities of each permutation of two-residue combinations. (below) The scores of known ABL1 substrates is significantly higher than the general population of phosphorylated tyrosines.
Figure 15:
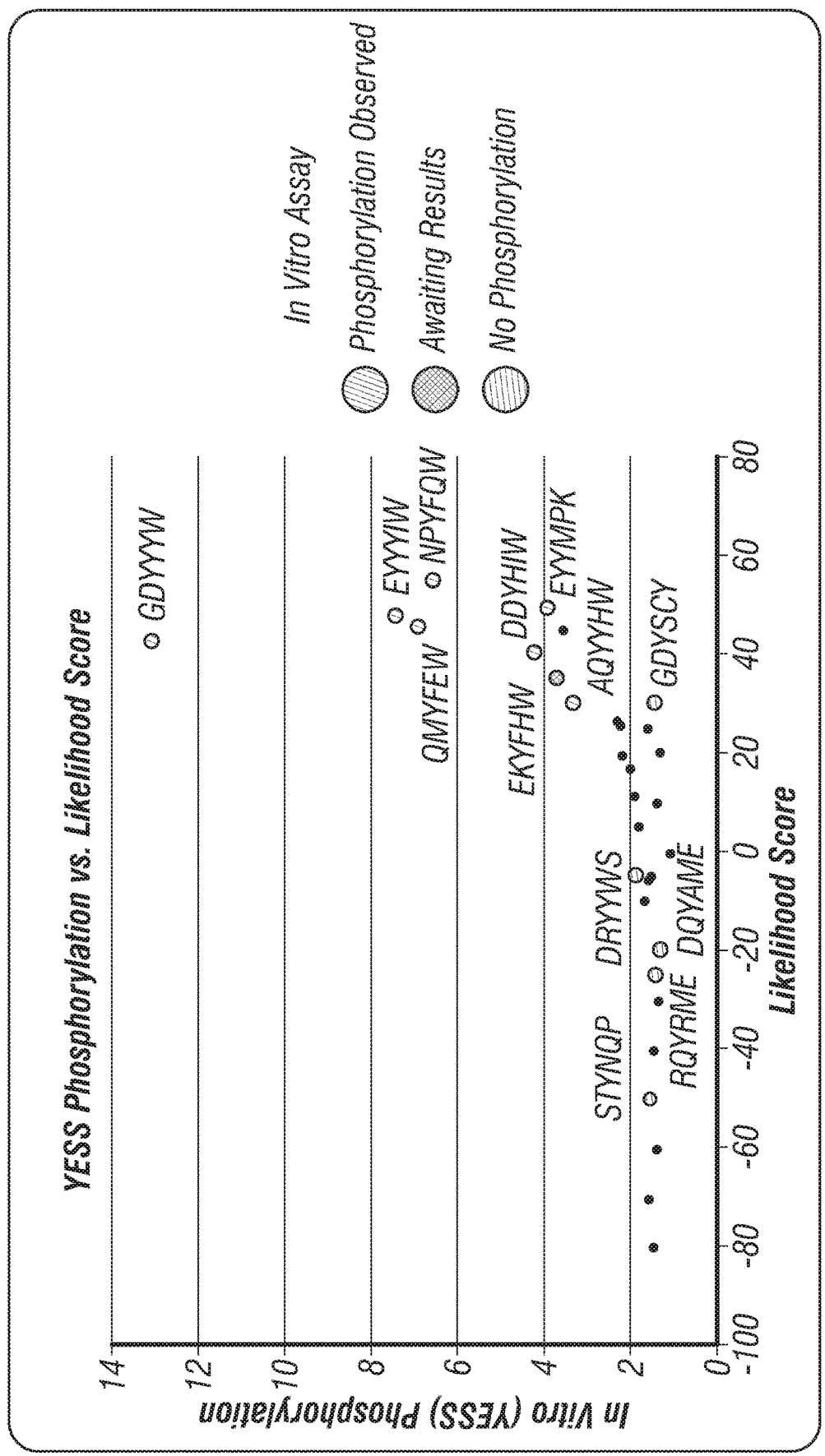
FIG. 15: Model Validation by YESS analysis of individual substrates and in vitro phosphorylation of synthetic peptides. 32 individual peptides, with scores ranging from −80 to +55 were individually analyzed in the YESS system. Results validated the likelihood score's prediction capability. 28 of these 32 peptides were not recovered from any round of screening. In vitro assays were performed with synthetic peptides and product formation was analyzed by MALDI-TOF and LC-ESI. (SEQ ID NO: 56=GDYYYW; SEQ ID NO: 57=EYYYIW; SEQ ID NO: 58=QMYFEW; SEQ ID NO: 59=NPYFQW; SEQ ID NO: 60=EKYFHW; SEQ ID NO: 61=DDYHIW; SEQ ID NO: 62=EYYMPK; SEQ ID NO: 63=STYNQP; SEQ ID NO: 64=DRYYWS; SEQ ID NO: 65=AQYYHW; SEQ ID NO: 66=RQYRME; SEQ ID NO: 67=DQYAME; SEQ ID NO: 68=GDYSCY)

Thirty-two peptides were selected based on this Likelihood Score, ranging from the highest score (+55) to the lowest score (−80). These sequences were then individually cloned into the YESS system. FACS analysis verified that only highly favored peptides (Likelihood>30) were phosphorylated. In addition, 26 of these peptide sequences were not recovered from the high-throughput DNA sequencing experiment, indicating that the model had produced novel predictions which had been validated. Furthermore, in vitro experiments verified that of a selection of five peptides, only those with a high likelihood score (>30) were phosphorylated by ABL kinase. Results are shown in FIG. 11. Sequence analysis was performed as shown in FIG. 12 and FIG. 13. Likelihood calculations and scoring the human phosphoproteome are shown in FIG. 14. As shown in FIG. 15, this model was observed to accurately predict which peptides would be phosphorylated, as confirmed by experiments using the YESS approach for detection of phosphorylation of synthetic peptides.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,826,364
U.S. Pat. No. 4,284,412
U.S. Pat. No. 4,498,766
U.S. Pat. No. 4,554,101
U.S. Pat. No. 4,661,913
U.S. Pat. No. 4,714,682
U.S. Pat. No. 4,767,206
U.S. Pat. No. 4,774,189
U.S. Pat. No. 4,857,451
U.S. Pat. No. 4,897,268
U.S. Pat. No. 4,989,977
U.S. Pat. No. 5,075,109
U.S. Pat. No. 5,160,974
U.S. Pat. No. 5,478,722
U.S. Pat. No. 5,552,157
U.S. Pat. No. 5,565,213
U.S. Pat. No. 5,567,434
U.S. Pat. No. 5,738,868
U.S. Pat. No. 5,795,587
WO 2008/137475
WO 2014/004540 (PCT/US2013/047663)
Aharoni et al., *Chem. Biol.*, 12(12):1281-1289, 2005. Arber et al. (1992).

Aridor, M., and Hannan, L. (2000) Traffic jam: a compendium of human diseases that affect intracellular transport processes, Traffic (Copenhagen, Denmark) 1, 836-851.

Aridor, M., and Hannan, L. (2002) Traffic jams II: an update of diseases of intracellular transport, Traffic (Copenhagen, Denmark) 3, 781-790.

Beinfeld, M. (1998) Prohormone and proneuropeptide processing. Recent progress and future challenges, Endocrine 8, 1-5.

Benatuil et al., *Protein Eng. Des. Sel.*, 23(4):155-159, 2010.

Boder and Wittrup, 1997.

Bostian, K., Elliott, Q., Bussey, H., Burn, V., Smith, A., and Tipper, D. (1984) Sequence of the preprotoxin dsRNA gene of type I killer yeast: multiple processing events produce a two-component toxin, Cell 36, 741-751.

Boulware, K. T. and Daugherty, P. S. (2006) Protease specificity determination by using cellular libraries of peptide substrates (CLiPS), Proc. Nat. Acad. Sci., USA 103, 7583-7588.

Bourbonnais, Y., Ash, J., Daigle, M., and Thomas, D. (1993) Isolation and characterization of *S. cerevisiae* mutants defective in somatostatin expression: cloning and functional role of a yeast gene encoding an aspartyl protease in precursor processing at monobasic cleavage sites, The EMBO journal 12, 285-294.

Cawley, N., Chen, H., Beinfeld, M., and Loh, Y. (1996) Specificity and kinetic studies on the cleavage of various prohormone mono- and paired-basic residue sites by yeast aspartic protease 3, The Journal of biological chemistry 271, 4168-4176.

Chanalia et al., *Rev. Med. Microbiol.*, 22(4):6, 2011.

Chen et al. (2011).

Chao et al., *Nat. Protoc.*, 1(2):755-768, 2006.

Collen and Lijnen, *Blood*, 78(12):3114-3124, 1991.

Copic et al. (2009).

Craik et al., 2011.

Denecke et al. (1992).

Diamond, S. (2007) Methods for mapping protease specificity, Current opinion in chemical biology 11, 46-51.

Dix, M. M., Simon, G. M., Cravatt, B. F., (2008) Global Mapping of the Topography and Magnitude of Proteolytic Events in Biological Systems, Cell 134, 679-691

Dougherty et al., *Embo J.*, 7(5):1281-1287, 1988.

Dougherty and Parks, *Virology*, 172145, 1989.

Dougherty et al., *Virology*, 172:302, 1989.

Drag and Salvesen, *Nat. Rev. Drug Discov.*, 9:690-701, 2010.

Drummond et al., *J. Mol. Biol.*, 350(4):806-816, 2005.

Gagnon-Arsenault, I., Tremblay, J., and Bourbonnais, Y. (2006) Fungal yapsins and cell wall: a unique family of aspartic peptidases for a distinctive cellular function, FEMS yeast research 6, 966-978.

Gai et al., *Curr. Opin. Struct. Biol.*, 17:467-473, 2007.

Gera et al., *Methods*, 2012 (Epub ahead of print))

Girard, V., Dieryckx, C., Job, C., and Job, D. (2013) Secretomes: The fungal strike force, Proteomics 13, 597-608.

Gould and Tawfik, *Biochemistry*, 44(14):5444-5452, 2005.

Gray et al., *Cell*, 142(4):637-646, 2010.

Gupta et al., *Appl. Microbiol. Biotechnol.*, 59(1):15-32, 2002.

Han et al., *Appl. Environ. Microbiol.*, 78(9):3249, 2012.

Hedge and Keenan (2011).

Hedstrom, *Chem. Rev.*, 102(12):4501-4524, 2002.

Hegde and Keenan, *Nat Rev Mol Cell Biol.*, 12(12):787-98, 2011.

Huang et al., *Genetics*, 182(1):173-89, 2009.

Jung et al., *Proc. Natl. Acad. Sci. U.S.A*, 107:604-609, 2010.

Kapust et al., *Biochem. Biophys. Res. Commun.*, 294:949-955, 2002a.

Kim et al., *Anal. Biochem.*, 284(1):42-48, 2000.

Kim et al., *Appl Microbiol Biotechnol.*, 88(4):893-903, 2010.

Komano, H., Seeger, M., Gandy, S., Wang, G., Krafft, G., and Fuller, R. (1998) Involvement of cell surface glycosyl-phosphatidylinositol-linked aspartyl proteases in alpha-secretase-type cleavage and ectodomain solubilization of human Alzheimer beta-amyloid precursor protein in yeast, The Journal of biological chemistry 273, 31648-31651.

Komano, H., Rockwell, N., Wang, G., Krafft, G., and Fuller, R. (1999) Purification and characterization of the yeast glycosylphosphatidylinositol-anchored, monobasic-specific aspartyl protease yapsin 2 (Mkc7p), The Journal of biological chemistry 274, 24431-24437.

Kyte and Doolittle, *J. Mol. Biol.*, 157(1):105-132, 1982.

Ledgerwood, E., Brennan, S., Cawley, N., Loh, Y., and George, P. (1996) Yeast aspartic protease 3 (Yap3) prefers substrates with basic residues in the P2, P1 and P2' positions, FEBS letters 383, 67-71.

Lee et al., *Bioresource Tech.*, 102:9179-9184, 2011.

Li, Q., Yi, L., Marek, P., and Iverson, B. (2013) Commercial proteases: present and future, FEBS letters 587, 1155-1163.

Lim et al., *J. Biol. Chem.*, 282(13):9722-9732, 2007.

Lin et al., *J. Immunol. Methods*, 375:159-165, 2012

Marnett and Craik, *Trends Biotechnol.*, 23(2):59-64, 2005.

Matthews, D., Goodman, L., Gorman, C., and Wells, J. (1994) A survey of furin substrate specificity using substrate phage display, Protein science: a publication of the Protein Society 3, 1197-1205.

MEROPS database (merops.sanger.ac.uk)

Mohanty et al., *Protein Expr. Purif.*, 27:109-114, 2003.

Monnat et al., *Molec. Biol. Cell*, 11:3469-3484, 2000.

Nallamsrtty et al., *Protein Expr. Purif.*, 38(1):108-15, 2004.

O'Donoghuel, A. J., Eroy-Reveles, A. A., Knudsen, G. M., Ingram, J., Zhoul, M., Statnekovl, Alexander, J. B., Greninger, L., Hostetterl, D. R., Qu, G., Maltby, D. A., Anderson, M. O., DeRisi, J. L., Burlingame, J. A, and Craik, C., (2012) Global Identification of Peptidase Specificity by Multiplex Substrate Profiling, Nat Methods 9, 1095-1100.

O'Loughlin et al., *Mol. Biol. Evol.*, 23(4):764-772, 2006.

Olsen, V., Cawley, N., Brandt, J., Egel-Mitani, M., and Loh, Y. (1999) Identification and characterization of *Saccharomyces cerevisiae* yapsin 3, a new member of the yapsin family of aspartic proteases encoded by the YPS3 gene, The Biochemical journal 339 (Pt 2), 407-411.

Overall and Blobel, *Nat. Rev. Mol. Cell Biol.*, 8(3):245-257, 2007.

Paltridge, J., Belle, L., and Khew-Goodall, Y. (2013) The secretome in cancer progression, Biochimica et biophysica acta.

Park and Rapoport, *Annu Rev Biophys.*, 41:21-40, 2012.

Pelham et al., *Embo J.*, 7(6):1757-1762, 1988.

Phan, J., Zdanov, A., Evdokimov, A., Tropea, J., Peters, H., Kapust, R., Li, M., Wlodawer, A., and Waugh, D. (2002) Structural basis for the substrate specificity of tobacco etch virus protease, The Journal of biological chemistry 277, 50564-50572.

Porro, D., Sauer, M., Branduardi, P., and Mattanovich, D. (2004) Recombinant protein production in yeasts, METHODS IN MOLECULAR BIOLOGY- . . . 31, 245-259.

Ramachandran et al., *Nat. Rev. Drug Discov.*, 11(1):69-86, 2012.
Rapoport, *Nature*, 450(7170):663-9, 2007.
Remington: The Science and Practice of Pharmacy, 21st Ed. Lippincott Williams and Wilkins, 2005.
Remington: The Science and Practice of Pharmacy, 21st Ed., Pharmaceutical Press, 2011.
Rockwell, N., Wang, G., Krafft, G., and Fuller, R. (1997) Internally consistent libraries of fluorogenic substrates demonstrate that Kex2 protease specificity is generated by multiple mechanisms, Biochemistry 36, 1912-1917.
Rockwell, N., and Fuller, R. (1998) Interplay between S1 and S4 subsites in Kex2 protease: Kex2 exhibits dual specificity for the P4 side chain, Biochemistry 37, 3386-3391.
Roebroek, A., Umans, L., Pauli, I., Robertson, E., van Leuven, F., Van de Ven, W., and Constam, D. (1998) Failure of ventral closure and axial rotation in embryos lacking the proprotein convertase Furin, Development (Cambridge, England) 125, 4863-4876.
Rozan, L., Krysan, D., Rockwell, N., and Fuller, R. (2004) Plasticity of extended subsites facilitates divergent substrate recognition by Kex2 and furin, The Journal of biological chemistry 279, 35656-35663.
Scholle, M., Kriplani, U., Pabon, A., Sishtla, K., Glucksman, M., and Kay, B. (2006) Mapping protease substrates by using a biotinylated phage substrate library, Chembiochem: a European journal of chemical biology 7, 834-838.
Schechter and Berger, *A Biochem. Biophys. Res. Commun.*, 27(2):157-162, 1967.
Schilling and Overall, *Nat. Biotechnol.*, 26(6):685-694, 2008.
Seidah, N., and Prat, A. (2002) Precursor convertases in the secretory pathway, cytosol and extracellular milieu, Essays in biochemistry 38, 79-94.
Sellamuthu et al., 2008.
Sellamuthu et al., *PLoS One*, 6(7):e22554, 2011.
Semenza et al., *Cell*, 61(7):1349-1357, 1990.
Sinha, J., Plantz, B., Inan, M., and Meagher, M. (2005) Causes of proteolytic degradation of secreted recombinant proteins produced in methylotrophic yeast *Pichia pastoris*: case study with recombinant ovine interferon-tau, Biotechnology and bioengineering 89, 102-112.
Small et al., *Proteomics*, 4(6):1581-90, 2004.
Sudbery, P. (1996) The expression of recombinant proteins in yeasts, Current opinion in biotechnology 7, 517-524.
Teasdale and Jackson, *Cell Dev. Biol.* 12, 27-54, 1996.
Tropea et al., *Methods Mol. Biol.*, 498:297-307, 2009.
Varadarajan et al., *Proc. Natl. Acad. Sci. USA*, 102(19): 6855-6860, 2005.
Varadarajan et al., *Angew. Chem. Int. Ed. Engl.*, 47(41): 7861-7863, 2008.
Varadarajan et al., *Nat. Chem. Biol.*, 4(5):290-294, 2008.
Varadarajan et al., *J. Am. Chem. Soc.*, 131(50):18186-18190, 2009a.
Varadarajan et al., *Nat. Protoc.*, 4(6):893-901, 2009b.
Villa et al., *J. Biol. Chem.*, 278(43):42545-42550, 2003.
Waugh, *Protein Expr. Purif*, 80:283-293, 2011.
Wehr et al., *Nat. Methods*, 3:985-993, 2006.
Yi, L., Gebhard, M., Li, Q., Taft, J., Georgiou, G., and Iverson, B. (2013) Engineering of TEV protease variants by yeast ER sequestration screening (YESS) of combinatorial libraries, Proceedings of the National Academy of Sciences of the United States of America 110, 7229-7234.
Yi et al., (2015) *Methods Mol Biol.* 1319:81-93.
Zhou, A., Webb, G., Zhu, X., and Steiner, D. (1999) Proteolytic processing in the secretory pathway, The Journal of biological chemistry 274, 20745-20748.

What is claimed is:

1. A method for measuring the activity of an enzyme in a eukaryotic cell, comprising:
   (a) expressing in each of a plurality of eukaryotic cells: (i) a first fusion protein comprising an ER targeting sequence, an enzyme, and an ER retention sequence; and (ii) a vector encoding a first peptide;
   (b) separating or purifying said eukaryotic cells; and
   (c) sequencing nucleic acid encoding a plurality of said first peptides, wherein the sequencing comprises subtracting or eliminating endogenous kinase activity in the eukaryotic cells;

wherein the enzyme is a kinase;
   and wherein:
   (iia) the vector encodes a second fusion protein comprising: an endoplasmic reticulum (ER) targeting sequence, a surface expression sequence, the first peptide sequence, and an endoplasmic reticulum (ER) retention sequence; and
   (iib) said separating comprises separating cells based on the presence or absence of phosphorylation of at least one amino acid of the first peptide on the surface of the eukaryotic cells, wherein phosphorylation of the at least one amino acid indicates activity of the kinase;

wherein the first peptide sequence is at least partially randomized, a plurality of different first peptide sequences are encoded by each of said vectors, or a portion of the kinase is randomized.

2. The method of claim 1, wherein the enzyme is a kinase, and wherein the vector encodes a second fusion protein comprises in an N- to C-direction: an endoplasmic reticulum (ER) targeting sequence, a surface expression sequence, the first peptide sequence, and a endoplasmic reticulum (ER) retention sequence.

3. The method of claim 1, wherein the eukaryotic cell is a yeast cell.

4. The method of claim 1, wherein said sequencing comprises next-generation sequencing.

5. The method of claim 4, wherein the next-generation sequencing comprises single-molecule real-time sequencing, an ion semiconductor method, a pyrosequencing method, a sequencing by synthesis method, or a sequencing by ligation method.

6. The method of claim 1, wherein said endoplasmic reticulum (ER) targeting sequence encoded in the vector is comprised in said surface expression sequence in the vector.

7. The method of claim 6, wherein the surface expression sequence is Aga2.

8. The method of claim 1, wherein the method further comprises sequencing nucleic acid encoding the first peptides in the plurality of eukaryotic cells both before and after step (b).

9. The method of claim 8, wherein the method comprises subtracting sequencing data of said first peptide obtained before step (b) from sequencing data of said first peptide obtained after step (b).

10. The method of claim 8, wherein step (b) comprises repeated separations or multiple rounds of separation.

11. The method of claim 8, wherein step (b) comprises multiple rounds of FACS separation and expansion or culture of the eukaryotic cells.

12. The method of claim 1, wherein the method further comprises repeating steps (a) and (b).

13. The method of claim 1, wherein the method comprises repeated FACS separation and culture of the eukaryotic cells.

14. The method of claim 1, wherein the first peptide is less than 20 amino acids in length.

15. The method of claim 1, wherein the first peptide comprises 1, 2, 3, 4, 5, or 6 randomized amino acids.

16. The method of claim 1, wherein the first peptide is comprised in a protein, wherein the protein is encoded by the vector.

17. The method of claim 1, wherein said separating comprises fluorescence-activated cell sorting (FACS).

18. The method of claim 17, wherein the enzyme is a kinase and wherein step (iib) comprises FACS separation of cells via an antibody that selectively binds a phosphorylated amino acid.

19. The method of claim 18, wherein the phosphorylated amino acid is a tyrosine.

20. The method of claim 1, wherein the kinase is a human kinase.

21. The method of claim 1, wherein the enzyme is a tyrosine kinase.

22. The method of claim 1, wherein a plurality of the cells have been exposed to a test compound.

23. The method of claim 22, wherein the test compound is a kinase inhibitor.

24. The method of claim 1, wherein a first promoter controls expression of the first fusion protein, wherein the first promoter is expressable in yeast.

25. The nucleic acid of claim 24, wherein the first promoter is Gal1 or Gal10.

26. The method of claim 1, wherein the endoplasmic reticulum (ER) targeting sequence is MQLLRCFSIFSVIASVLA (SEQ ID NO:3).

27. The method of claim 1, wherein the endoplasmic reticulum (ER) retention sequence is FEHDEL (SEQ ID NO:4), KDEL (SEQ ID NO:5), HDEL (SEQ ID NO:6), or RDEL (SEQ ID NO:7).

28. A method of measuring the activity or specificity of a kinase, comprising:
   (a) expressing in a plurality of eukaryotic cells a vector encoding an endoplasmic reticulum (ER) targeting sequence and a endoplasmic reticulum (ER) retention sequence, a surface expression sequence and a first peptide sequence;
   (b) purifying or separating the cells based on the presence of a first antibody that selectively binds a phosphorylated amino acid;
   (c) sequencing nucleic acid encoding the first peptide sequences after step (b) to produce a dataset; and
   (d) subtracting or eliminating endogenous kinase activity in the eukaryotic cells from the dataset.

29. The method of claim 1, wherein the plurality of eukaryotic cells are Kex2(-/-) knockout yeast.

30. The method of claim 28, wherein the vector further encodes an epitope tag.

31. The method of claim 1, wherein the vector further encodes an epitope tag.

32. The method of claim 30, wherein the epitope tag is FLAG DYKDDDDK (SEQ ID NO:9), HA, HIS, c-Myc, VSV-G, V5, or HSV.

* * * * *

UNITED STATES PATENT AND TRADEMARK OFFICE
CERTIFICATE OF CORRECTION

PATENT NO. : 10,900,059 B2
APPLICATION NO. : 15/518789
DATED : January 26, 2021
INVENTOR(S) : Brent Iverson et al.

Page 1 of 1

It is certified that error appears in the above-identified patent and that said Letters Patent is hereby corrected as shown below:

In the Claims

In Claim 32, Column 72, Line 49, delete "FLAG".

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 68

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 1

Glu Asn Leu Tyr Phe Glu Ser
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 2

Glu Asn Leu Tyr Phe His Ser
1               5

<210> SEQ ID NO 3
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 3

Met Gln Leu Leu Arg Cys Phe Ser Ile Phe Ser Val Ile Ala Ser Val
1               5                   10                  15

Leu Ala

<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 4

Phe Glu His Asp Glu Leu
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 5

Lys Asp Glu Leu
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 6

His Asp Glu Leu
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 7

Arg Asp Glu Leu
1

<210> SEQ ID NO 8
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 8

Glu Asn Leu Tyr Phe Gln Ser
1               5

<210> SEQ ID NO 9
<211> LENGTH: 8
<212> TYPE: PRT
<213> ORGANISM: Artificial Sequence
<220> FEATURE:

```
<223> OTHER INFORMATION: Synthetic Peptide

<400> SEQUENCE: 9

Asp Tyr Lys Asp Asp Asp Asp Lys
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 10

Glu Asn Leu Tyr Phe Xaa Ser
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 11

His His His His His His
1               5

<210> SEQ ID NO 12
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 12

Gln Leu Leu Arg Cys Phe Ser Ile Phe Ser Val Ile Ala Ser Val Leu
1               5                   10                  15

Ala

<210> SEQ ID NO 13
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 13

Leu Pro Thr Glu Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 14

Val Ala Arg Arg Asp
1               5
```

```
<210> SEQ ID NO 15
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 15

Leu Pro Glu Thr Gly
1               5

<210> SEQ ID NO 16
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 16

Lys Glu Glu Leu
1

<210> SEQ ID NO 17
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 17

Lys Lys Xaa Xaa
1

<210> SEQ ID NO 18
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 18

Val Glu Lys Pro Phe Ala Ile Ala Lys Glu
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 19

Glu Gln Lys Leu Ile Ser Glu Glu Asp Leu
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 20

Tyr Pro Tyr Asp Val Pro Asp Tyr Ala
```

<210> SEQ ID NO 21
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 21

Tyr Thr Asp Ile Glu Met Asn Arg Leu Gly Lys
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 22

Gln Pro Glu Leu Ala Pro Glu Asp Pro Glu Asp
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 23

Gly Lys Pro Ile Pro Asn Pro Leu Leu Gly Leu Asp Ser Thr
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 24

Xaa Asn Leu Xaa Phe Xaa Xaa
1               5

<210> SEQ ID NO 25
<211> LENGTH: 85
<212> TYPE: DNA
<213> ORGANISM: Artificial Sequence
<220> FEATURE:
<223> OTHER INFORMATION: Synthetic Primer

<400> SEQUENCE: 25
ctagtatcga tgcagttact tcgctgtttc tcaatctttt cggtgattgc tagcgtttta    60
gcacaggaac tgacaactat atgcg                                         85

<210> SEQ ID NO 26
<211> LENGTH: 179
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (130)..(131)
<223> OTHER INFORMATION: n is a, c, g, or t
<220> FEATURE:
<221> NAME/KEY: misc_feature
<222> LOCATION: (133)..(134)
<223> OTHER INFORMATION: n is a, c, g, or t
<220> FEATURE:
<221> NAME/KEY: misc_feature
<222> LOCATION: (136)..(137)
<223> OTHER INFORMATION: n is a, c, g, or t
<220> FEATURE:
<221> NAME/KEY: misc_feature
<222> LOCATION: (139)..(140)
<223> OTHER INFORMATION: n is a, c, g, or t
<220> FEATURE:
<221> NAME/KEY: misc_feature
<222> LOCATION: (142)..(143)
<223> OTHER INFORMATION: n is a, c, g, or t

<400> SEQUENCE: 26
ggagacttga ccaaacctct ggcgaagaat tgttaattaa gagcgcatgc cgactcctgc    60
agtcacaatt cgtcgtgttc gaaactacca gcgtagtctg gaacgtcgta tgggtaacta   120
ccactgccsn nsnnsnnsnn snnactacca ctgcctttat cgtcgtcatc tttataatc    179

<210> SEQ ID NO 27
<211> LENGTH: 24
<212> TYPE: DNA
<213> ORGANISM: Artificial Sequence
<220> FEATURE:
<223> OTHER INFORMATION: Synthetic Primer

<400> SEQUENCE: 27
gcgtagtctg gaacgtcgta tggg                                           24

<210> SEQ ID NO 28
<211> LENGTH: 173
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (124)..(125)
<223> OTHER INFORMATION: n is a, c, g, or t
<220> FEATURE:
<221> NAME/KEY: misc_feature
<222> LOCATION: (127)..(128)
<223> OTHER INFORMATION: n is a, c, g, or t
<220> FEATURE:
<221> NAME/KEY: misc_feature
<222> LOCATION: (133)..(134)
<223> OTHER INFORMATION: n is a, c, g, or t
<220> FEATURE:
<221> NAME/KEY: misc_feature
<222> LOCATION: (142)..(143)
<223> OTHER INFORMATION: n is a, c, g, or t

<400> SEQUENCE: 28
ggagacttga ccaaacctct ggcgaagaat tgttaattaa gagcgcatgc cgactcctgc    60
agtcacaatt cgtcgtgttc gaaactacca gcgtagtctg gaacgtcgta tgggtaactg   120
ccsnnsnnga asnncaaatt snnactacct ttatcgtcgt catctttata atc        173

<210> SEQ ID NO 29
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 29

Leu Pro Glu Thr Ala
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: Xaa is Ala or Gly

<400> SEQUENCE: 30

Leu Pro Glu Thr Xaa
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 31

Arg Leu Thr Pro Arg
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 32

Ser Pro Ala Lys Arg
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 33

Ala Arg Lys Pro Ala
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Peptide

```
<400> SEQUENCE: 34

Gly Ser Phe Arg Pro
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 35

Asn Ala Phe Ser His
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 36

Ala Leu Ala Arg Arg
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 37

Leu Arg Pro Arg Ala
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 38

Ala Leu Ser Arg Arg
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 39

Arg Leu Arg Pro Arg
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 40
```

Arg Leu Leu Pro Arg
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 41

Arg Leu Ser Arg Arg
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 42

Pro Leu Leu Pro Arg
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 43

Pro Leu Leu Arg Arg
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 44

Pro Leu Arg Pro Arg
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 45

Arg Leu Ala Pro Arg
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 46

```
Ala Leu Leu Pro Arg
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 47

Pro Leu Leu Ala Arg
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 48

Pro Leu Val Pro Arg
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 49

Ser Leu Arg Arg Arg
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 50

Leu Leu Cys Lys Arg
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 51

Leu Gln Pro Arg Ala
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 52

Tyr Pro Val Cys Val
```

```
<210> SEQ ID NO 53
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 53

Ser Pro Ala Trp Arg
1               5

<210> SEQ ID NO 54
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 54

Leu Xaa Xaa Arg
1

<210> SEQ ID NO 55
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: Xaa is Leu, Phe, Met, Ile, or Val
<220> FEATURE:
<221> NAME/KEY: misc_feature
<222> LOCATION: (2)..(3)
<223> OTHER INFORMATION: Xaa can be any naturally occurring amino acid

<400> SEQUENCE: 55

Xaa Xaa Xaa Arg
1

<210> SEQ ID NO 56
<211> LENGTH: 6
<212> TYPE: PRT
<213> ORGANISM: Artificial sequence
<220> FEATURE:
<223> OTHER INFORMATION: Synthetic Peptide

<400> SEQUENCE: 56

Gly Asp Tyr Tyr Tyr Trp
1               5

<210> SEQ ID NO 57
<211> LENGTH: 6
<212> TYPE: PRT
<213> ORGANISM: Artificial sequence
<220> FEATURE:
<223> OTHER INFORMATION: Synthetic Peptide

<400> SEQUENCE: 57

Glu Tyr Tyr Tyr Ile Trp
1               5
```

```
<210> SEQ ID NO 58
<211> LENGTH: 6
<212> TYPE: PRT
<213> ORGANISM: Artificial sequence
<220> FEATURE:
<223> OTHER INFORMATION: Synthetic Peptide

<400> SEQUENCE: 58

Gln Met Tyr Phe Glu Trp
1               5

<210> SEQ ID NO 59
<211> LENGTH: 6
<212> TYPE: PRT
<213> ORGANISM: Artificial sequence
<220> FEATURE:
<223> OTHER INFORMATION: Synthetic Peptide

<400> SEQUENCE: 59

Asn Pro Tyr Phe Gln Trp
1               5

<210> SEQ ID NO 60
<211> LENGTH: 6
<212> TYPE: PRT
<213> ORGANISM: Artificial sequence
<220> FEATURE:
<223> OTHER INFORMATION: Synthetic Peptide

<400> SEQUENCE: 60

Glu Lys Tyr Phe His Trp
1               5

<210> SEQ ID NO 61
<211> LENGTH: 6
<212> TYPE: PRT
<213> ORGANISM: Artificial sequence
<220> FEATURE:
<223> OTHER INFORMATION: Synthetic Peptide

<400> SEQUENCE: 61

Asp Asp Tyr His Ile Trp
1               5

<210> SEQ ID NO 62
<211> LENGTH: 6
<212> TYPE: PRT
<213> ORGANISM: Artificial sequence
<220> FEATURE:
<223> OTHER INFORMATION: Synthetic Peptide

<400> SEQUENCE: 62

Glu Tyr Tyr Met Pro Lys
1               5

<210> SEQ ID NO 63
<211> LENGTH: 6
<212> TYPE: PRT
<213> ORGANISM: Artificial sequence
<220> FEATURE:
<223> OTHER INFORMATION: Synthetic Peptide

<400> SEQUENCE: 63

Ser Thr Tyr Asn Gln Pro
1               5
```

```
<210> SEQ ID NO 64
<211> LENGTH: 6
<212> TYPE: PRT
<213> ORGANISM: Artificial sequence
<220> FEATURE:
<223> OTHER INFORMATION: Synthetic Peptide

<400> SEQUENCE: 64

Asp Arg Tyr Tyr Trp Ser
1               5

<210> SEQ ID NO 65
<211> LENGTH: 6
<212> TYPE: PRT
<213> ORGANISM: Artificial sequence
<220> FEATURE:
<223> OTHER INFORMATION: Synthetic Peptide

<400> SEQUENCE: 65

Ala Gln Tyr Tyr His Trp
1               5

<210> SEQ ID NO 66
<211> LENGTH: 6
<212> TYPE: PRT
<213> ORGANISM: Artificial sequence
<220> FEATURE:
<223> OTHER INFORMATION: Synthetic Peptide

<400> SEQUENCE: 66

Arg Gln Tyr Arg Met Glu
1               5

<210> SEQ ID NO 67
<211> LENGTH: 6
<212> TYPE: PRT
<213> ORGANISM: Artificial sequence
<220> FEATURE:
<223> OTHER INFORMATION: Synthetic Peptide

<400> SEQUENCE: 67

Asp Gln Tyr Ala Met Glu
1               5

<210> SEQ ID NO 68
<211> LENGTH: 6
<212> TYPE: PRT
<213> ORGANISM: Artificial sequence
<220> FEATURE:
<223> OTHER INFORMATION: Synthetic Peptide

<400> SEQUENCE: 68

Gly Asp Tyr Ser Cys Tyr
1               5
```